USO11207331B2

United States Patent
Brinton et al.

(10) Patent No.: US 11,207,331 B2
(45) Date of Patent: *Dec. 28, 2021

(54) AGENTS, COMPOSITIONS AND METHODS FOR ENHANCING NEUROLOGICAL FUNCTION

(71) Applicant: University of Southern California, Los Angeles, CA (US)

(72) Inventors: Roberta Diaz Brinton, Rancho Palos Verdes, CA (US); Jun Ming Wang, Pearl, MS (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/603,267

(22) Filed: May 23, 2017

(65) Prior Publication Data

US 2017/0258810 A1 Sep. 14, 2017

Related U.S. Application Data

(63) Continuation of application No. 12/701,309, filed on Feb. 5, 2010, now abandoned, which is a
(Continued)

(51) Int. Cl.
*A61K 31/57* (2006.01)
*A61P 25/28* (2006.01)
(Continued)

(52) U.S. Cl.
CPC ............ *A61K 31/57* (2013.01); *A61K 9/0043* (2013.01); *A61K 9/06* (2013.01); *A61K 47/32* (2013.01)

(58) Field of Classification Search
CPC .......... A61K 31/57; A61K 9/06; A61K 47/32; A61P 25/28
See application file for complete search history.

(56) References Cited

U.S. PATENT DOCUMENTS 4,897,388 A 1/1990 Malluche
5,925,630 A 7/1999 Upasani et al.
(Continued)

FOREIGN PATENT DOCUMENTS

WO WO 99/045931 9/1999
WO 0230409 4/2002
(Continued)

OTHER PUBLICATIONS

Bracht et al. (Innovations in Pharmaceutical Technology, 2000; 6: 92-98).*
(Continued)

*Primary Examiner* — Marcos L Sznaidman
*Assistant Examiner* — Rayna Rodriguez
(74) *Attorney, Agent, or Firm* — Pabst Patent Group LLP

(57) ABSTRACT

Neuro-enhancing agents, compositions and methods are disclosed herein. Preferred neuro-enhancing agents of the present invention include progesterone and metabolites of progesterone, such as 3α-hydroxy-5α-pregnan-20-one (THP). These agents yield neuro-enhancing effects on neural cells that include neural progenitor and/or stem cells, whereby the agents stimulate mitosis of neural progenitor cells, stimulate neurite growth and organization, protect against neural loss, or one or more of these neural processes. Thus, the neuro-enhancing agents, compositions and methods disclosed herein are useful to reverse or prevent neurological disease or defects associated with neural loss or degeneration, such as Alzheimer's disease, neurological injuries, including injuries resulting from radiation therapy, and age-related neurological decline, including impairments in memory and learning.

18 Claims, 25 Drawing Sheets

Related U.S. Application Data continuation-in-part of application No. 12/526,604, filed as application No. PCT/US2008/066558 on Jun. 11, 2008, now Pat. No. 8,969,329.

(60) Provisional application No. 61/150,159, filed on Feb. 5, 2009, provisional application No. 60/943,187, filed on Jun. 11, 2007.

(51) Int. Cl.
| | | |
|---|---|---|
| *A61K 47/32* | (2006.01) | |
| *A61K 9/06* | (2006.01) | |
| *A61K 9/00* | (2006.01) | |

(56) References Cited

U.S. PATENT DOCUMENTS

| | | | |
|---|---|---|---|
| 5,939,407 A | 8/1999 | Landfield | |
| 6,143,736 A | 11/2000 | Upasani et al. | |
| 6,277,838 B1 | 8/2001 | Upasani et al. | |
| 6,552,010 B1 | 4/2003 | Schwartz et al. | |
| 2005/0020552 A1* | 1/2005 | Aschkenasy | A61K 9/0014 514/177 |

FOREIGN PATENT DOCUMENTS

| | | | |
|---|---|---|---|
| WO | 2005009359 | 2/2005 | |
| WO | WO-2005009359 A2 * | 2/2005 | A61K 31/56 |
| WO | WO 06/037016 | 4/2006 | |
| WO | WO 07/025064 | 3/2007 | |

OTHER PUBLICATIONS

Irwin et al (Progress in Neurobiology, 2014; 113:40-55) (Year: 2014).*
Gresack et al (Brain Research, 2006;1115:135-147 (Year: 2006).*
He et al (Exp Neurol, 2004; 189:404-412) (Year: 2004).*
He, et al., "Allopregnanolone, a progressive metabolite, enhances behavioral recovery and decreases neuronal low after traumatic brain injury", *Restorative Neurology and Neuroscience*, 22:19-31 (2004).
Borchelt, et al., "Familial Alzheimer's disease-linked presenilin 1 variants elevate Abeta1-42/1/40 ratio in vitro and in vivo", *Neuron*, 17(5):1005-13 (1996).
Brinton, "Cellular and molecular mechanisms of estrogen regulation of memory function and neuroprotection against Alzheimer's disease: recent insights and remaining challenges", *Learn. Mem.*, 8(3):131-33 (2001).
Eriksson, et al., "Neurogenesis in the adult human hippocampus", *Nat. Med.*, 4(11):131-7 (1998).
Erlandsson, et al., "Immature neurons from CNS stem cells proliferate in response to platelet-derived growth factor", *J. Neurosci.*, 21(10):3483-91 (2001).
Haughey, et al., "Disruption of neurogenesis by amyloki beta-peptide, and perturbed neural progenitor cell homeostasis, in models of Alzheimer's disease", *J. Neurochem.*, 83(6):1509-24 (2002).
Hawkinson, et al., "Substituted 3beta-phenylethynyl derivatives of 3alpha-hydroxy-5alpha-pregnan-20-one: remarkably potent neuroactive steroid modulators of gamma-aminobutyric acidA receptors", *J. Pharmacol. Exp. Ther.*, 287(1):198-.
Lesne, et al., "A specific amylcid-beta protein assembly in the brain impairs memory" *Nature*, 440:352-357 (2006).
Logg, et al., "A uniquely stable replication-competent retrovirus vector achieves efficient gene delivery in vitro and in solid tumors", *Hum. Gene Ther.*, 12(8):921-32 (2001).
Monje and Palmer, "Radiation injury and neurogenesis", *Curr. Opin. Neurol.*, 16(2):129-34 (2003).
Song, et al., "Neural stem cells from adult hippocampus develop essential properties of functional CNS neurons", *Nat. Neurosci.*, 5(5):438-45 (2002).
Van Praag, et al., "Functional neurogenesis in the adult hippocampus", *Nature*, 415(6875):1030-4 (2002).

* cited by examiner

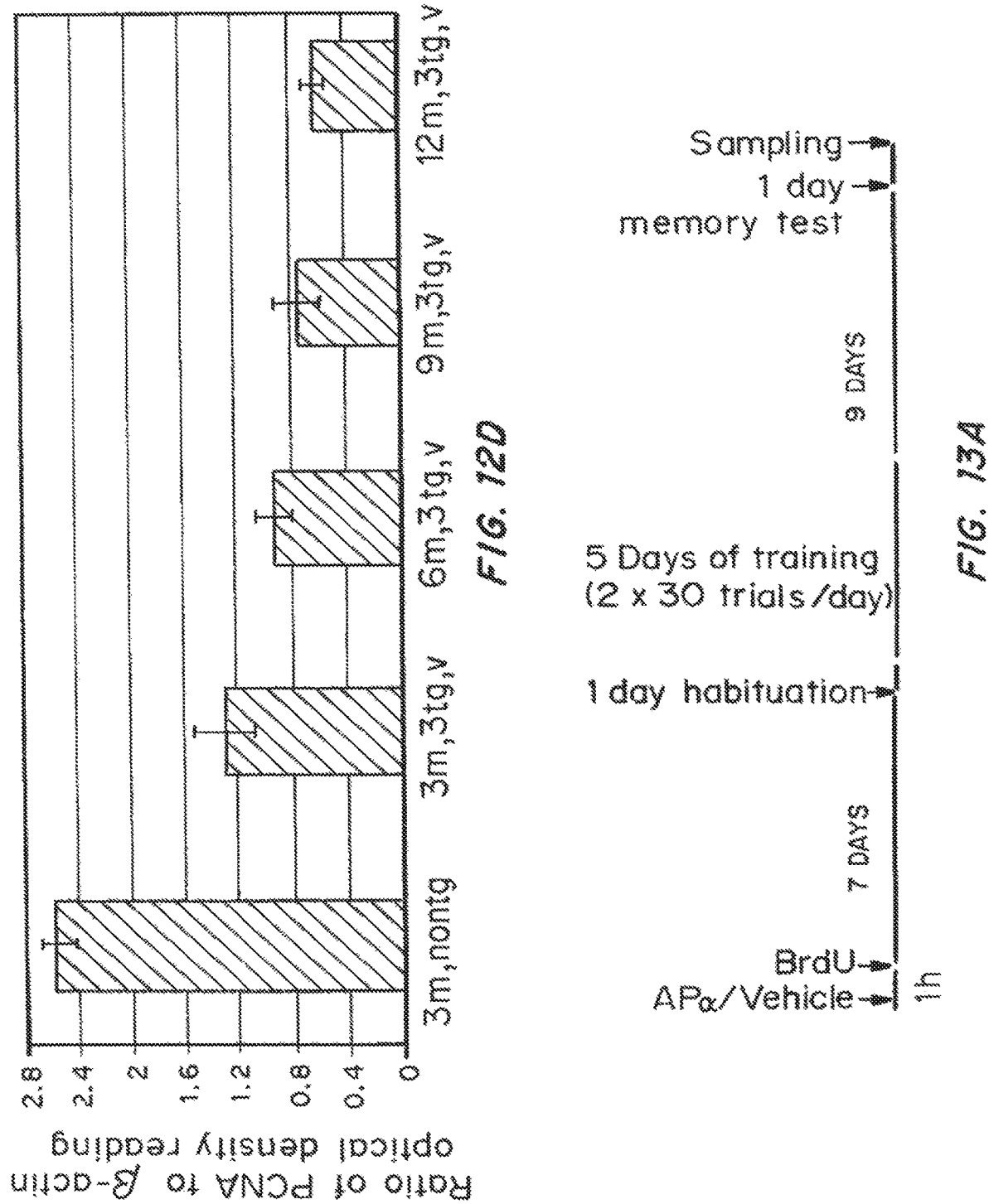

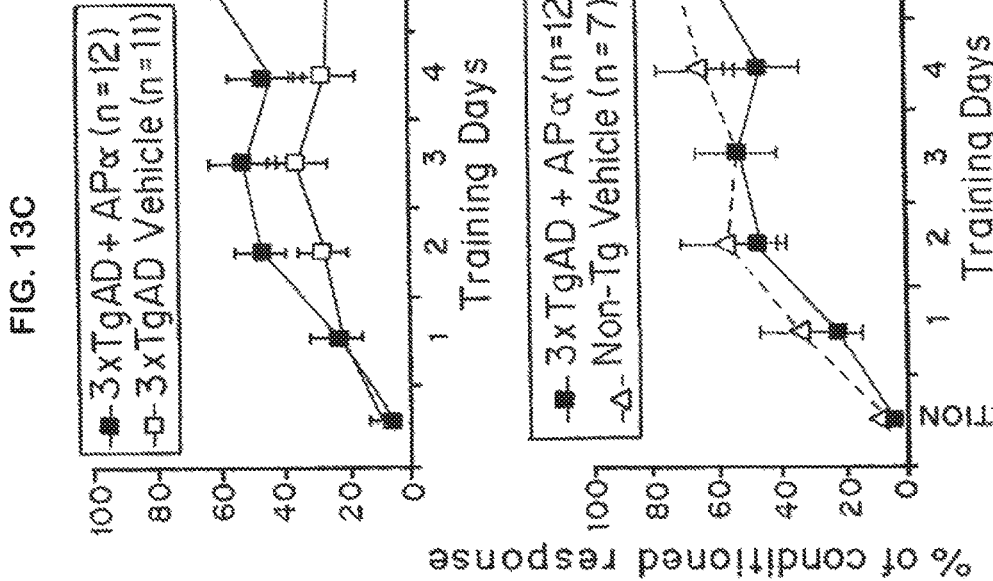
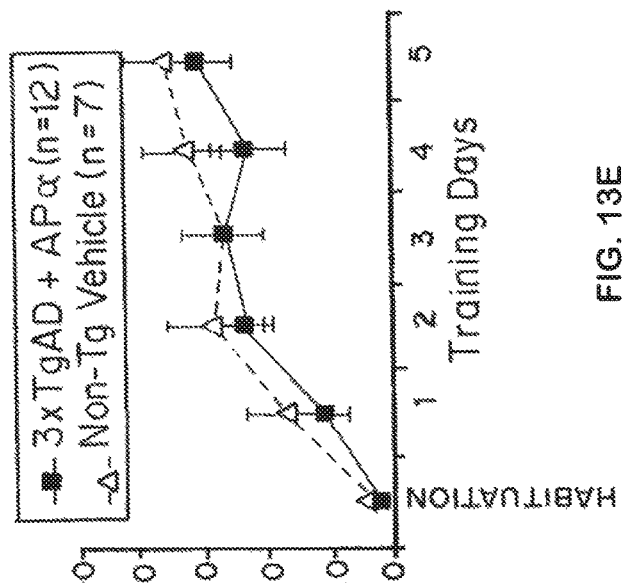
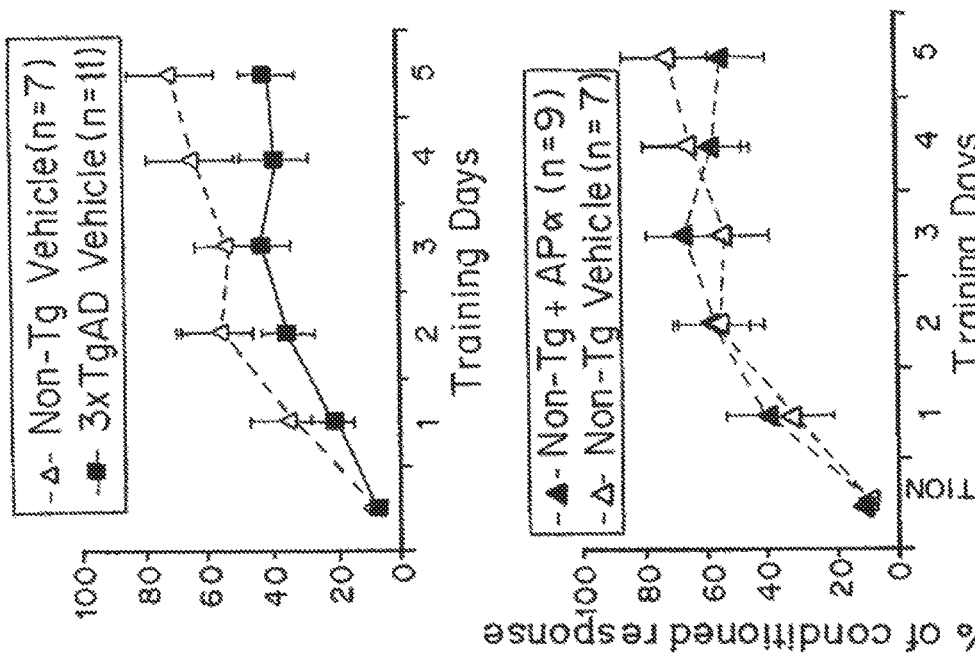

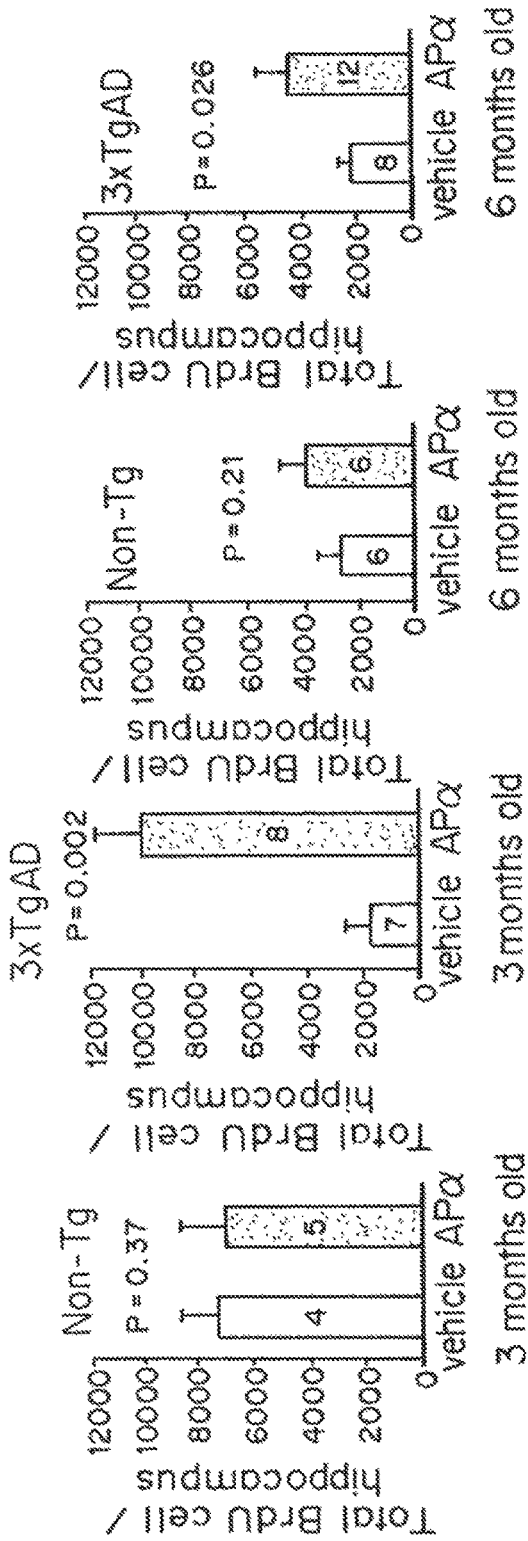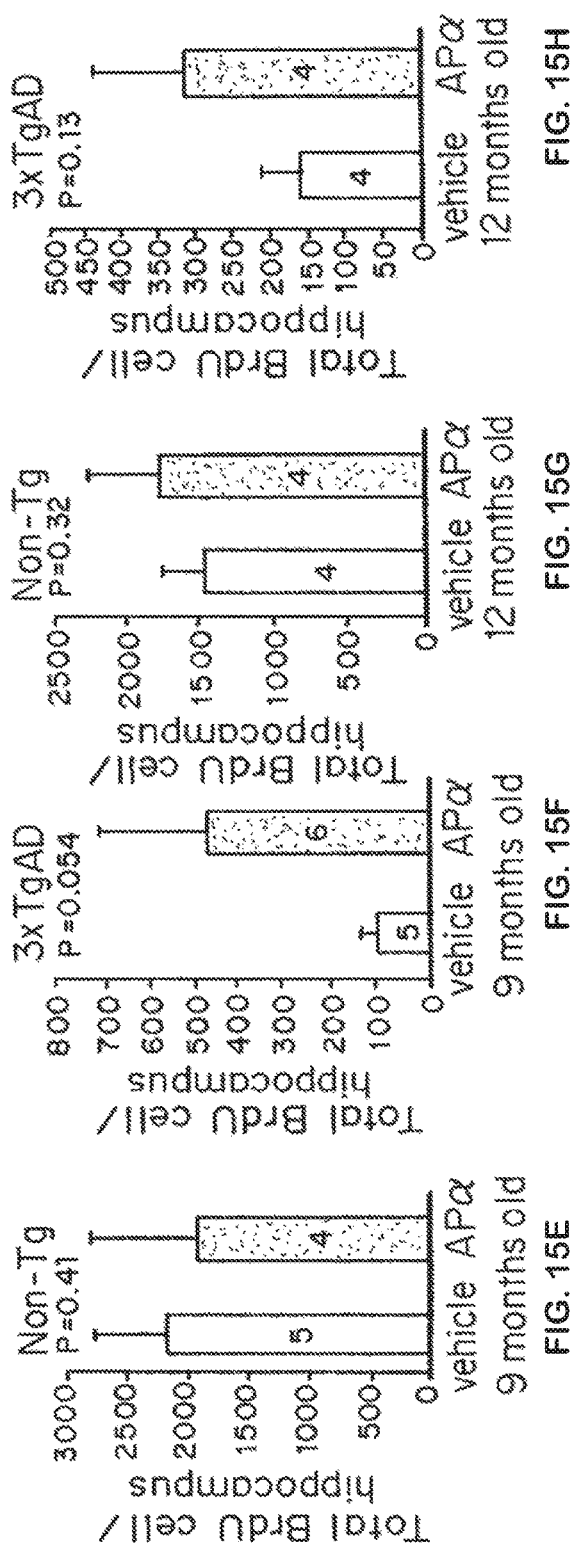

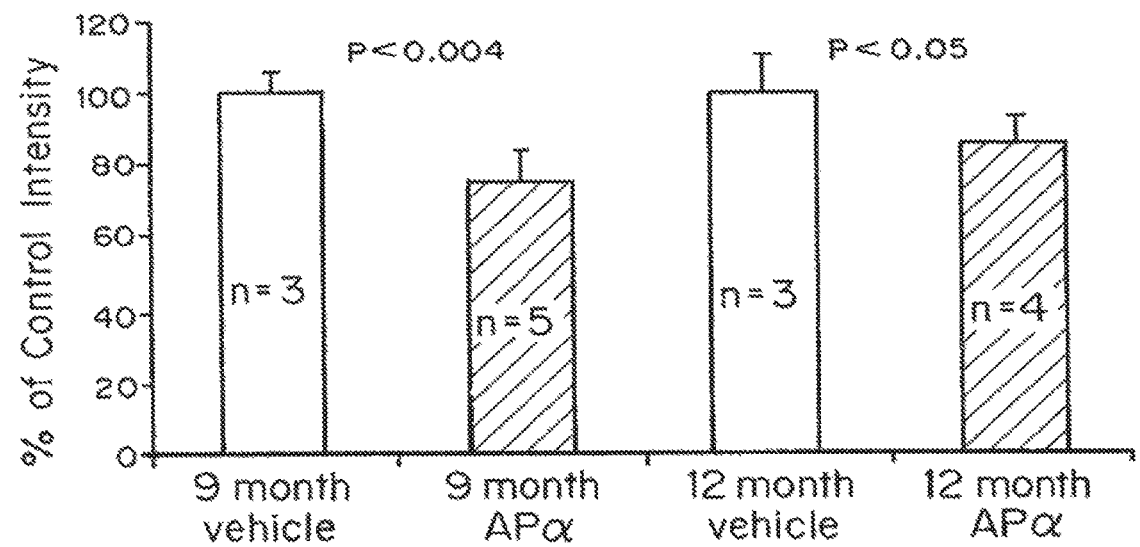
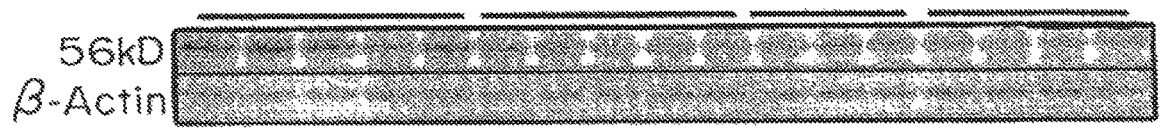
FIG. 18
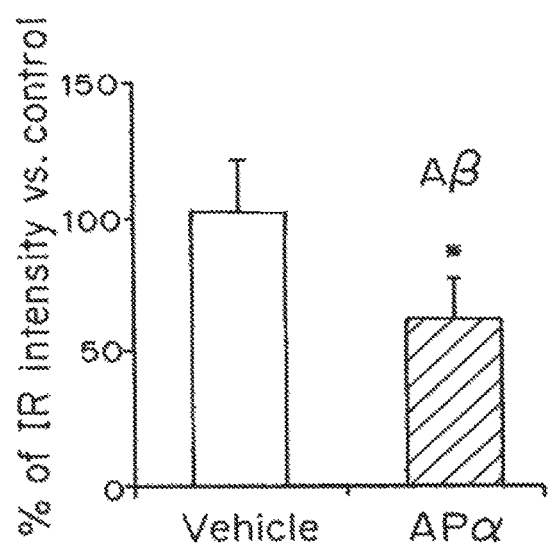
FIG. 19A
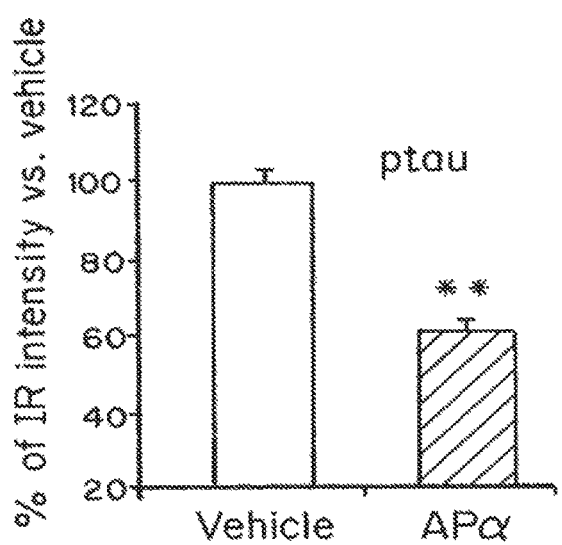
FIG. 19B

AGENTS, COMPOSITIONS AND METHODS FOR ENHANCING NEUROLOGICAL FUNCTION

CROSS REFERENCE TO RELATED APPLICATIONS

This application is a continuation of U.S. Ser. No. 12/701,309, filed on Feb. 5, 2010; which is a continuation-in-part of U.S. Ser. No. 12/526,604 entitled "Allopregnanolone in a Method for Enhancing Neurological Functions", filed on Aug. 10, 2009, now U.S. Pat. No. 8,969,329, issued Mar. 3, 2015, which is a 371 of International Application No. PCT/US2008/066558, filed on Jun. 11, 2008, which claims priority to U.S. Ser. No. 60/943,187, filed on Jun. 11, 2007; U.S. Ser. No. 12/701,309 also claims priority to U.S. Ser. No. 61/150,159 entitled "Agents, Compositions and Methods for Enhancing Neurological Function" by Roberta Diaz Brinton and Jun Ming Wang, filed on Feb. 5, 2009.

FIELD OF THE INVENTION

This invention is in the field of pharmaceutical compositions for enhancing neurological function and methods of use thereof, particularly compositions containing allopregnanolone or a derivative or analogue thereof.

BACKGROUND OF THE INVENTION

The mammalian nervous system includes a peripheral nervous system (PNS) and a central nervous system (CNS), including the brain and spinal cord, and is composed of two principal classes of cells, namely neurons and glial cells. The glial cells fill the spaces between neurons, nourishing them and modulating their function. During development, differentiating neurons from the central and peripheral nervous systems send out axons that grow and make contact with specific target cells. In some cases, axons must cover enormous distances with some growing into the periphery, whereas others are confined within the central nervous system. In mammals, this stage of neurogenesis is thought to be complete during the embryonic phase of life. Further, neuronal cells are generally thought not to multiply once they have fully differentiated.

A host of neuropathies, including neurodegenerative diseases, have been identified that affect the nervous system of mammals. These neuropathies, which may affect neurons themselves or associated glial cells, may result from cellular metabolic dysfunction, infection, injury, exposure to toxic agents, autoimmunity, malnutrition, and/or ischemia or may be due to age-related neurological changes. In some cases, the neuropathy is thought to induce cell death directly. In other cases, the neuropathy may induce sufficient tissue necrosis to stimulate the body's immune/inflammatory system and the immune response to the initial injury then destroys neural pathways. Also, neuronal tissue may be lost as a result of physical insult or trauma.

Loss of neurons, either directly or indirectly, was thought to be irreversible in the adult human brain, as it was long held that the generation of new neurons did not occur in the mature brain. In most brain regions, the generation of neurons is generally confined to a discrete developmental period. However, notable exceptions are found in the dentate gyrus and the subventricular zone of several species, where it has been shown that new neurons are generated well into the postnatal and adult period. Granule neurons are generated throughout life from a population of continuously dividing neural progenitor cells residing in the subgranular zone of the dentate gyrus in the rodent brain.

"Newborn" neurons generated from these neural progenitor cells migrate into the granule cell layer, differentiate, extend axons and express neuronal marker proteins. The mechanisms and appropriate stimuli that promote the generation of new neurons, however, are largely unknown.

Attempts to counteract the effects of acute or neurodegenerative lesions of the brain and/or spinal cord have primarily involved implantation of embryonic neurons in an effort to compensate for lost or deficient neural or neurological function. However, human fetal cell transplantation research is severely restricted. Administration of neurotrophic factors, such as nerve growth factor and insulin-like growth factor, also has been suggested to stimulate neuronal growth within the CNS.

To date, however, no satisfactory agents or treatment methods exists to repair, or counteract, the neuronal damage associated with neuropathies, such as Parkinson's disease and Alzhemier's disease, neurological injury or neurological age-related decline or impairment. Accordingly, there is a need for new treatment modalities directed to improving the adverse neurological conditions associated with neuropathies, neurological injuries and age-related neurological decline or impairment.

Therefore, it is an object of the invention to provide compositions for the treatment or prevention of neuronal damage associated with neuropathies, such as Parkinson's disease and Alzheimer's disease, neurological injury or neurological age-related decline or impairment, and methods of making and using thereof.

SUMMARY OF THE INVENTION

Compositions for the treatment or prevention of neuronal damage associated with neuropathies, such as Parkinson's disease and Alzheimer's disease, neurological injury or neurological age-related decline or impairment, and methods of making and using thereof are described herein. In one embodiment, the composition contains $\alpha$-hydroxy-5$\alpha$-pregnan-20-one (also referred to as allopregnanolone, THP, or AP$\alpha$), a derivative, analogue or prodrug thereof, a pharmaceutically acceptable salt thereof, or combinations thereof. Suitable analogues or derivatives of THP include, but are not limited to, 3-beta-phenylethynyl derivatives of 3$\alpha$-hydroxy-5$\alpha$-pregnan-20-one; analogues or derivatives of 3$\alpha$-hydroxy-5$\alpha$-pregnan-20-one that exhibit substantially equivalent neuro-enhancing activity as 3$\alpha$-hydroxy-5$\alpha$-pregnan-20-one; progesterone; and progesterone-like molecules, which are either natural metabolites of progesterone or synthetic variants of progesterone, and exhibit substantially equivalent neuro-enhancing activity as 3$\alpha$-hydroxy-5$\alpha$-pregnan-20-one.

Effective therapeutic amounts of the neuro-enhancing agents will depend on the neurological disease or defect being targeted, but generally range from about 0.1 mg to 1000 mg, preferably from about 0.1 to 500 mg, more preferably from about 0.1 to about 100 mg. In one embodiment, the compositions contain at least about 10 mg or greater of the pharmaceutically active form of 3$\alpha$-hydroxy-5$\alpha$-pregnan-20-one or an analogue, derivative, or prodrug thereof.

The compositions can be administered in a single dose or multiple doses. The compositions can be administered on a daily basis or less frequently, for example, every other day, once a week, once a month, etc. The effective administration periods depend on the particular neurological disease or defect being targeted. Generally effective administration periods are about one month or longer, but can be about six months to about one year or longer. In a preferred embodiment, 10 mg/kg of allopregnanolone is administered once per week. This dosing regimen maximizes neurogenesis and minimizes pathology burden. FIG. 1 shows the optimal allopregnanolone therapeutic regimen. The compositions are typically administered for an extended period of time, for example, at least about 10 weeks, preferably at least about 30 weeks, more preferably at least about 60 weeks, even more preferably at least about 72 weeks, and most preferably as long as the patient is receiving noticeable benefit from the treatment method. In one embodiment, the composition is administered once a week for at least 6 months.

The compositions can be formulated for oral, enteral, topical, or transdermal administration. The compositions can further contain one or more pharmaceutically acceptable excipients, carriers, and/or additives. In one embodiment, the compositions are formulated for oral administration. Suitable oral dosage forms include, but are not limited to, tablets, soft or hard, gelatin, or non-gelatin capsules, caplets, solutions, syrups, and suspensions. In a preferred embodiment, allopregnanolone is administered in a transdermal gel containing CARBOMER® 940, and ethanol. In a particularly preferred embodiment, the gel contains 10 mg/kg allopregnanolone and is administered once a week for a period of at least 3 months, preferably at least 6 months. Studies showed that the transdermal gel was as effective as subcutaneous administration (0.1% ethanol/phosphate buffered saline). In another embodiment, allopregnanolone is administered intranasally.

In one embodiment, the compositions are administered to enhance neurological function in an individual with a neurological disease, neurological injury or age-related neuronal decline or impairment. The compositions are administered over a period of time effective to stimulate neural mitosis, to prevent neuronal loss, or combination thereof. Target neurological dysfunctions and disease states include Alzheimer's disease and Parkinson's disease; neurological injuries, such as those following radiation therapy for brain-related cancers or traumatic brain injuries; and age-related memory decline and age-related learning impairments. In one embodiment, the compositions are administered to reduce β-amyloid accumulation in the brain, which is associated with Alzheimer's disease. The methods for enhancing neurological function in an individual can be practiced in-vivo and/or ex-vivo.

The compositions can also be administered to improve or restore neurological function by inducing or stimulating the generation of new neurons, protecting against neuronal loss, stimulating or inducing neurite outgrowth and organization or protecting against loss of neurites and neural networks, or combination thereof.

BRIEF DESCRIPTION OF THE DRAWINGS

FIG. 6A shows the FACS profile of vehicle; FIG. 6B shows the FACS profile of THP treated MuLV-GFP infected cells; the accompanying table FIG. 6C summarizes the FACS results. V=vehicle; THP (250 nM).

FIGS. 12A-D show the effect of 3α-hydroxy-5α-pregnan-20-one (APα) on cell proliferation in mouse hippocampus. FIG. 12A is a bar graph showing the stereological analyses of mouse dentate gyrus subgranular zone (SGZ) 24 hours following one subcutaneous dose of 3α-hydroxy-5α-pregnan-20-one (APα) (10 mg/kg) or vehicle control. Data is presented as total BrdU positive cells as a function of time (months) in nonTg and 3×Tg mice treated with vehicle or APα (THP). Moving left to right across the x-axis, Non-Tg/vehicle, Non-Tg/APα, 3×Tg/vehicle, and 3×Tg/APα are clustered for 3, 6, 9, and 12 month time points. FIG. 12B is a bar graph showing optical density reading ratio of PCNA to β-actin immunoblots in 3 month old nonTg treated with vehicle or APα (THP), and 3×Tg mice treated with vehicle or APα (THP). Immunoblots are shown below. FIG. 12C is a bar graph showing optical density reading ratio of PCNA to β-actin immunoblots in 6 month old nonTg treated with vehicle or APα (THP), and 3×Tg mice treated with vehicle or APα (THP). Immunoblots are shown below. FIG. 12D is a bar graph showing optical density reading ratio of PCNA to β-actin immuno blots in 3 month nonTg mice, and 3, 6, and 9 month Tg mice treated with vehicle. The data reveals that basal level (vehicle) of PCNA expression decreases with age and pathology in 3×TgAD mice hippocampus compared to 3 month background strain non-Tg mice.

FIG. 13A is a schematic showing the experimental design of the learning and memory experiments. FIGS. 13B-13E are graphs showing the results of 5 days training.

FIGS. 15A-15H are graphs showing that the administration of THP increases neural progenitor cell proliferation in hippocampus of 3×TgAD mice in an age dependent manner. The effect is expressed as the total BrdU cell/hippocampus in vehicle (left bar) and 3α-hydroxy-5α-pregnan-20-one (APα) treatment (right bar) for 3, 6, 9, and 12 month aged mice.

FIG. 18 is a bar graph showing that 3α-hydroxy-5α-pregnan-20-one (APα, THP) reduces beta-amyloid 56 KD expression and overall amyloid burden in 9- and 12-month old male 3×TgAD mice following once per week exposure for 6 months. Data is presented as % of control intensity from an immunoblot of the 56 kD band detected with β-amyloid antibody 6E10 (which recognizes the abnormally processed isoforms as well as precursor forms of beta-amyloid protein), in 9 month vehicle treated (control) and APα treated, and 12 month vehicle treated (control) and APα treated (from left to right across the x-axis) mice. Immunoblot is found below.

FIG. 19A is a bar graph showing the immunocytochemical detection of beta amyloid (Aβ) (% of IR intensity vs. control) in mice treated with vehicle (control) or 3α-hydroxy-5α-pregnan-20-one (APα, THP). FIG. 19B is a bar graph showing the immunocytochemical detection of phosphorylated tau (ptau) (% of IR intensity vs. control) in mice treated with vehicle (control) or 3α-hydroxy-5α-pregnan-20-one (APα, THP).

FIG. 21A is a bar graph showing the effect of α-hydroxy-5α-pregnan-20-one (alloprenanoione, APα, or THP) administered subcutaneously (0.1% ethanol/phosphate buffered saline) on the promotion of neural progenitor cell proliferation. Data is presented as BrdU cells/hippocampus as a function of APα concentration (0 mg/kg, or 10 mg/kg). FIG. 21 B is a bar graph showing the effect of 10 mg/kg α-hydroxy-5α-pregnan-20-one (APα, or THP) administered in a transdermal gel containing ethanol and Carbomer 940 on the promotion of neural progenitor cell proliferation. Data is presented as BrdU cells/hippocampus as a function of APα concentration (0 mg/kg, 5 mg/kg, 10 mg/kg or 50 mg/kg). FIG. 21 C is a bar graph showing relative protein intensity (% vs. vehicle from western blot analysis) of PCNA from three month old 3×TgAD mice treated with 0 mg/kg, or 10 mg/kg α-hydroxy-5α-pregnan-20-one (alloprenanoione, APα, or THP) administered subcutaneously (0.1% ethanol/phosphate buffered saline), or 0 mg/kg, 5 mg/kg, 10 mg/kg or 50 mg/kg α-hydroxy-5α-pregnan-20-one (alloprenanoione, APα, or THP) administered transdermally. FIG. 21 D is a bar graph showing relative protein intensity (% vs. vehicle from western blot analysis) of total cdc2 from three month old 3×TgAD mice treated with 0 mg/kg, or 10 mg/kg α-hydroxy-5α-pregnan-20-one (alloprenanoione, APα, or THP) administered subcutaneously (0.1% ethanol/phosphate buffered saline), or 0 mg/kg, 5 mg/kg, 10 mg/kg or 50 mg/kg α-hydroxy-5α-pregnan-20-one (alloprenanoione, APα, or THP) administered transdermally.

DETAILED DESCRIPTION OF THE INVENTION

I. Definitions

Figure 1:
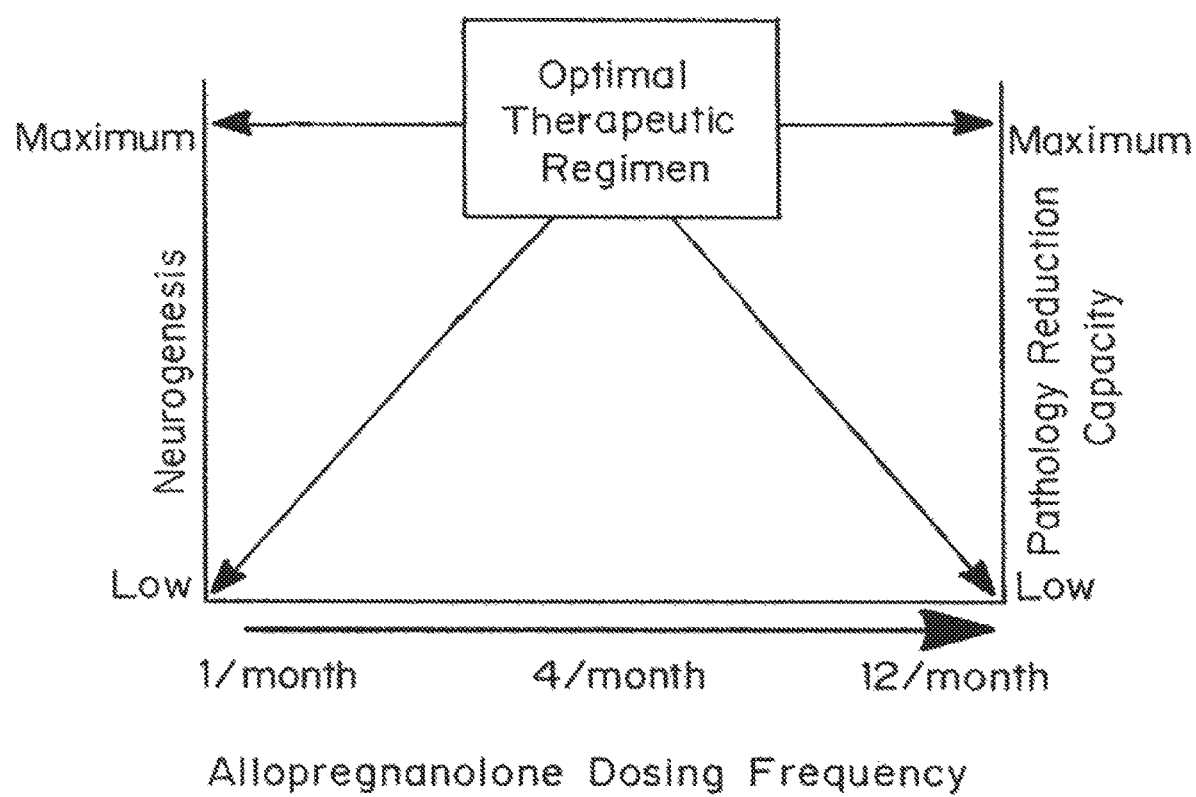
FIG. 1 is a graphical representation of the optimal allopregnanolone therapeutic regimen.

The term "analogue", as used herein, refers to a chemical compound with a structure similar to that of another (reference compound) but differing from it in respect to a particular component, functional group, atom, etc.

The term "derivative", as used herein, refers to compounds which are formed from a parent compound by one or more chemical reaction(s).

The term "prodrug", as used herein, refers to an active drug chemically transformed into a per se inactive derivative which, by virtue of chemical or enzymatic attack, is converted to the parent drug within the body before or after reaching the site of action. Prodrugs are frequently (though not necessarily) pharmacologically inactive until converted to the parent drug. Methods for converting to drugs to prodrugs are known in the art. Suitable examples of prodrugs include, but are not limited to, ester and amide prodrugs; polyethylene glycol prodrugs with or without a linker; carbonate prodrugs; and dihydroxypropyl prodrugs.

"Pharmaceutically acceptable salt", as used herein, refers to the modification of the parent compound by making the acid or base salts thereof. Example of pharmaceutically acceptable salts include, but are not limited to, mineral or organic acid salts of basic residues such as amines and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Modified release dosage form: A modified release dosage form is one for which the drug release characteristics of time, course and/or location are chosen to accomplish therapeutic or convenience objectives not offered by conventional dosage forms such as solutions, ointments, or promptly dissolving dosage forms. Delayed release, extended release, and pulsatile release dosage forms and their combinations are types of modified release dosage forms.

Delayed release dosage form: A delayed release dosage form is one that releases a drug (or drugs) at a time other than promptly after administration.

Extended release dosage form: An extended release dosage form is one that allows at least a twofold reduction in dosing frequency as compared to the drug presented as a conventional dosage form (e.g. as a solution or prompt drug-releasing, conventional solid dosage form).

Pulsatile release dosage form: A pulsatile release dosage form is one that mimics a multiple dosing profile without repeated dosing and allows at least a twofold reduction in dosing frequency as compared to the drug presented as a conventional dosage form (e.g. as a solution or prompt drug-releasing, conventional solid dosage form). A pulsatile release profile is characterized by a time period of no release (lag time) or reduced release followed by rapid drug release.

II. Compositions

A. Neuro-Enhancing Agents

The compositions described herein contain one or more neuro-enhancing agents. In one embodiment, the one or more neuro-enhancing agents are selected from progesterone or an analogue or derivative thereof, such as precursors of progesterone, progesterone metabolites and progesterone derivatives in its metabolic pathway, as well as the salts or hydrates of these analogues and derivatives. In a preferred embodiment, the compositions contains a naturally occurring metabolite of progesterone, 3α-hydroxy-5α-pregnan-20-one (APα), also known as tetrahydroprogesterone (THP), as well as the pharmaceutically acceptable salts and hydrates thereof 3α-hydroxy-5α-pregnan-20-one (THP) is generally classified as a neurosteroid as it is produced in the central nervous system and previously has been found to be an allosteric modulator of GABA receptors.

Other suitable analogs and derivatives include variant molecules of 3α-hydroxy-5α-pregnan-20-one or substituted derivatives of 3α-hydroxy-5α-pregnan-20-one, such as 3α-oxy derivatives, 3α-alkyl derivatives, 3α-alkenyl derivatives, 3α-ester derivatives, 3α-ether derivatives; 3ss-phenylethynyl derivatives of 3α-hydroxy-5α-pregnan-20-one, and 3p-phenylethynyl derivatives of 3α-hydroxy-5α-pregnan-20-one, as described in Hawkinson, et al. *J. Pharmacology & Experimental Therapeutics* 287: 198-207 (1998); as well as steroids derivatives of the 5α pregnan-20-one series such as those described in U.S. Pat. Nos. 5,925,630; 6,143,736; and 6,277, 838.

Analogs or derivatives of 3α-hydroxy-5α-pregnan-20-one include progesterone-like molecules that are either natural precursors or metabolites of progesterone or synthetic variants of progesterone that exhibit substantially equivalent neurogenic activity as 3α-hydroxy-5α-pregnan-20-one. Substantially equivalent neuro-enhancing activity is defined as approximately 30% to approximately 300% of the neuro-enhancing activity of 3α-hydroxy-5α-pregnan-20-one.

The neuro-enhancing agents are administered at dosages and for periods of time effective to stimulate or induce neural proliferation and/or to protect against neural loss in an individual. Dosage regimes may be adjusted for purposes of improving the therapeutic response to the particular composition administered. For example, several divided doses may be administered daily or the dose may be proportionally reduced as indicated by the exigencies of the therapeutic situation. The dosages of the one or more neuro-enhancing agents is in the range of about 0.1 mg to about 1000 mg, more preferably in the range of about 1 mg to about 500 mg, most preferably in the range from about 10 mg to about 100 mg. However, the particular dose depends on the particular neurological disease or defect being targeted and can be readily determined by the treating physician.

The compounds described herein may have one or more chiral centers and thus exist as one or more stereoisomers. Such stereoisomers can exist as a single enantiomer, a mixture of diastereomers or a racemic mixture. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

B. Additional Active Agents

The compositions can further contain one or more additional active agents. In one embodiment, the additional active agent is a steroid. Suitable steroids include biologically active forms of vitamin D3 and D2, such as those described in U.S. Pat. Nos. 4,897,388 and 5,939,407. The steroids may be co-administered to further aid in neurogenic stimulation or induction and/or prevention of neural loss, particularly for treatments of Alzheimer's disease. Estrogen and estrogen related molecules also may be co-administered with the neuro-enhancing agents to enhance neuroprotection as described in Brinton (2001) *Learning and Memory* 8 (3): 121-133.

Other neuroactive steroids, such as various forms of dehydroepi-androsterone (DHEA) as described in U.S. Pat. No. 6,552,010, can also be co-administered to further aid in neurogenic stimulation or induction and/or prevention of neural loss. Other agents that cause neural growth and outgrowth of neural networks, such as Nerve Growth Factor (NGF) and Brain-derived Neurotrophic Factor (BDNF), can be administered either simultaneously with or before or after the administration of THP. Additionally, inhibitors of neural apoptosis, such as inhibitors of calpains and capases and other cell death mechanisms, such as necrosis, can be co-administered with the neuro-enhancing agents o further prevent neural loss associated with certain neurological diseases and neurological defects.

C. Formulations

Depending upon the manner of introduction, the neuro-enhancing agents described herein may be formulated in a variety of ways. Formulations containing THP or other substantially equivalent variant molecules can be prepared in various pharmaceutical forms, such as granules, tablets, capsules, suppositories, powders, controlled release formulations, suspensions, emulsions, creams, gels, ointments, salves, lotions, or aerosols and the like.

In one embodiment, the neuro-enhancing agent are formulated as solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized.

In another embodiment, the formulation is administered topically or transdermally. Suitable topical and transdermal formulations include, but are not limited to, lotions, ointments, creams, and gels. In a preferred embodiment, the transdermal formulation is a gel. "Topical", as used herein, generally refers to formulations for local delivery of an active agent, for example, via a gel, lotion, cream, ointment, or patch. "Transdermal", as used herein, generally refers to systemic delivery of a drug through the unbroken skin, for example, via a gel, lotion, cream, ointment, or patch.

In another embodiment, the formulation is administered intranasally. Examples of intranasal formulations include aqueous preparations, preparations containing one or more inhalants, and dry powder formulations. The nasal mucosa is highly vascularized; the delivery of a thin layer of medication across a broad surface area can result in rapid transmucosal absorption of the medication into the blood stream and cerebral spinal fluid. This can result in more rapid achievement of therapeutic drug levels compared to oral or parenteral formulations.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of coating compositions which may include plasticizers, pigments, colorants, stabilizing agents, and glidants. Delayed release, extended release, and/or pulsatile release dosage formulations may be prepared as described in standard references known in the art. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The proportion of pharmaceutically active neuro-enhancing agent to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt. % of the active material.

2. Transdermal Formulations

Suitable transdermal formulations include lotions, ointments, creams, gels, and patches. A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers. A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes. Self generating emulsions are known to enhance the absorption of drugs as shown in the following table.

In one embodiment, the formulation is a transdermal gel. A "gel" is a semisolid system containing a dispersion of the active agent, i.e., allopregnanolone, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. "Lipophilic" refers to compounds having an affinity for lipids.

The gelling agent can be natural, semi-synthetic, or synthetic. Suitable thickening or gelling agents include, but are not limited to, acacia, acrylates/steareth-20 methacrylate copolymer, agar, algin, alginic acid, ammonium acrylate copolymers, ammonium alginate, ammonium chloride, ammonium sulfate, amylopectin, attapulgite, bentonite, $C_9$-$C_{15}$ alcohols, calcium acetate, calcium alginate, calcium carrageenan, calcium chloride, caprylic alcohol, vinyl polymers such as cross linked acrylic acid polymers with the name carbomer, such as but not limited to carbomer 910, carbomer 934, carbomer 934P, carbomer 940, carbomer 941, carboxymethyl hydroxyethylcellulose, carboxymethyl hydroxypropyl guar, carrageenan, cellulose, cellulose gum, cetearyl alcohol, cetyl alcohol, corn starch, damar, dextrin, dibenzylidine sorbitol, ethylene dihydrogenated tallowamide, ethylene dioleamide, ethylene distearamide, gelatin, guar gum, hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M is also known as Polyox WSR® N-IO, which is available from Union Carbide and as PEG-2,000; PEG-5M is also known as Polyox WSR® N-35 and Polyox WSR® N-80, both available from Union Carbide and as PEG-5,000 and Polyethylene Glycol 300,000; PEG-7M is also known as Polyox WSR® N-750 available from Union Carbide; PEG 9-M is also known as Polyox WSR® N-3333 available from Union Carbide; PEG-14M is also known as Polyox WSR® N-3000 available from Union Carbide, polyacrylic acid, polyvinyl alcohol, potassium alginate, potassium aluminum polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacrylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, and mixtures thereof.

The concentration of gelling agent can be adjusted to change the viscosity of the gel. For example, in some embodiments the formulation includes 10%, 20%, 30%, 40%, 50%, 60%, or 70% w/v of a gelling agent. Alternatively, the gelling agent can be in a range of 1-80% w/v.

Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug.

The concentration of the solvent can also be adjusted. For example, in some embodiments the formulation includes 10%, 20%, 30%, 40%, or 50% v/v of solvent. Alternatively, the solvent can be in a range of 1-50% v/v.

The gel may contain one or more penetration enhancers, for example to cross the barrier of the stratum corneum. Suitable enhancer include, but are not limited to, urea, (carbonyldiamide), imidurea, N, N-diethylformamide, N-methyl-2-pyrrolidine, 1-dodecal-azacycloheptane-2-one, calcium thioglycate, 2-pyrrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleate and non-ionic detergents such as BRIJ® 76 (stearyl poly(10 oxyethylene ether), BRIJ® 78 (stearyl poly(20)oxyethylene ether), BRIJ® 96 (oleyl poly (10)oxyethylene ether), and BRIJ® 721 (stearyl poly (21) oxyethylene ether) (ICI Americas Inc. Corp.).

Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

The gel may also contain a preservative. Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Transdermal formulations can be prepared to provide sustained or extended release of the neuro-enhancing agents.

In a preferred embodiment, the gel contains ethanol as a solvent and carbomer 940 as the gelling agent.

3. Intranasal Formulations

In one embodiment, the compounds described herein are formulated for intranasal administration for delivery of the compounds to the brain. The olfactory mucosa are in direct contact with the brain and CSF. Therefore, medications absorbed across the olfactory mucosa directly enter the CSF. This provides a rapid, direct route for drug delivery to the brain. Bioavailability for drugs can be much higher when administered intranasally versus other routes of administration. Further, intranasal administration avoids the gut thereby bypassing first pass metabolism by the liver.

The compounds can be formulated as solutions or suspensions in an aqueous or organic solvent or as a dry powder. For suspensions and dry powder formulations, particles sizes of 10-50 microns adhere best to the nasal mucosa, as smaller particles may pass on to the lungs and larger particles can form droplets and run out of the nose. Atomized drugs are typically more effective than liquids since they provide larger surface area coverage and the smaller particle size provides a thin layer to cover the mucosa.

Compounds can be administered intranasally in the form of drops which are administered using a syringe or dropper, sprays or atomized formulations which provide a unit dose, such as a via syringe or a unit dose pump, or nebulized formulations. Devices for administering drugs intranasally are well known in the art.

Intranasal formulations may contain one or more excipients, such as penetration enhancers, surfactants, preservatives, etc.

4. Enteral Formulations

Pharmaceutical compositions for oral administration can be liquid or solid. Liquid dosage forms suitable for oral administration include, but are not limited to, pharmaceutically acceptable emulsions, microemulsions, solutions, suspensions, syrups and elixirs. In addition to an encapsulated or unencapsulated HDAC inhibitor, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan and mixtures thereof. Besides inert diluents, the oral compositions can also include adjuvants, wetting agents, emulsifying and suspending agents, sweetening, flavoring and perfuming agents.

Solid dosage forms for oral administration include, but are not limited to, capsules, tablets, caplets, dragees, powders and granules. In such solid dosage forms, the encapsulated or unencapsulated compound is typically mixed with at least one inert, pharmaceutically acceptable excipient or carrier such as sodium citrate or dicalcium phosphate and/or (a) fillers or extenders such as starches, lactose, sucrose, glucose, mannitol and silicic acid, (b) binders such as, for example, carboxymethylcellulose, alginates, gelatin, polyvinylpyrrolidinone, sucrose and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also contain buffering agents.

Solid compositions of a similar type may also be employed as fill materials in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art.

5. Modified Release Formulations

The compositions described herein can be formulation for modified or controlled release. Examples of controlled release dosage forms include extended release dosage forms, delayed release dosage forms, pulsatile release dosage forms, and combinations thereof.

Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropylcellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more neuroprotective agents. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

III. Methods of Use

The compositions described herein provide an effective amount of one or more neuro-enhancing agents upon administration to an individual. As used in this context, an "effective amount" of one or more neuro-enhancing agents is an amount that is effective to improve or ameliorate one or more symptoms associated with a particular neurological disease, neurological defect or age-related neurological decline or impairment. Such a therapeutic effect is generally observed within about 4 to about 6 weeks of initiating administration of a composition containing an effective amount of one or more neuro-enhancing agents, although the therapeutic effect may be observed in less than 4 weeks or greater than 6 weeks.

The individual is preferably a mammal, and more preferably the mammal is a human who has lost some amount of neurological function as a result of neurological disease, neurological injury or age-related neurological decline or impairment. Generally neural loss implies any neural loss at the cellular level, including loss in neurites, neural organization or neural networks. Examples of other subjects who can be treated include humans, dogs, cats, rats, and mice. Lower mammal models using, for example, rats or mice can be used to predict modes of general brain aging and associated neuronal loss in higher mammals, such as humans.

The compositions can be administered daily, weekly, or less frequently in an amount to provide a therapeutically effective increase in the blood level of the one or more neuro-enhancing agents described herein. For example, the total daily dosage will be at least about 10 mg and more preferably at least about 50 mg to about 500 mg or 1000 mg, when administered orally. Capsules or tablets for oral delivery can contain up to a full daily oral dose, e.g., 100 mg or more.

Where the administration is by other than an oral route, the neuro-enhancing agents or compositions may be delivered over an extended period, e.g., 3-10 days, in an amount effective to produce at least an average daily dose of, e.g., 50 mg. Alternatively, the compositions can be formulated for controlled release, wherein the composition is administered once a day, once a week, or once a month.

In a preferred embodiment, the dosage of allopregnanolone is 10 mg/kg administered once a week. Therefore, a balance between optimal neurogenesis and optimal anti-amyloidogenic effects is predicted to be achievable with a once per week dosing schedule. The compositions are typically administered for an extended period of time, for example, at least about 10 about, preferably at least about 30 weeks, more preferably at least about 60 weeks, even more preferably at least about 72 weeks, and most preferably as long as the patient is receiving noticeable benefit from the treatment method.

In a preferred embodiment, the composition containing one or more neuro-enhancing agents is administered to an individual at a dose and for a period effective to produce an improvement in at least one criterion set forth as indicative of an improvement in the neurological disease, neurological defect or neurological age-related decline or impairment, such as an improvement in cognitive abilities, memory, motor skills, learning or the like, preferably an improvement is observed in at least two such criteria.

Criteria for assessing improvement in a particular neurological disease, neurological injury or age-related neurological change include methods of evaluating cognitive skills, motor skills, memory capacity or the like, as well as methods for assessing physical changes in selected areas of the central nervous system, such as magnetic resonance imaging (MM) and computed tomography scans (CT) or other imaging methods. Such methods of evaluation are well known in the fields of medicine, neurology, psychology and the like, and can be appropriately selected to diagnosis the status of a particular neurological impairment. To assess a change in a neurological disease, neurological injury or age-related neurological change, the selected assessment or evaluation test, or tests, are given prior to the start of administration of the neuro-enhancing agents or compositions of the present invention. Following this initial assessment, treatment methods for the administration of the neuro-enhancing agents of the present invention are initiated and continued for various time intervals. At a selected time interval subsequent to the initial assessment of the neurological defect impairment, the same assessment or evaluation test (s) is again used to reassess changes or improvements in selected neurological criteria.

The compositions described herein can be administered in a variety of ways, such as orally, parenterally (e.g., subcutaneous, intravenous, intramuscular, intraarterial, intraperitoneal, intrathecal, intracardiac, or intrasternal), transcutaneously, transmucosally, subcutaneously, by inhalation, infusion, particularly via intracerebroventricular infusion, although oral administration is generally preferred. Depending on the route of administration, the compositions may be coated with or in a material to protect it from the natural conditions which may detrimentally affect its ability to perform its intended function. A particularly convenient method of administering compositions of the present invention is via oral administration.

A. Diseases and Disorders to be Treated

Neuro-enhancement resulting from the administration of the compositions described herein includes the stimulation or induction of neural mitosis leading to the generation of new neurons, i.e., exhibiting a neurogenic effect, prevention or retardation of neural loss, including a decrease in the rate of neural loss, i.e., exhibiting a neuroprotective effect, or one or more of these modes of action. The term "neuroprotective effect" is intended to include prevention, retardation, and/or termination of deterioration, impairment, or death of an individual's neurons, neurites and neural networks. Administration of the compositions described herein leads to an improvement, or enhancement, of neurological function in an individual with a neurological disease, neurological injury, or age-related neuronal decline or impairment.

Neural deterioration can be the result of any condition which compromises neural function which is likely to lead to neural loss, Neural function can be compromised by, for example, altered biochemistry, physiology, or anatomy of a neuron, including its neurite. Deterioration of a neuron may include membrane, dendritic, or synaptic changes which are detrimental to normal neuronal functioning. The cause of the neuron deterioration, impairment, and/or death may be unknown. Alternatively, it may be the result of age-, injury- and/or disease-related neurological changes which occur in the nervous system of an individual.

When neural loss is described herein as "age-related", it is intended to include neural loss resulting from known and unknown bodily changes of an individual that are associated with aging. When neural loss is described herein as "disease-related", it is intended to include neural loss resulting from known and unknown bodily changes of an individual which are associated with disease. When neural loss is described herein as "injury-related", it is intended to include neural loss resulting from known and unknown bodily changes of an individual which are associated with injury or trauma. Examples of trauma include brain injuries due to explosions, for example from explosive devices, or other traumas, such as gun shots and/or stabbings. It should be understood, however, that these terms are not mutually exclusive and that, in fact, many conditions that result in the loss of neural cells and/or neural connections can be related to age, disease and/or injury.

Some of the more common age-related neuropathies associated with neural loss and changes in neural morphology include, for example, Alzheimer's disease, Pick's disease, Parkinson's disease, vascular disease, Huntington's disease, and Age-Associated Memory Impairment. In Alzheimer's patients, neural loss is most notable in the hippocampus, frontal, parietal, and anterior temporal cortices, amygdala, and the olfactory system. The most prominently affected zones of the hippocampus include the CA1 region, the subiculum, and the entorhinal cortex. Memory loss is considered the earliest and most representative cognitive change because the hippocampus is well known to play a crucial role in memory.

Pick's disease is characterized by severe neural degeneration in the neocortex of the frontal and anterior temporal lobes which is sometimes accompanied by death of neurons in the striatum. Parkinson's disease can be identified by the loss of neural cells in the substantia nigra and the locusceruleus. Huntington's disease is characterized by degeneration of the intrastriatal and corticalcholmergic neural cells and GABA-ergLc neural cells. Rarkmson's and -Huntington's diseases are usually associated with movement disorders, but often show cognitive impairment (memory loss) as well.

Age-Associated Memory Impairment (AAMI) is another age-associated disorder that is characterized by memory loss in healthy, elderly individuals in the later decades of life. Presently, the neural basis for AAMI has not been precisely defined. However, neural death with aging has been reported to occur in many species in brain regions implicated in memory, including cortex, hippocampus, amygdala, basal ganglia, cholinergic basal forebrain, locus ceruleus, raphe nuclei, and cerebellum.

Animal Models for Evaluating Neurogenesis and/or Reducing Expression of Beta-Amyloid Aging rodent brains do not develop senile plaques and neurofibrillary tangles. Most recent studies suggest, however, that loss or shrinkage of neurons, dendrites, and/or synapses is more closely correlated with either dementia or aging than are plaques and tangles. Aging rats exhibit neural cell loss in the pyramidal cells of the hippocampus, especially in field CA1, as well as cell loss or dendritic/synaptic changes in some other brain regions. Moreover, aging rodents show extensive hippocampalastrocyte hypertrophy just as do aging humans. In addition, loss of neural cells in field CA1 of the hippocampus is a consistent correlate of aging across species, and is also prominent in human neurodegenerative diseases, such as Alzheimer's disease. For these reasons, the study of neural loss in aging rats, for example, is predictive of general mechanisms of brain aging and associated neural loss in humans due to diseases such as Alzheimer's diseases.

Animal models, such as the models described in U.S. Pat. No. 5,939,407 and Haughey et al., *J. Neurochem.* 83: 1509-1524 (2002), represent improvement in models for age-associated disease and decline because they relate to an intact animal, which is generally preferred over tissue culture models. Further, the animal model described in U.S. Pat. No. 5,939,407 employs a strain of rat that was developed by the National Institute on Aging as a premier model of mammalian aging. The particular rat strain (Brown Norway/Fischer 344 F1 cross rats) was selected due to its normal pattern of aging, with few indications of abnormal pathology. This strain also loses neural cells in field CA1 of the hippocampus with aging and exhibits memory loss. This system represents one of the most natural animal models of neural degeneration and/or deterioration because it reflects a gradual loss of neural cells. Furthermore, the neural loss is not provoked by experimental intervention or abnormal pathology. Its brain aging pattern is also highly analogous to human and other mammalian species brain aging patterns.

In one embodiment, an animal model can be used to evaluate the effect of a neuro-enhancing agent in beta-amyloid expression and/or neurogenesis in an animal transgenic for Alzheimer's disease. Suitable models include the animal model described by Borchelt et al. (1996) *Neuron* 17: 1005-1013 and Haughey et al. (2002) *J. Neurochemistry* 83: 1509-1524. Male mice (12-14 months old) overexpressing a mutant form of amyloid precursor protein (APP) are maintained on a 12 hour light/12 hour dark cycle with free access to food and water. This line of mice exhibits increased levels of soluble amyloid beta protein and develops amyloid deposits in an age-dependent manner with diffuse deposits first appearing at about 12 months of age and plaque-like deposits developing later, typically by 18-22 months of age.

Neural loss through disease, age-related decline or physical insult leads to neurological disease and impairment. The compositions described herein can counteract the deleterious effects of neural loss by promoting development of new neurons, new neurites and/or neural connections, resulting in the neuroprotection of existing neural cells, neurites and/or neural connections, or one or more these processes. Thus, the neuro-enhancing properties of the compositions described herein provide an effective strategy to generally reverse the neural loss associated with degenerative diseases, aging and physical injury or trauma.

The administration of 3α-hydroxy-5α-pregnan-20-one, or a substantially equivalent variant molecule, to an individual who is undergoing or has undergone neural loss, as a result of a disease, defect, injury, or age-related decline, can generally provide an effective therapeutic strategy for the treatment of neurological conditions caused by neural loss. The defects and diseases that can benefit from administering the agents, compositions and methods of the present invention include, but are not limited to, spinal cord injury, stroke, head injury, epilepsy, Parkinson's disease and Alzheimer's disease. Moreover, given that 3α-hydroxy-5α-pregnan-20-one, and substantially equivalent variant molecules, possess neuro-enhancing activities, these agents and compositions may also be administered to improve age-related memory and learning impairments.

The examples demonstrate that administration of α-hydroxy-5α-pregnan-20-one or tetrahydroprogesterone (THP or APα) reverses the learning deficits of mice transgenic for Alzheimer's diseases (3×TgAD mice). The data indicate that at 3 months, 3×TgAD mice exhibit a learning deficit relative to the performance of normal non-Tg mice. In the normal high functioning non-Tg mice, with a concomitant high level of neurogenesis, THP did not augment the learning performance. In contrast, THP significantly increased the learning performance of 3×TgAD mice to a level comparable to non-Tg mice such that the performance of THP treated 3×TgAD mice was not statistically different from the normal non-Tg mouse. One week following the learning trial, mice were tested for memory of the learned association. Non-Tg mice exhibited slightly less than 50% of the conditioned response compared to a 28% response rate of 3×TgAD mice. THP did not significantly augment the memory performance of non-Tg mice. However, THP treated 3×TgAD mice exhibited a significant increase in memory to a level comparable to the normal non-Tg mice.

As also shown in the examples, 3α-hydroxy-5α-pregnan-20-one or tetrahydroprogesterone (THP), a naturally occurring metabolite of progesterone, was found to induce or stimulate the formation of new hippocampal neurons. Results of these analyses demonstrate that the number of mitotic neural cells was approximately doubled in the presence of tetrahydroprogesterone.

The examples also demonstrate that the administration of 3α-hydroxy-5α-pregnan-20-one (THP) reduces age-related β-amyloid expression. The development of intraneuronal beta amyloid is typically seen in 6 and 9 month old animals and the development of plaques in 12 month old animals. Plaques are rarely seen in 9 month old animals. THP (10 mg/kg/week, administered once a week for 6 months) was administered to 9- and 12-month male mice transgenic for Alzheimer's disease (3×Tg-AD). The 9 month old animals were started on THP at 3 months of age prior to the development of beta amyloid accumulation in the whereas the 12 month old animals were started on THP at 6 months of age when beta amyloid had already begun to accumulate within neurons. The results indicate that administration of THP significantly decreased the amount of beta amyloid in the cerebral cortex of male mice transgenic for Alzheimer's disease.

Western Blot analysis showed a form of beta amyloid termed Abeta*56, which is the oligomer (multiple amyloid beta peptides joined together) that, in animal studies, leads to memory loss in both transgenic Alzheimer mouse models and in rats injected with Abeta*56. In the 12 month old animals, the level of Abeta*56 was much lower, likely due to the development of beta amyloid plaques in these animals, which reduces the amount of Abeta*56. Immunocytochemical detection of beta amyloid showed that administration of THP substantially decreases Abeta*56 in hippocampal neurons. THP also decreases the immunoreactivity of phosphorylated tau, which is the basis for neurofibrillary tangles.

Several treatment regimens of THP at 10 mg/kg were evaluated including 24 hours following a single dose. Further, allopregnanolone in three long-term treatment paradigms was also tested: 2) single dose followed by cognitive testing over three week duration and biochemical analyses at endpoint; 3) once per week for six months; and 4) every other day dosing for three months. An optimal treatment regimen was found to be THP 10 mg/kg once per week beginning at middle age (6 month old mice) to significantly decrease amyloid deposits.

Allopregnanolone has been shown to: (1) be a proliferative factor for human, rat, and mouse neural progenitor cells; (2) promote neurogenesis in both proliferative zones of the brain; and (3) promote neurogenesis in a mouse model of Alzheimer's disease which restored learning and memory function to normal. Allopregnanolone violates none of the Lipinski rules for drugability, referred to as the Rule of 5 (RO5). The RO5 states that the MW≤500, Clog P≤5, the number of H-bond donors ≤5, and the number of H-bond acceptors (sum of N and O atoms)≤10. Additional criteria include that the polar surface area ≤140 Å$^2$ or the sum of H-bond donors and acceptors ≤12 and the number of rotatable bonds ≤10.

The compositions described herein may also be effective for the treatment of neural damage caused by therapies aimed at combating certain cancers that affect the brain. For instance, cranial radiation therapy is crucial to the successful treatment of many primary brain tumors, cancers metastatic to the brain, CNS involvement of leukemia/lymphoma, and head and neck cancers. Such irradiation that involves the cerebrum causes a debilitating cognitive decline in both children and adults. Experiments have shown that hippocampus-dependent learning and memory are strongly influenced by the-activity of neural progenitor- and/or stem cells and their-proliferative progeny. Since the hippocampal granule cell layer undergoes continuous renewal and structuring by the addition of new neurons, radiation at much lower does than that needed to injure the more resistant post-mitotic neurons and glia of the brain, has been found to affect these highly proliferative progenitors and/or stem cells severely. The progenitor and/or stem cell, therefore, is considered to be so sensitive to radiation that a single low dose to the cranium of a mature rat is sufficient to ablate hippocampal neurogenesis. Recent experiments have further found that progressive learning and memory deficits following irradiation may be caused by the accumulating hippocampal dysfunction that results from a long-term absence of normal progenitor and/or stem cell activity. Thus, given the neurogenic effect compositions described herein on hippocampal cell cultures, therapeutic methods utilizing these compositions may benefit individuals who are undergoing or have undergone radiation therapy for brain-related cancers.

IV. Kits

The compositions described herein can be packaged in kit. The kit can include a single dose or a plurality of doses of a composition containing one or more neuro-enhancing agents, and instructions for administering the compositions. Specifically, the instructions direct that an effective amount of the composition be administered to an individual with a particular neurological disease, defect or impairment as indicated. The composition can be formulated as described above with reference to a particular treatment method and can be packaged in any convenient manner.

The instructions can be affixed to the packaging material or can be included as a package insert. While the instructions typically comprise written or printed materials they are not limited to such. Any medium capable of storing such instructions and communicating them to an end user is contemplated by this invention. Such media include, but are not limited to, electronic storage media (e. g., magnetic discs, tapes, cartridges, chips), optical media (e. g., CD ROM), and the like. As used herein, the term "instructions" can include the address of an internet site that provides the instructions. Embodiments of the present invention also include the use of the above-described pharmaceutical products for the treatment of a human patient with a neurological disease, neurological defect or age-related neurological decline or impairment.

The following examples are put forth so as to provide those of ordinary skill in the art with a complete disclosure of how to make, to use and to evaluate the therapeutic agents, compositions and methods of the present invention, and are not intended to limit the scope of what is regarded as the invention. Efforts have been made to ensure accuracy with respect to numbers presented (e, g, amounts, concentrations, etc.), but some experimental errors and deviations should be allowed for.

EXAMPLES

Materials and Methods

The animals studies described below for evaluating neurogenesis and/or reduction of beta-amyloid expression were done using a triple transgenic Alzheimer's disease (AD) mouse model (3×TgAD). The 3×TgAD mouse carries mutations (APPSwe, PS1M146V and tauP301L) of three human familial AD genes and manifests age-dependent neuropathology of both β-amyloid plaque formation and neurofibrillary tangles. In addition to expressing neuropathological markers of AD, the 3×TgAD mouse exhibits learning and memory deficits as early as 4 months, but not 2 months.

Breeding pairs of the triple transgenic Alzheimer's disease mouse (3×TgAD, homozygous mutant of human APPswe, tauP301L, and PS1M146V) and its background (129/SvxC57BL/6) were obtained from Dr. Frank Laferla (University of California at Irvine) and the colonies were established at the University of Southern California. The characterization of amyloid and tau pathologies and synaptic dysfunction in this line of mice has been described previously and confirmed in our laboratory. Mice were genotyped regularly to confirm the purity of the colony.

Using this AD model, the following were assessed: 1) THP concentration, neurogenic and cognitive status at 3 months of age; 2) impact of THP on both neurogenic and cognitive status using unbiased stereology, phenotype immunocytochemistry, real-time RT-PCR, Western blot, and eyeblink trace conditioning training and memory.

Experiments were performed using 6, 9, 12, and 15-month-old male 3×TgAD and non-Tg mice. The number of mice per condition is indicated within the results section. Mice were maintained under a 12 hr light/dark cycle with continuous access to food and water.

THP stock solution was prepared in pure ethanol and diluted in PBS before injection (with a final ethanol concentration of 0.002% of the body weight). THP transdermal gels were prepared using techniques known in the art.

Mice of each genotype and age received a subcutaneous (s.c.) injection of THP at a concentration of 10 mg/kg body weight (BW), an optimal dose of THP-□ based on our previous studies. One hour after THP injection, mice were intraperitoneally (i.p.) injected with 100 mg/kg BW bromodeoxyuridine (BrdU). Two experimental paradigms were used: 1) THP treatment for behavior and cell survival assessment, in which animals received a single shot of THP/vehicle, followed by a 7-day neurogenesis and migration phase, followed by a 5-day trace-conditioning test followed 9 days later by a 1-day memory test, and scarified 21 days after a single THP injection at which time FACS analysis of BrdU positive cells was performed to assess cell survival; 2).

Acute THP treatment for cell proliferation assessment, in which animals received a single injection of THP/vehicle and were sacrificed 24 hr later followed by quantitative unbiased stereology of BrdU positive cells. Timing of THP and BrdU injections, training diagrams, and perfusion were based on previous studies showing that learning enhances the survival of newly born cells generated 1 week before training and from our previous analysis indicating that THP-induced neurogenesis significantly increased learning of trace eyeblink conditioning in 3 month old 3×TgAD male mice following an injection of THP one week prior to behavioral testing.

All experiments strictly conformed to the Animal Welfare Act, Guide to Use and Care of Laboratory Animals, and the U.S. Government Principles of the Utilization and Care of Vertebrate Animals Used in Testing, Research, and Training guidelines on the ethical use of animals. In addition, the minimal number of required animals was used for these experiments and pain was minimized.

Trace Eyeblink Conditioning

Under deep anesthesia by intraperitoneal (i.p.) injection with ketamine (100 mg/kg i.p.) and xylazine (25 mg/kg i.p.), a 4 pin head stage (DIGI-KEY) was cemented to the skull of 3 month old male mouse with dental acrylic. The connector has four Teflon-coated stainless steel wires and one bare stainless steel wire (0.003" bare and 0.0055" coated, A-M Systems, Inc.). The bare wire was attached via a gold pin (Time Electronics) to the head stage. Coated wires were implanted s.c. in the orbicularis oculi dorsal to the left upper eyelid to record the EMG and s.c. periorbitally to deliver the shock US (3). All animals were then placed on a warm isothermal pad after surgery to recovery for 30 min. After surgery, mice were individually housed, provided with ad libitum access to food and water, and maintained on a 12 hr light/dark cycle.

After one week of acclimation to the colony room, mice with no obvious adverse responses to surgery were randomly assigned to an experimental condition. Mice were injected subcutaneously (s.c.) with 10 mg/kg THP or vehicle followed one hour later with an IP injection of BrdU (100 mg/kg). Following injection of test compound, mice were returned to their home cage for 7 days prior to onset of behavioral testing.

During the first day of training, mice were placed within Plexiglas cylinders in a sound-attenuated chamber and were habituated to the test environment for one session consisting of 30 stimulus-free trials at 30-60 sec inter-trial intervals while spontaneous eye-blink activity was recorded using electromyographic (EMG) activity recorded from the obicularis oculi dorsal to the orbit during each trial. EMG activity was rectified, and integrated using custom designed computational Labview routines.

Following habituation to the test environment mice underwent a learning phase and were trained for five days. Mice were trained by pairing delivery of a tone (CS, 250 msec, 2 kHz, 85 dB) as the conditioned stimulus followed by a 250 msec period of no stimuli, followed by the periobital shock as the unconditioned stimulus (US, 100 msec). Mice received two blocks of 30 trials per day (30-60-sec inter-trial intervals, 3-4-h inter-block intervals). This trace eye-blink conditioning paradigm is subthreshold for inducing neurogenesis. The unpaired group received random tone at the same magnitude as the paired conditioning and shock with 15-30 sec as inter-trial intervals and a total of 60 trials for one session per day. Shock intensity was adjusted daily for each mouse to elicit a head-movement response. Following the learning phase, mice were returned to their home cage for eight days followed on the ninth day by a single session to assess memory of the conditioned response. The percentage of CR was computed as the ratio of the number of CRs to the total number of valid trials. Animals were perfused at the end of the memory trial day.

Animal Dissection and Tissue Collection

Mice were sacrificed 24 h after THP administration for cell proliferation assessment or at the end of memory test for cell survival assessment. On the day of sacrifice mice were deeply anesthetized with a combination of ketamine (100 mg/kg) and xylazine (10 mg/kg), and perfused with PBS. Brains were dissected into two hemispheres, and one hemisphere was fixed immediately in cold 4% paraformaldehyde and was used for either stereological analysis (cell proliferation) or FACS analysis (cell survival).

Nuclei Extraction and Flow Cytometry Counting

Hippocampus was dissected from the fixed hemispheres from cell survival assessment experiment using consistent anatomical landmarks as criteria for dissection as described in the literature. The rostral ⅓ of the hippocampus lobe was removed to avoid the subventricular zone and rostral migratory stream proliferative pools. The extracted hippocampi were homogenized using Next advance 24 sample homogenizer (Next Advance Inc., NY) for 3 minutes on speed 7. This procedure lyses the plasma lemma while preserves the nuclear envelope intact. The nuclei sample was collected into a regular 1.5 mL microcentrifuge tube by washing the beads and tube 4 times using 200 μL of PBS, and then centrifuged for 10 minutes at 10,000 rpm. Once all of the nuclei were collected in a pellet, the supernatant was discarded. The pellet was then re-suspended in 600 μL of PBS plus 0.5% Triton x-100. The number of nuclear density was estimated by counting the propidium iodide (PI), a fluorescent molecule stoichiometrically binds to DNA by intercalating between the bases with no sequence preference, positive particles. Aliquots of 25 μl were re-suspended in 200 μL of a 0.2 M solution of boric acid, pH 9.0, and heated for 1 h at 75° C. for epitope retrieval. After washed in PBS, the nuclei were incubated for 24 hours at 4° C. with primary mouse monoclonal anti-BrdU antibody (1:100, Abcam, Ab12219) and subsequently with FITC-conjugated goat anti-mouse IgG secondary antibody (1:100 in PBS; Vector Labs, FI-2001). The remainder of cell suspension is diluted to 500 μL and sent for flow cytometry assay using Beckman FC 500 System with CXP Software. Propidium iodide (PI) cells were first gated on a histogram; the expressing cells were visualized on a forward/side scatter plot. PI cells were 'back-gated' on the forward/side scatter plot to eliminate debris prior to analysis; this also eliminated auto fluorescence of the sample. Gates were always set using dissociates with cell aliquots which lack of the first antibody, but which were incubated with second antibody and processed alongside the experimental procedure. PI-labeled cells in a fixed volume were gated, and the number of cells showing BrdU signal was analyzed. Data were expressed as total positive cells per hippocampus.

Western Blot

Protein was extracted from mouse hippocampus and separated by SDS gel as described in the literature. After transfer, PVDF membrane was plotted with monoclonal antibody for proliferating cell nuclear antigen (PCNA, 1:500, Zymed Laboratories Inc, San Francisco, Calif.) and then incubated with a horseradish peroxidase conjugated secondary antibody which is complementary to the primary antibody. Results were visualized by the ECL Plus Western Blotting Detection System (GE Healthcare, Amersham, Buckinghamshire, UK) followed by TMB development. Optical density was and analyzed by BioRad Quantity One software. The percent protein expression vs. control was normalized by loading control β-actin.

Unbiased Stereology

The fixed hemispheres from cell proliferation assessment experiment were sectioned into a series of 40 μm coronal sections and every sixth section in the series was processed for BrdU histolabeling by NeuroScience Associates (Knoxville, Tenn.). Prior to labeling, all slides were coded and the codes were not broken until analyses were completed. The number of BrdU labeled cells was determined by unbiased stereology (optical dissector). Systematic samplings of unbiased counting frames of 50 μm on a side with a 200 μm matrix spacing were produced using a semiautomatic stereology system (Zeiss Axiovert 200M fluorescent microscope as part of the 3iMarianas digital microscopy and a 60×SPlan apochromat oil objective (1.4 numerical aperture). Positive cells that intersected the uppermost focal (exclusion) plane and those that intersected the exclusion boundaries of the unbiased sampling frame were excluded from analysis. Cells that met analysis criteria through a 20 μm axial distance were counted according to the optical dissector principle. The granule cell layer reference volume was determined by summing the traced SGZ, granule cell areas for each section multiplied by the distance between sections sampled. The mean granule cell number per dissector volume was multiplied by the reference volume to estimate the total granule cell number. The stereologically determined number of BrdU-positive cells was related to the granule cell layer sectional volume and multiplied by the reference volume to estimate the total number of BrdU-positive cells.

Statistical Analysis

Data were analyzed using a one-way ANONA followed by Neuman-Keuls post hoc analysis. Data displayed in graphs were reported as mean±SEM or fold change±SEM. P-values of <0.05 were considered to be significant regardless of the statistical test used.

Figure 2:
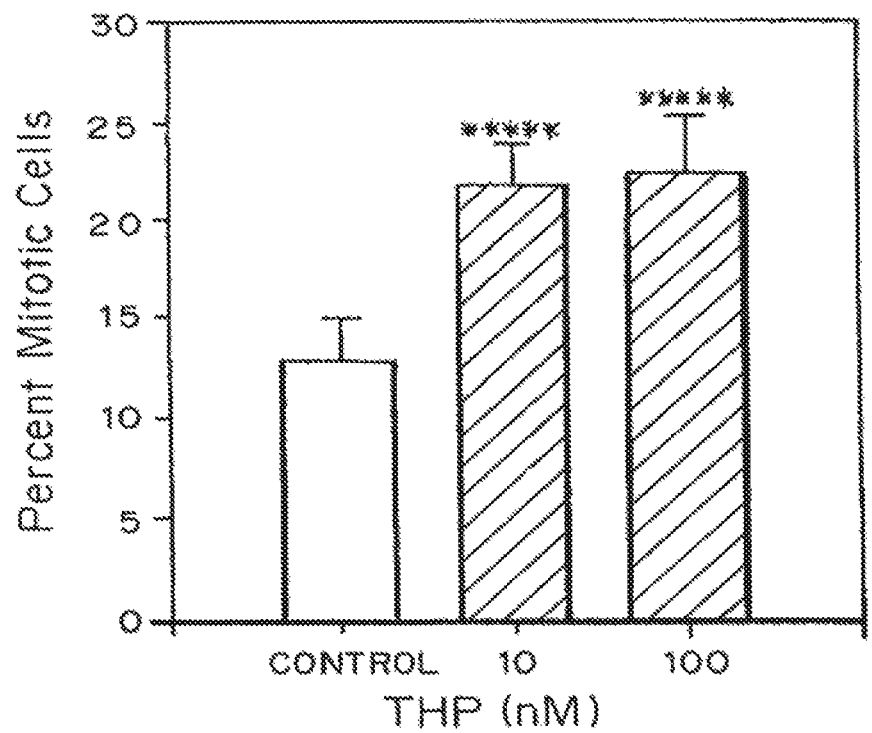
FIG. 2 is a bar graph showing the percent of the total number of hippocampal neural cells exhibiting a mitotic appearance (i.e. a doublet form cell body indicative of mitosis) in control (clear rectangle), or following administration of 10 (nanomolar, nM) or 100 (nanomolar, nM) 3α-hydroxy-5α-pregnan-20-one (THP) (hatched rectangles).

Example 1. The Effect of 3α-Hydroxy-5α-Pregnan-20-One (THP) on Hippocampal Neural Cells Hippocampal neural cells were obtained from an embryonic day 18 rat hippocampus. The samples contained approximately 12,000 neurons/sample. The sample was 95% neuronal. No selection for neuronal subtypes was conducted. Hippocampal neurons were treated with 3α-hydroxy-5α-pregnan-20-one (THP). 3α-hydroxy-5α-pregnan-20-one (THP) was added to two samples containing hippocampal neural cells at a concentration of either 10 nanomolar (nM) and 100 nanomolar (nM). The cells were incubated for 24 hrs at 37° C. Neurons were grown in a defined medium, Neurobasal+B27 supplement in the absence (control) or presence of THP or other test molecule (experimental). The samples with added THP were compared with a control sample containing only hippocampal neural cells. Changes in the mitotic appearance of the neural cells were observed. A mitotic appearance of a particular neural cell is defined as a doublet form in the cell body of the neural cell. The doublet form is indicative of a neural cell undergoing mitosis. A graphic comparison among the three samples studied is shown in FIG. 2. These data reveal that there is an approximate 2 fold increase in the mitotic phenotype of the neural cells studied at either 10 nm THP or 100 nm THP, as compared with the control sample. Data are expressed as percent of the total number of neurons exhibiting mitotic phenotype, mean+SEM, $p<0.01$, *$p<0.001$.

Figure 3:
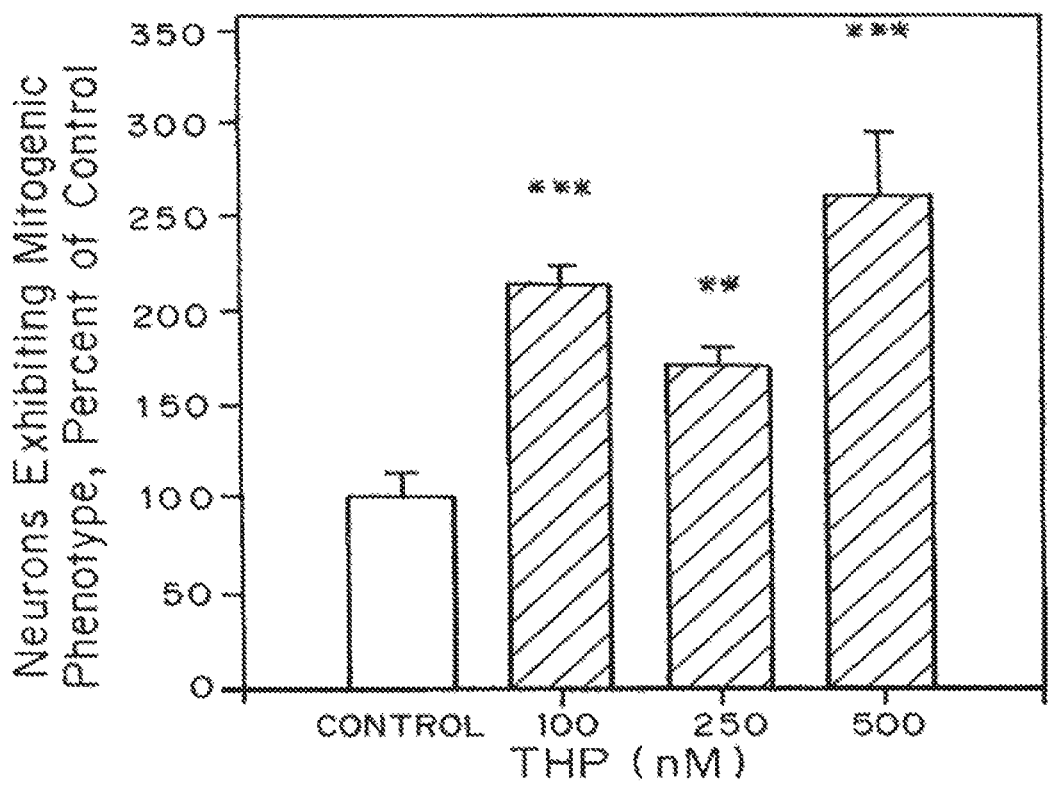
FIG. 3 is a bar graph showing the percent of the hippocampal neurons relative to the number of control neurons with a mitotic appearance (i.e. a doublet form cell body indicative of mitosis) in control (clear rectangle), or following administration of 10 (nanomolar, nM), 100 (nanomolar, nM), 250 (nanomolar, nM), or 500 (nanomolar, nM) 3α-hydroxy-5α-pregnan-20-one (THP) (hatched rectangles).

The experiment described above was repeated only THP was added to three samples containing hippocampal neural cells at a concentration of 100 nanomolar (nM), 250 nM and 500 nM. The samples with added THP were compared with a control sample containing only hippocampal neural cells. A graphic comparison among the four samples studied is shown in FIG. 3. These data reveal that there is an approximate 2-3 fold increase in the mitotic phenotype of the neural cells studied, as compared with the control sample. The greatest effect in induction of the mitotic phenotype was observed at 500 nm THP. Data are expressed as percent of mean+SEM,$p<0.01$, *$p<.001$.

Example 2. Effect of 3α-Hydroxy-5α-Pregnan-20-One (THP) on the Expression of Cell Proliferating Markers THP also was shown to increase the expression of cell proliferating markers. Expression of cell cycle proteins have been successfully used to evaluate cellular proliferation. One such protein is the nuclear proliferation protein, Ki-67, which is expressed during the G1, S, G2, and M phases of the cell cycle, but is not expressed during the Go (resting) phase. Because Ki-67 antigen has a short half-life, it can be used as a marker of actively proliferating cells. Another cell cycle protein is cell division control protein 2 (cdc2) which is a cyclin dependent kinase (also called CDK1) which plays a crucial role in the G1/S and G2/M phase. If THP induces neuronal proliferation, cell proliferation markers should be elevated.

Figure 4:
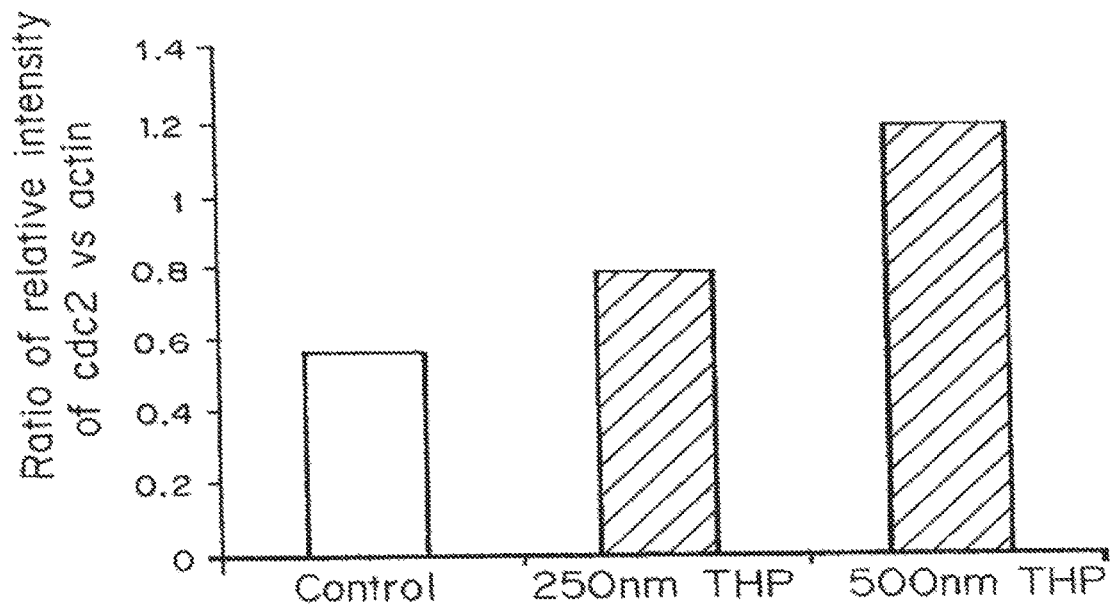
FIG. 4 is a bar graph showing the ratio of relative intensity of the cell division control protein cdc2 and actin in control hippocampal neurons (clear rectangles) and hippocampal neurons treated with 250 (nanomolar, nM), or 500 (nanomolar, nM) 3α-hydroxy-5α-pregnan-20-one (THP). Neurons were collected following 24 hrs of THP exposure.

Hippocampal neurons were treated with THP at a concentration of 250 nM for 72 hours and immunostained with antibodies for the nuclear proliferation marker, ki-67 antigen, which appears yellow. The results indicate that THP induces the expression of the nuclear proliferation marker Ki-67. This is supported by the fact that the cytoplasm of the donor and the daughter cells did not completely separate. The cell cycle protein cdc2 is also observed in a dose dependent fashion (see FIG. 4). As shown in the figure, THP increases expression of cell division control protein 2 (cdc2) in hippocampal neurons.

For this experiment, neurons were collected following 24 hrs of THP exposure. Forty μg protein of the total cell lysate was loaded and separated by 12% SDS-gel using antibody (Ahcom) specifically against cdc2- and analyzed using Un-Scan-It image software (Ilk Scientific Corp.). This figure shows a representative Western blot from one of three different experiments which have the similar results.

Figure 5:
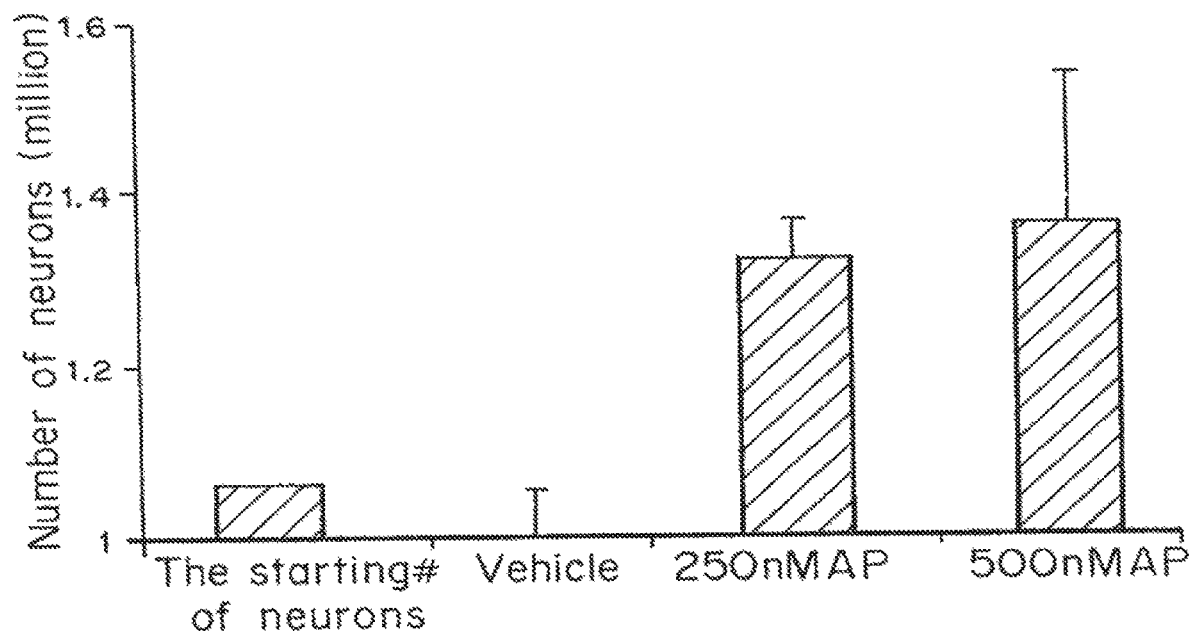
FIG. 5 is a bar graph showing the effect of 3α-hydroxy-5α-pregnan-20-one (THP, nM) on the total number of hippocampal neurons.
Figures 6A, 6B:
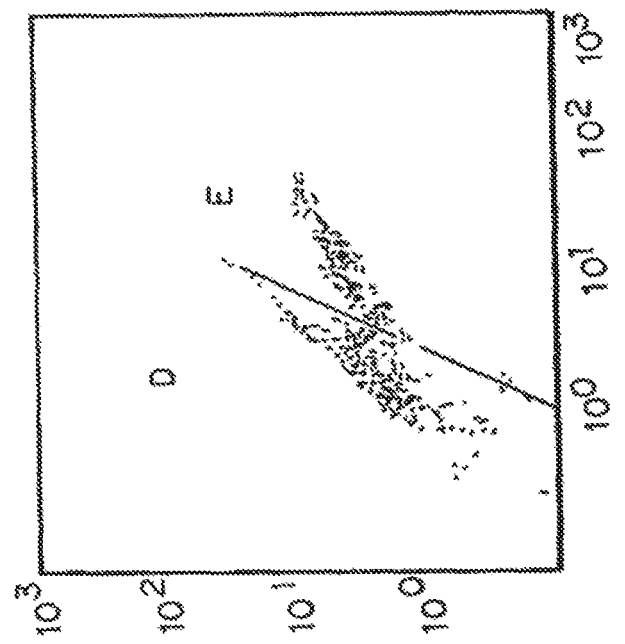
FIGS. 6A-6B are graphs showing the effect of 3α-hydroxy-5α-pregnan-20-one (THP) on neuron number as assessed in MuLV-GFP infected mouse neurons; the effect of THP on HT-22 cells proliferation was detected on MuLV infected cells
Figure 6C:
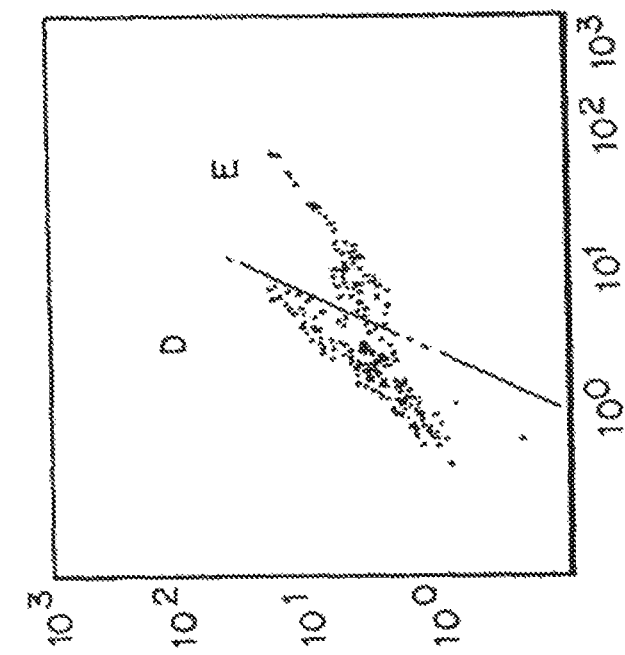

Example 3. Effect of 3α-Hydroxy-5α-Pregnan-20-One (THP) on the Production of Neurons Having determined that THP increases the expression of the cell proliferating markers, a determination was sought as to whether the increase in cell proliferation markers translated into an increase in neuronal number. It was found that THP induced neuronal proliferation by increasing the total cell number and the dividing speed. As shown in FIG. 5, THP increased the neuron number by approximately 30%. These results are highly consistent across different experiments and are also comparable to the results obtained using the mouse hippocampal neuron cell line (HT-22) (FIGS. 6A-6C (Example 12)). As shown in FIGS. 6A-6C, THP increases neuron number as assessed in MuLV-GFP infected mouse neurons. The effect of THP on HT-22 cells proliferation was detected on MuLV infected cells. FIG. 6A shows the FACS profile of the vehicle. FIG. 6B shows the FACS profile of THP treated MuLV-GFP infected cells.

FIG. 6C summarizes the FACS results. V=vehicle; THP (250 nM). THP treatment increased the dividing cell number 22% as determined by fluorescent associated cell sorting (FACS). Therefore, the data demonstrate that THP can increase the proliferation of neuronal cells either in primary cultured cells or continuous cell lines, from rat and mouse.

Example 4. Effect of 3α-Hydroxy-5α-Pregnan-20-One (THP) on 3H-Thymidine Uptake

Figure 7:
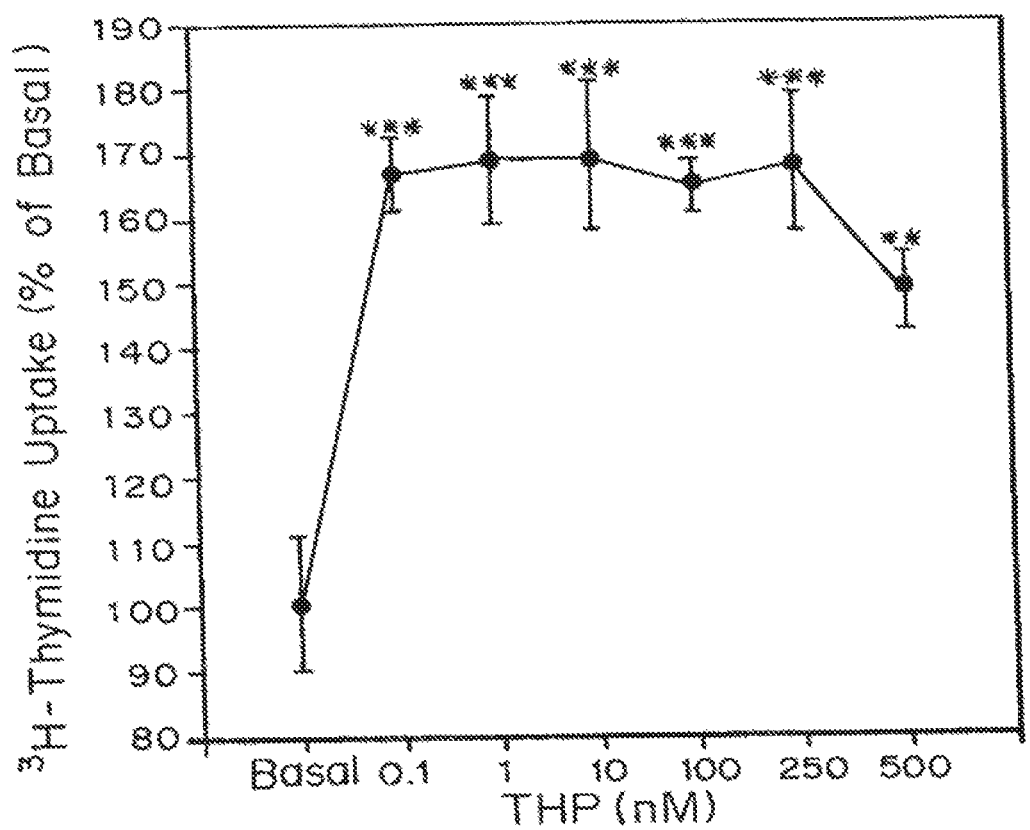
FIG. 7 is a line graph showing 3H-thymidine incorporation (% of Basal) in hippocampal neural cells as a function of 3α-hydroxy-5α-pregnan-20-one (THP, nM) dosage.
Figure 8:
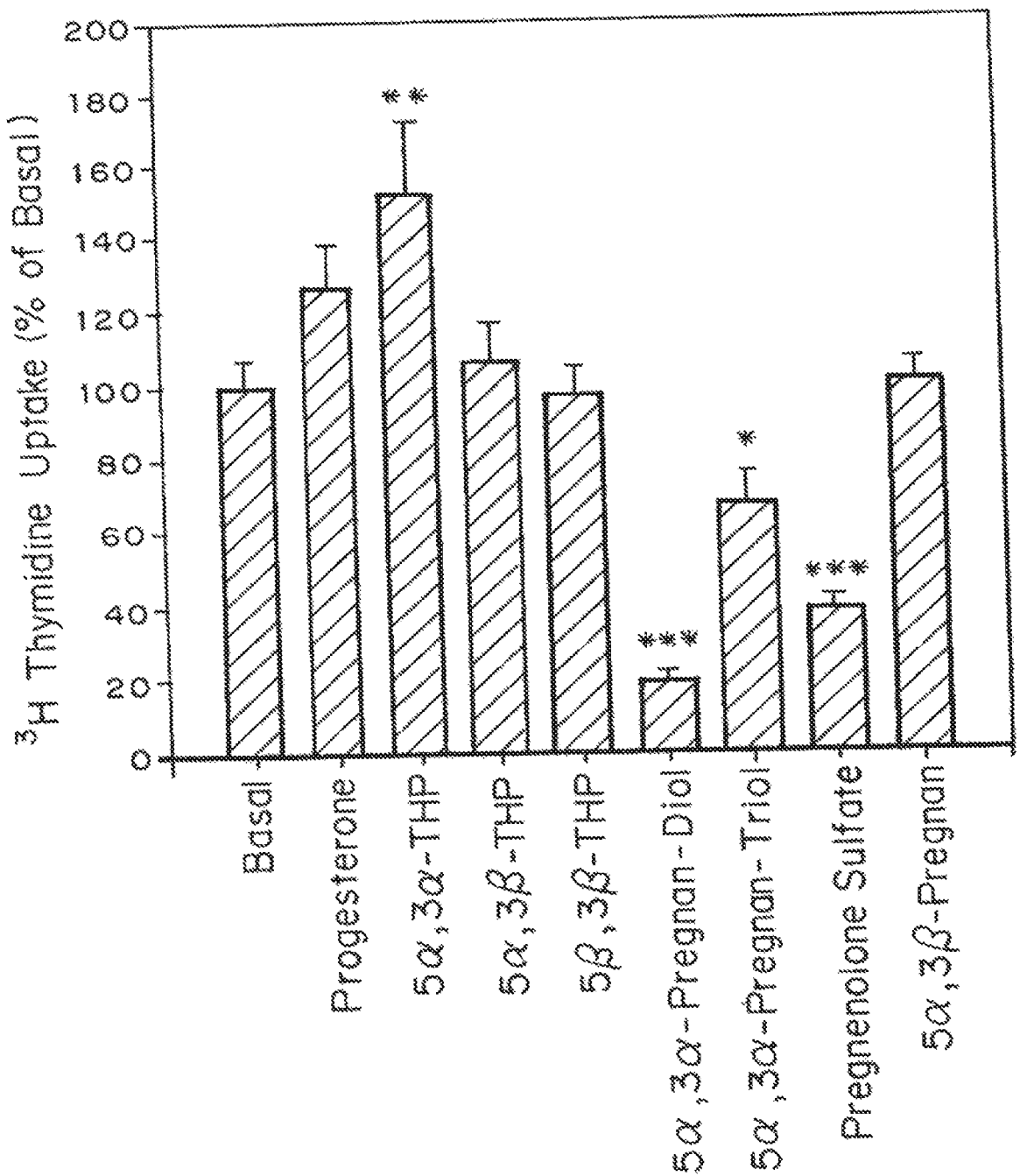
FIG. 8 is a bar graph showing 3H-thymidine incorporation (% of Basal) in hippocampal neural cells treated with 3α-hydroxy-5α-pregnan-20-one (THP), or other structurally or chemically similar steroids.

Biochemical analyses of 3H-thymidine uptake, as a measure of DNA synthesis, were used as the experimental vehicle to confirm the morphological observations described in examples 1 and 2. As shown in FIG. 7, THP induced a 80% increase in 3H-thymidine uptake relative to control (F=12. 31, df 3, 19, p<0.0001) from about 0.1 nm THP to about 250 nm THP. Thus, the range for the neurogenic effect of THP on neural cells is quite is sensitive and quite broad. Furthermore, DNA synthesis is specifically induced in the presence of THP (F=9. 15, df6, 27, p<0.0001), as compared with other structurally and chemically similar steroids, as shown in FIG. 8.

For these experiments, cultured hippocampal neural cells, derived from embryonic day 18 rat fetuses, were allowed to adhere to polylysine coated plastic cover-slips for 40 min in serum containing medium. Following adhesion, neurons were exposed to 1 Ci/ml 3H-thymidine in the presence or absence of 100-500 nM THP and allowed to incubate at 37° C. for 24 hours in the absence or presence of the indicated steroids. Data are expressed as mean+SEM, *p<.05,p<0.01, *p<0.001. The results demonstrated that THP induction of 3H-thymidine incorporation is highly specific. Progesterone induced a modest increase in 3H-thymidine incorporation; however, the stereoisomers of THP, i.e., 5cc, 3ss-THP and 5ss, 3ss-THP, as well as 5α, 3P-pregnen-3-one, showed no effect.

Additionally, 5α,3α-pregnan-diol; 5α,3α-pregnan-triol and pregnenolone sulfate (PS), which are known to increase morphological differentiation, induced a significant decrease in 3H-thymidine incorporation which is consistent with their differentiation effect. The steroid specificity analysis provides evidence for the specificity of THP-induced mitogenesis. Moreover, consistent with this evidence is the observation that differentiation factors have an effect opposite to that of THP in that these agents cause a decrease in 3H-thymidine incorporation.

Figure 9:
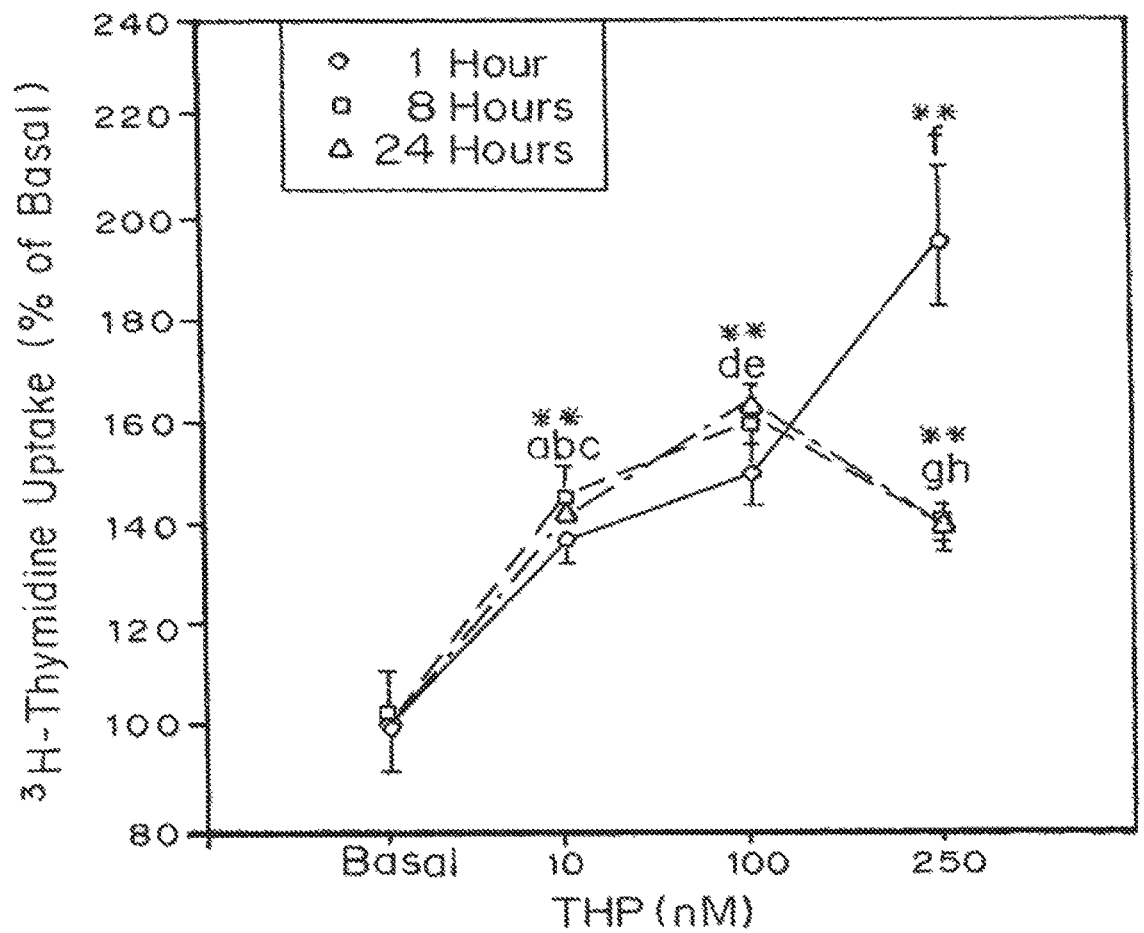
FIG. 9 is a line graph showing depicts the time course of 3α-hydroxy-5α-pregnan-20-one (THP)-induced 3H-thymidine incorporation (% of basal) in hippocampal neural cells as function 3α-hydroxy-5α-pregnan-20-one (THP) dosage (nM) at 1 hour (clear diamond), 8 hour (clear square) and 24 hour (clear triangle) time intervals.

The time course of THP-induced 3H-thymidine incorporation in hippocampal neuronal cells is shown in FIG. 9 where cultured hippocampal nerve cells, derived from embryonic day 18 rat fetuses, were allowed to adhere to polylysine coated plastic cover-slips for 40 min in serum containing medium. Following adhesion, serum containing medium in the presence or absence of 10-250 nM THP plus 1 pCi/ml 3H-thymidine and allowed to incubate at 37 for 1, 8 or 24 hours. Data are expressed as mean±SEM, *p<0.05, p<0.01,*p<0.001.

Figure 10:
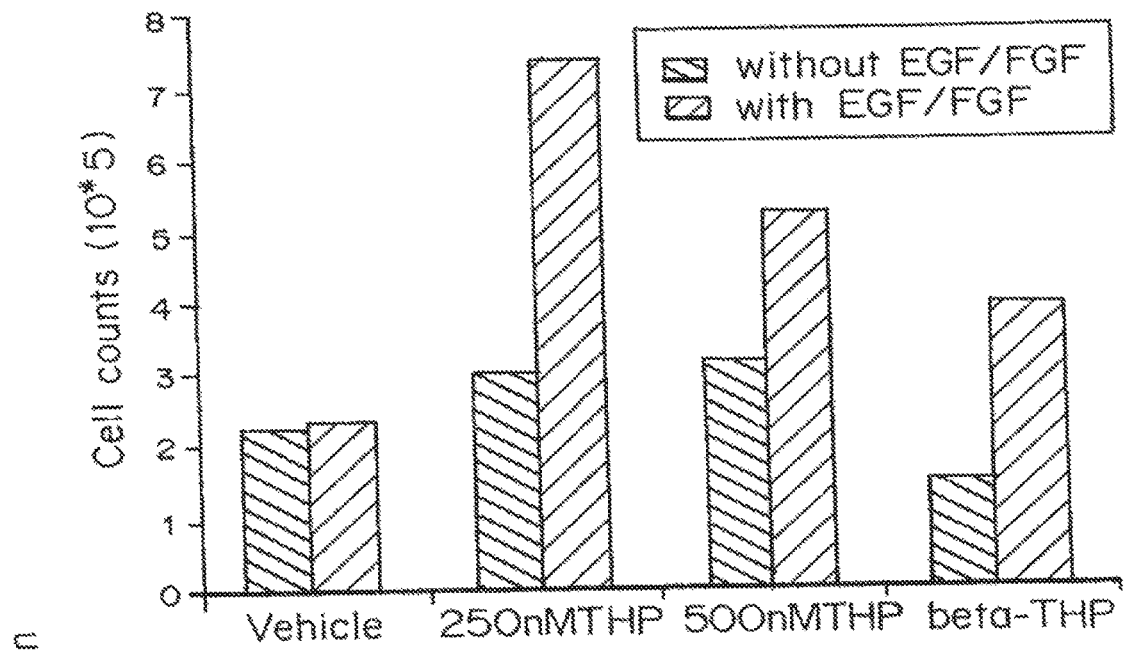
FIG. 10 shows the number of rat neural stem/progenitor cells (cell counts ($10^5$)) from neural spheres (generated from the periventricular area and hippocampus of embryonic day 18 rat embryos) treated with control, 250 nM 3α-hydroxy-5α-pregnan-20-one (THP), 500 nM 3α-hydroxy-5α-pregnan-20-one (THP), or β(THP) with (rectangles hatched from bottom left to top right), or without EGF/FGF (rectangles hatched from top left to bottom right).

Example 5. Effect of
3α-Hydroxy-5α-Pregnan-20-One (THP) on the Production of Neural Stem Cells Experiments to determine whether THP promotes neural stem cells growth were also performed. In FIG. 10, neural spheres were generated from the periventricular are and hippocampus of embryonic day 18 rat embryos. 5 rat embryos were treated with THP alone or with EGF and FGF-2 as mitogens. The approximately third passage of neural spheres were collected and randomly disturbed evenly to each dish. Dishes were treated with reagents as labeled in the absence of progesterone for 36 hours. Cells were then collected and trypsinized in to single cells. The cell numbers were counted blind using a hemacytometer and plotted in Excel.

Figure 11:
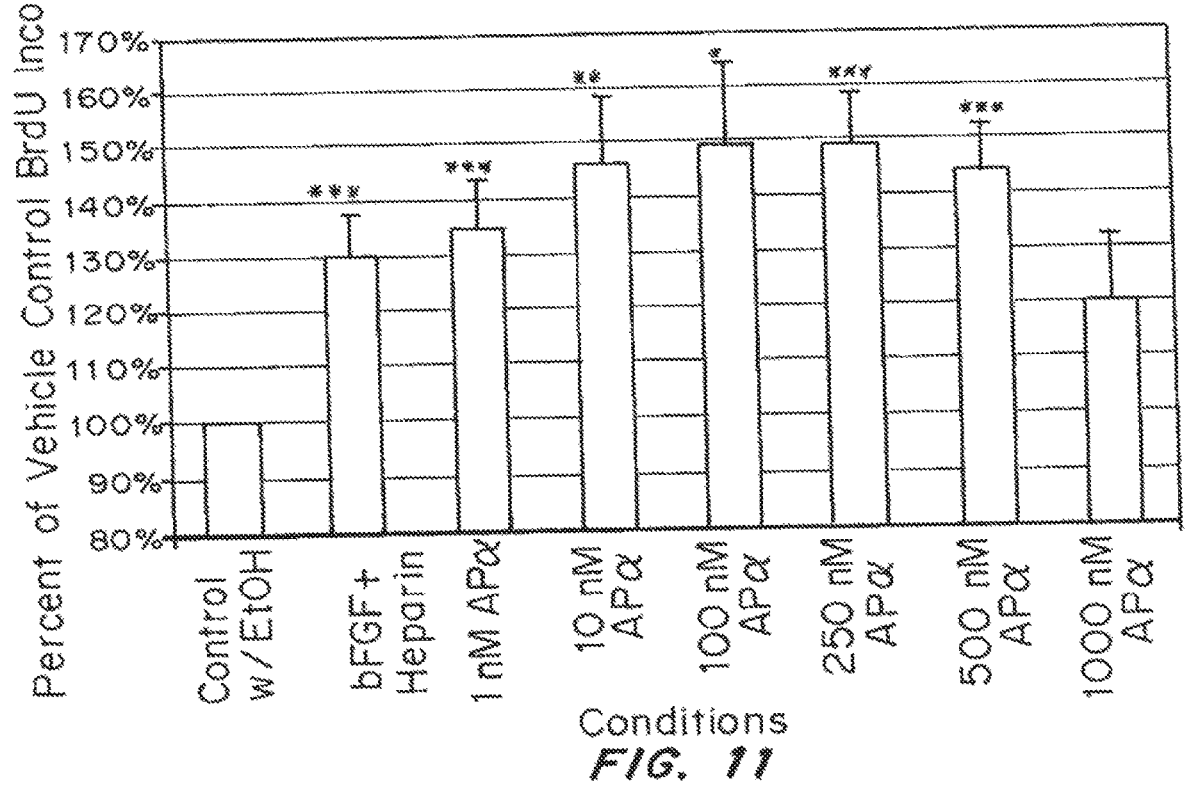
FIG. 11 is a graph showing percent of vehicle control BrdU incorporation in human neural stem cells treated with various concentrations of 3α-hydroxy-5α-pregnan-20-one (APα) (1, 10, 100, 250, 200, 1000 nM) or with bFGF (20 ng/ml)+heparin (511 g/ml).

Another experiment was performed to assess the neurogenic effects of THP administration on human neural stem cells. The results are shown in FIG. 11. In this experiment, neural stem cells derived from human fetal cortex were treated with varying concentrations of THP [1-1000 nM] or with bFGF [20 ng/ml]+heparin [511 g/ml] as a THP positive control. The proliferation marker, BrdU [10 uM] was added simultaneously with test molecules and the cells were incubated at 37° C. for 24 hours. Quantitative Elisa chemiluminescence of BrdU signal was conducted at 24 hrs following addition of substrate and chemiluminescence determined by LMax microplate luminometer (Molecular Devices) (Roche Diagnostics Corp., Cell Proliferation ELISA, BrdU (chemiluminescence). THP at 250 and 500 nM, significantly increased BrDU chemiluminescence relative to vehicle control condition and was consistently greater than the positive control bFGF+heparin. Data are presented as mean±SEM and are derived from three separate experiments.

Example 6. Neural Progenitor Proliferation in Dentate Granular Zone (DGZ) is Deficient in 3 Month Old Male 3×TgAD Mice Prior to Onset of Visible AD Pathology BrdU inmmunohistochemisry (IHC) was preformed on adjacent sections of IHC-labeled for Aβ. Sections were immunostained with BrdU antibody (Novus Biologicals) and imaged using 3I Marianas Imaging System with Zeiss Axiovert 200M interfaced with a Sony ICX-285 CCD CoolSnap HQ camera and Xenon 2-Gal Fast Excitation Source equipped with SlideBook unbiased quantitative stereology software. Results of un-biased quantitative stereological analyses indicate that at 3 months prior to the appearance of markers of Alzheimer's (AD) pathology, the BrdU-positive cell number was significantly lower in the 3×TgAD mouse dentate relative to non-Tg mouse dentate. This finding indicates basal neurogenesis in 3×TgAD mice DGZ is reduced prior to development of overt AD pathology. These results also suggest that the early neurogenic deficits, which were evident prior to visible Aβ and ptau, may contribute to etiology of AD.

Example 7. 3α-Hydroxy-5α-Pregnan-20-One (THP) Reverses the Neurogenic Deficits in 3×TgAD Mice Hippocampal Dentate Gyrus THP increased BrdU incorporation in both non-Tg and 3×TgAD mice. A more pronounced and significant increase was observed in 3×TgAD mice with the greatest increase, 55+18% greater vs vehicle control group, which occurred at 10 mg/kg BW. Analysis of total number of cells generated indicated that THP restored proliferation to that of normal nontransgenic mice thereby reversing the neurogenic deficit.

Cortices from brain hemisection of mice treated with THP or vehicle were collected at time of sacrifice for measurement of THP by GC/MS. Plasma was also collected at time of sacrifice. Three-month-old male non-Tg and 3×TgAD mice were subcutaneously injected with THP (1, 10, and 20 mg/kg BW) or vehicle (0.1% ethanol in PBS, n=4 in each group). The mice were sacrificed 24 hours later. THP concentration in plasma and brain were measured by GC/MS. THP was detectable in plasma and cortex in a linear dose dependent manner. An interesting finding is that 3×TgAD mice exhibited a consistently lower level of THP in both plasma and cortex relative to nontransgenic THP treated mice. In the 3×TgAD mouse cortex, a 10 mg/kg dose of THP results in a cortical level of 20 ng/g protein 24 hrs post injection.

Example 8. 3α-Hydroxy-5α-Pregnan-20-One (THP) Increased Expression of Proliferating Cell Nuclear Antigen (PCNA) and Cyclin Dependent Kinase 1 (CDK1/Cdc2) in the Hippocampus of 3×TgAD and Non-Tg Mice We sought to identify a medium throughput marker of proliferation that would allow us to detect proliferative efficacy in hippocampus with greater speed relative to unbiased stereological analyses. Thus, we conducted biochemical analyses in parallel to the stereological analyses to determine whether two well defined cell cycle related proteins, PCNA and CDK1/cdc2, would serve as biochemical indicators of proliferation in the hippocampus.

Brain samples derived from the same brains that underwent unbiased stereological analysis and GC/MC for THP detection were also analyzed by real-time RT-PCR and Western blot for expression of PCNA and CDK1 mRNA and protein. Results of these analyses indicate that THP induced a dose-dependent increase in PCNA mRNA in a pattern consistent with the stereological results in the 3xTgAD mice. Results of Western blot analyses indicate that 10 mg/kg THP induced greater PCNA and CDK1 protein expression in the hippocampi of 3xTgAD relative to the non-Tg mice which is consistent with the stereological data. Importantly, these data indicate that either mRNA or protein expression of PCNA can serve as an indicator of proliferation within the hippocampus to permit a first pass medium throughput analysis of the proliferative efficacy of THP across multiple doses and topical or transdermal formulations.

Figure 12A:
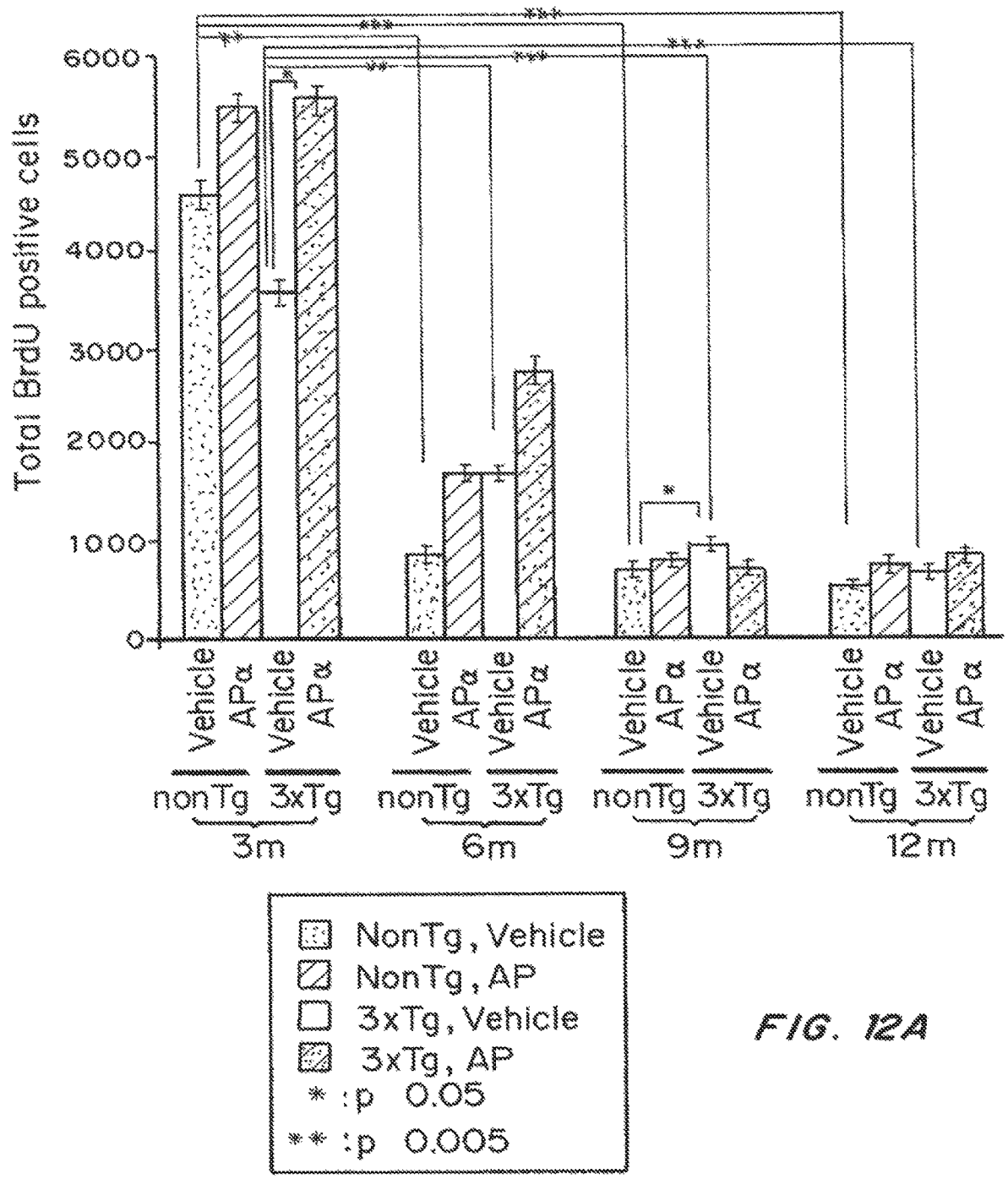
Figure 12B:
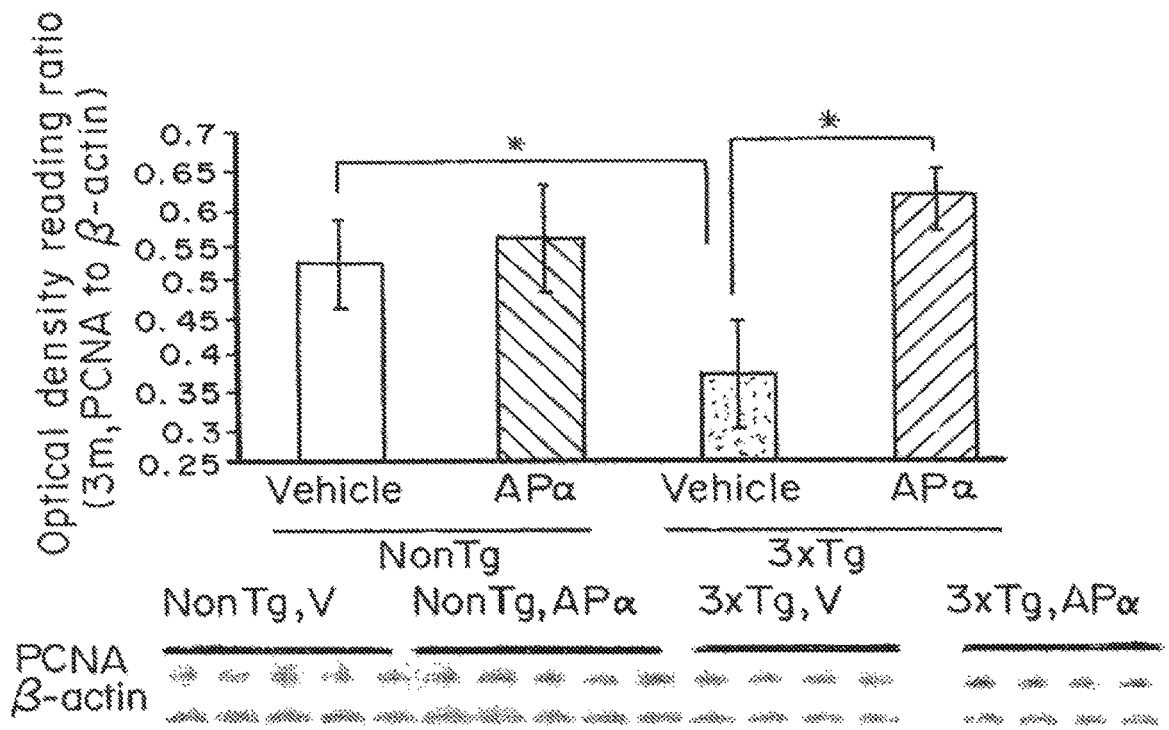
Figure 12C:
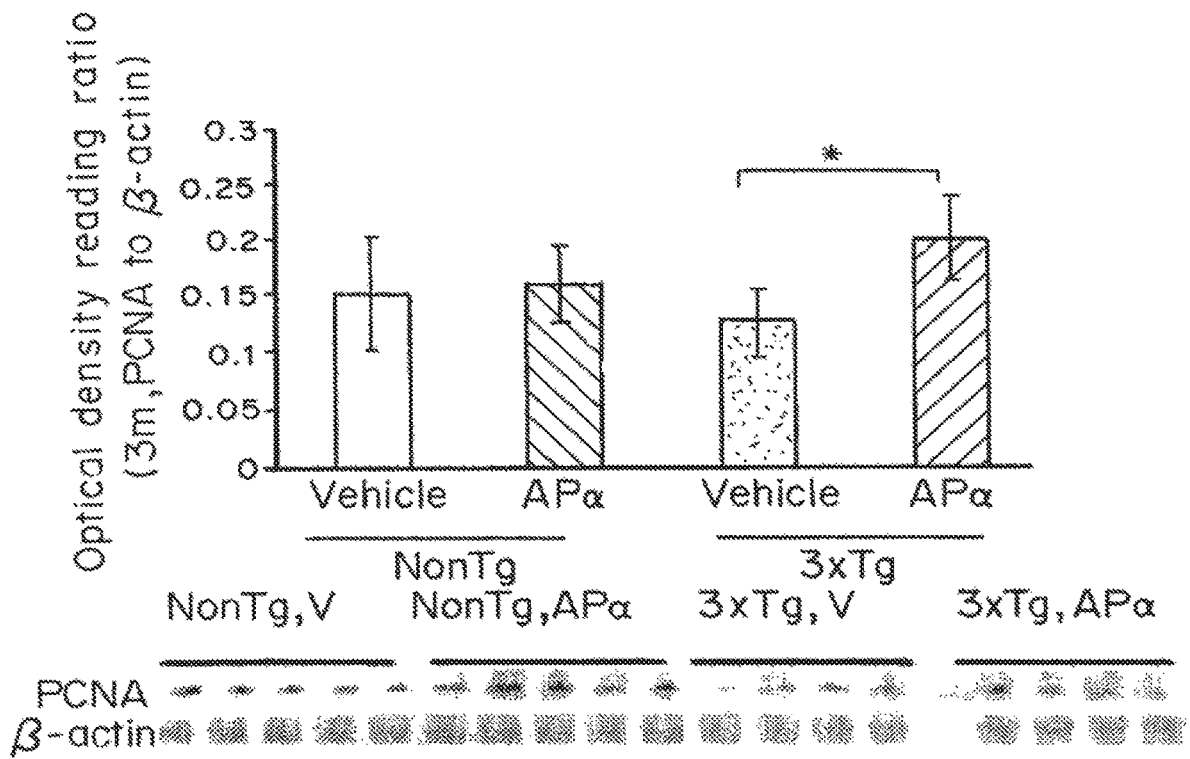

FIG. 12A shows the stereological analyses of mouse dentate gyrus subgranular zone (SGZ) performed 24 hours following one subcutaneous dose of THP (10 mg/kg) or vehicle control. Total BrdU labeled cells were quantified for 3, 6, 9, and 12 months non-Tg and 3xTgAD male mice. The serial brain sections were collected to analyze the effects of THP on BrdU incorporation by unbiased stereological analysis. Data are represented as mean±SEM (n≥4 in each group). Data demonstrated that THP-induced increase in proliferation reversed the neurogenic deficit of the 3xTgAD mouse SGZ and restored normal levels of neurogenesis. PCNA, an S-phase cell cycle marker, was increased in THP compared to vehicle control in 3xTgAD mice in three month (FIG. 12B) and six month (FIG. 12C) mice as shown by immunoblot. FIG. 12D is a graph of the PCNA immunoblot data which shows that the basal level (vehicle) of PCNA expression decreases with age and pathology in 3xTgAD mice hippocampus compared to 3 month background strain non-Tg (positive control).

Aging Differently Affects Neurogenic Activities in 3xTgAD and Control Mice in Hippocampal Subgranular Zone (SGZ)

Results showed that 21 days after THP administration an increase in BrdU+ cell number was observed at all ages, indicating an increase in neurogenesis after THP treatment. Neurogenesis includes cell proliferation and cell survival; it is thus important to determine whether increased neurogenesis after THP treatment is due to increased cell proliferation or increased cell survival. To decipher the THP effect, it is critical to first determine the basal level of cell proliferation in those animals. Hence, a comparative analysis of BrdU incorporation was conducted in both 3xTgAD and non-Tg mice at 6, 9, 12-months of age to determine basal level of cell proliferation in the SGZ. The distribution of the BrdU-positive (BrdU+) cells within the 3xTgAD and non-Tg mice was consistent with that observed in both rat and mouse dentate gyrus. Interestingly, two distinct populations of BrdU+ cells were observed in both 3xTgAD and non-Tg mice across all three ages: normal BrdU+ cells with regular cell shape and even BrdU staining representing normal proliferating cells, and irregular BrdU+ cells with either condensed or fragmented nuclei. The later were consistent with the observations of pyknotic cells reported by other groups, and are referred to as pyknotic BrdU+ cells.

Results of unbiased quantitative stereological analyses indicated that unlike 3-months-old mice, there was no significant difference in proliferating cell number between non-Tg and 3xTgAD mice at 6, 9, and 12-months of age ($p=0.27$, $p=0.39$ and $p=0.22$ respectively; N=6-10). Basal level proliferations in non-Tg mice at 6, 9, 12-months were 792.0±284.41, 456.0±226.42, 456.0±153.68, respectively while the basal level proliferations in 3xTgAD mice at 6, 9, 12-months were 600.0±117.23, 537.6±168.84, 326.4±81.21, respectively. Consistent with findings reported in the literature, both mouse genotypes showed a trend of age-dependent decline in normal BrdU+ cell number; while the only statistical significant was observed between 6- and 12-month-old 3xTg-AD mice ($p<0.05$, N=6-10), consistent with previous western blot result on PCNA expression level. Notably, significant reduction in basal level proliferation was found between 3- and 6-months old animals in both mouse genotypes, with 3-months-old non-Tg mice showing a basal level of 4560±1089 BrdU+ cells and 3xTgAD mice showing 2625±426 BrdU+ cells ($p<0.05$, N=6-10).

In contrast, analysis from the pyknotic cell population indicated that 3xTgAD mice exhibited a significant higher number of pyknotic cells at 6-months of age, almost 9-folds higher than that of age-matched non-Tg mice. Pyknotic BrdU+ cell counts in non-Tg mice at 6, 9, 12-months of age were 48.0±48.00, 192.0±81.13, 48.0±31.42, respectively. On the other hand, pyknotic BrdU+ cell counts in 3xTgAD mice at 6, 9, 12-months of age were 456.0±125.37, 172.8±66.82, 96.0±51.60, respectively. The pyknotic cell number in 3xTgAD mice dropped to a level comparable to non-Tg animals at older ages (9&12 months) and no significant difference were found between the two mouse genotypes. The findings of abnormally high pyknotic cell population indicated that in addition to reduced basal cell proliferation, 3xTgAD mice might also exhibit varied forms of neurogenic deficiencies at different ages including cell survival and cell death.

THP Specifically Reverses the Neurogenic Deficit in 3xTgAD Mice and had No Effect on Non-Tg Mice To decipher the THP effect in neurogenesis, cell proliferation assessment experiments were conducted. Following animal sacrifice and brain section staining, unbiased stereology was conducted in both non-Tg and 3xTgAD mice at three different ages. Consistent with previous results that no significant differences were found in basal level cell proliferation between non-Tg and 3xTgAD at all ages, THP showed no significant effect on cell proliferation in both mouse genotypes. Specifically, THP had no effect on cell proliferation in non-Tg mice at all ages ($p=0.40$, $p=0.27$, and $p=0.35$. respectively). In 3xTgAD mice, THP showed no significant effect in cell proliferation although a trend was observed that THP tended to bring the cell proliferation level more comparable to that of non-Tg mice ($p=0.07$, $p=0.39$ and $p=0.32$ respectively).

In contrast, THP had a significant effect on the pyknotic cell population in both mouse genotypes at 6-months of age, when a dramatic difference was observed in the basal level cell pyknosis. While 3xTgAD mice exhibited a 9-fold higher basal level pyknosis, treatment with APa significantly reduced it to the level of non-Tg mice, the pyknotic BrdU+ cell count before and after THP treatment were 456.0±125.36 and 48.0±48.00, respectively. Surprisingly, THP treatment in non-Tg mice significantly increased the pyknotic BrdU+ cell count. The numbers before and after THP treatment were 48.0±48.00 and 576.0±185.49, respectively. The increase in pyknotic cell population was unexpected; however it could be explained by a "proliferative sensor" mechanism which tightly controls cell proliferation in normal animals. At 9- and 12-months of age, no difference was observed between vehicle- and THP-treated groups in both non-Tg and 3xTgAD mice.

To confirm the stereological analyses results, Western blot analyses of cell proliferation marker PCNA were carried out using samples derived from the same brains which underwent unbiased stereological analysis. PCNA, or Proliferating Cell Nuclear Antigen, is a protein that acts as a processivity factor for DNA polymerase delta subunit in eukaryotic cells and was induced in vitro by THP in cultured rat hippocampal progenitor cells. Consistent with stereological analyses, results of western blot indicated that no significant differences in basal PCNA expression level exist between non-Tg and 3×TgAD mice at 6- and 9-months of age (p=0.40 and p=0.32, respectively; N=5). Treatment with THP did not significantly affect PCNA expression in either mouse genotype, although a trend was observed that APα tended to bring the PCNA expression level more comparable to that of non-Tg mice.

Together with our earlier findings, these results indicated that THP could specifically modulate the neurogenic activities (mainly cell proliferation) in 3×TgAD mice, and this effect will only be shown when there is an intrinsic deficiency/abnormality in these mice. Aα has limited effect on the neurogenic activities in non-Tg mice, indicating that the effect of THP is specifically related to the Alzheimer's disease transgenes. Further, regardless of the age of the mice, THP tends to bring the neurogenic activity level in 3×TgAD mice more comparable to that of non-Tg mice.

Example 9. Phenotype of Newly Formed Cells in 3α-Hydroxy-5α-Pregnan-20-One (THP) Treated 3×TgAD Mouse Dentate Gyrus are Neuronal and Astrocytic To verify the phenotype of the BrdU-positive cells in vivo, double or triple immunolabeling of BrdU-positive cells with neuronal markers Tuj1, MAP2, NeuN and astrocyte marker, GFAP, were performed in the 3×TgAD mouse hippocampi, which were treated with 10 mg/kg THP at 3 months and survived for 3-12 weeks. Under lower magnification, the majority of the BrdU-positive cells are observed in the SGZ or Hilus. The distribution of the newly formed cells is consistent with that observed by previous studies. Imaging showed co-localization of BrdU in NeuN positive cells, indicating that newly generated cells exhibit an early neuronal phenotype. Imaging also showed a newly formed granular cell layer integrated neuron with nuclear co-localization of BrdU and NeuN and a glial cell with BrdU positive nuclear and GFAP positive cytosol.

Neurons and glia are generated throughout adulthood from proliferating cells in two regions of the rat brain, the subventricular zone (SVZ) and the hippocampal SGZ. We stereologically analyzed the SVZ from 3×TgAD mice in the control and 10 mg/kg THP groups. Results of these analyses indicated that THP induced a 58% increase in BrdU-positive cells relative to the 3×TgAD untreated group. These data indicate THP increase BrdU incorporation in both SVZ and SGZ, but was more pronounced in SVZ.

Example 10. 3α-Hydroxy-5α-Pregnan-20-One (THP) Reversed the Learning Deficits of 3×TgAD Mice To determine if there was a functional consequence of THP-induced neurogenesis, the impact of THP on both the learning and memory of a behavioral task shown to be dependent upon the generation of new neurons in the dentate gyrus, delayed trace conditioning was assessed. 3×TgAD and non-Tg background mice were prepared for behavioral testing and received a single s.c. injection of THP (10 mg/kg once) or vehicle 7 days prior to start of the learning trial. After injection, mice were housed for 7 days before the training process started. The rationale for the 7 day interim between exposure to THP and the start of the behavioral experiment was to allow time for the proliferation, migration and integration of newly generated neurons into the dentate gyrus.

Figure 13F:
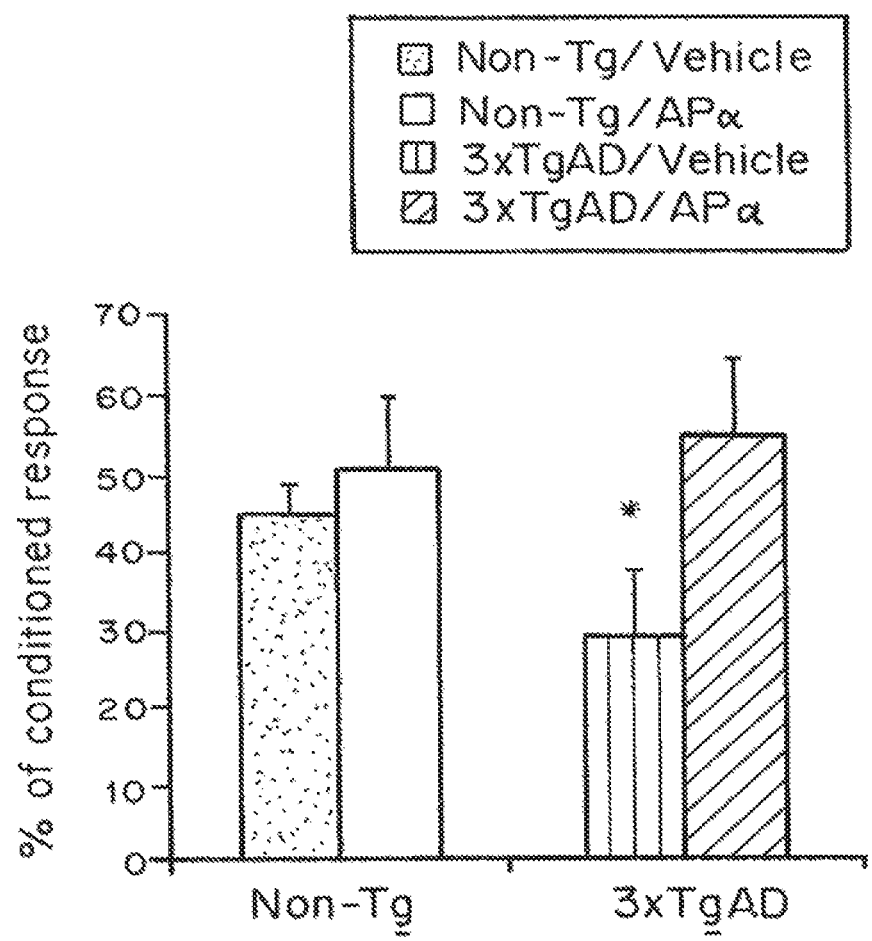
FIG. 13F is a bar graph showing the results of the memory tests 9 days following the learning trial in Non-Tg and 3×TgAD mice with or without 3α-hydroxy-5α-pregnan-20-one (APα) treatment. Data is represented as % of conditioned response in Non-Tg/vehicle treated, Non-Tg/APα treated, 3×TgAD/vehicle treated, 3×TgAD/APα treated (from left to right across the x-axis) mice.

Following the 7 day interim period, the behavioral testing commenced with a 5 day (2×30 trials/day) training learning phase to assess rate and magnitude learning performance. After the learning trial, mice were returned to their home cage for another 9 day period and subsequently tested for memory of the learned association. Paired trace eyeblink paradigm: In each trial, mice were first exposed to a conditioned stimulation of a 85 dB tone for 250 ms; followed by a 250 ms delay (no stimuli), followed by the unconditioned 60 Hz shock for 100 ms. Introduction of the 250 ms delay between the conditioned and unconditioned stimuli requires the hippocampus to acquire the learned association between tone and shock. Unpaired paradigm: The unpaired diagram (no conditioned) was applied to serve as control for conditioned trace eye blink experiment. The experimental diagram is shown in FIG. 13A. The sequences of conditioned stimuli and the unconditioned shock were applied randomly. The results are shown in FIGS. 13B-13F.

The results of the 5 days training are shown in FIG. 13B. The data indicate that at 3 months, 3×TgAD mice exhibit a learning deficit relative to the performance of normal non-Tg mice (p=0.038, FIG. 13C). In the normal high functioning non-Tg mice, with a concomitant high level of neurogenesis, THP did not augment the learning performance (p=0.97). In contrast, THP significantly increased the learning performance of 3×TgAD mice (p=0.04) to a level comparable to non-Tg mice such that the performance of THP treated 3×TgAD mice was not statistically different from the normal non-Tg mouse (p=0.87, FIG. 13E).

THP Reversed the Memory Deficits of 3×TgAD Mice

The results of the memory test are shown in FIG. 13F. Nine days following the learning trial, mice were tested for memory of the learned association. Non-Tg mice exhibited slightly less than 50% of the conditioned response compared to a 28% response rate of 3×TgAD mice. THP did not significantly augment the memory performance of non-Tg mice. However, THP treated 3×TgAD mice exhibited a significant increase in memory to a level comparable to the normal non-Tg mice. Multivariant ANOVA analysis indicated significant differences for learning and memory in genotype (p=0.004) and days of training (0.04). No interaction occurred between days of training and genotype (p=0.997). Results of the behavioral analyses indicate that AP α enhanced the rate of learning in 3×TgAD mice, increased magnitude of the learning performance and reversed the memory deficit of 3×TgAD mice.

THP Reverses Learning and Memory Deficits in Aged 3×TgAD Mice 3, 6, 9, and 12 month aged mice were tested by trace eye-blinking conditioning following a single dose of THP (10 mg/kg). The results are shown in FIG. 14. Day 5 was a measure of learning (black bars) and day 14 was a measure of memory (white bars). A significant effect of THP was observed in 3 month aged mice (p<0.05).

Figure 14A:
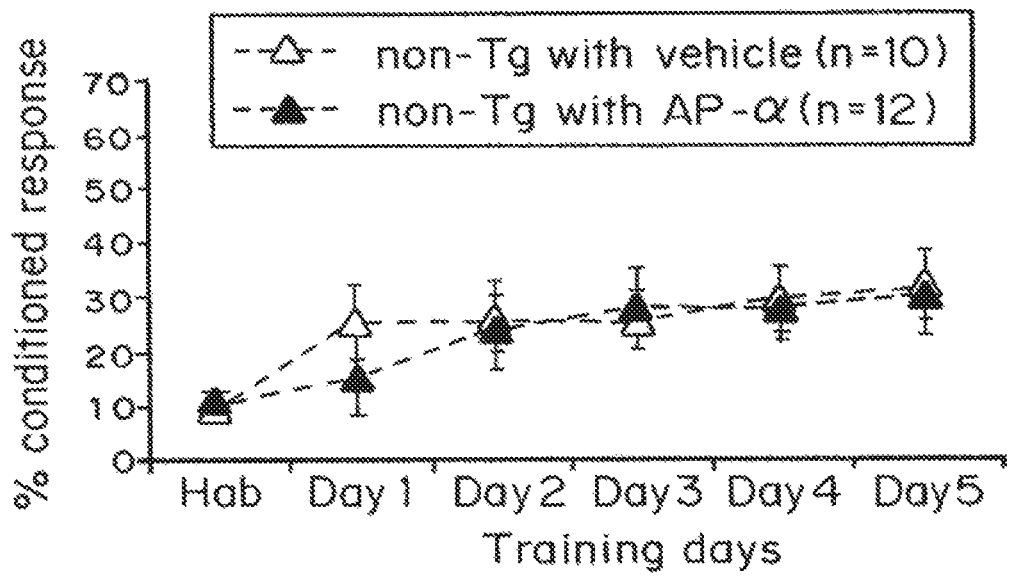
FIG. 14A is a bar graph showing trace eye-blinking conditioning (% conditioned response) as a function of training days for 6 month old non-Tg mice treated with vehicle (solid line) or 10 mg/kg 3α-hydroxy-5α-pregnan-20-one (APα) (dashed line).
Figure 14B:
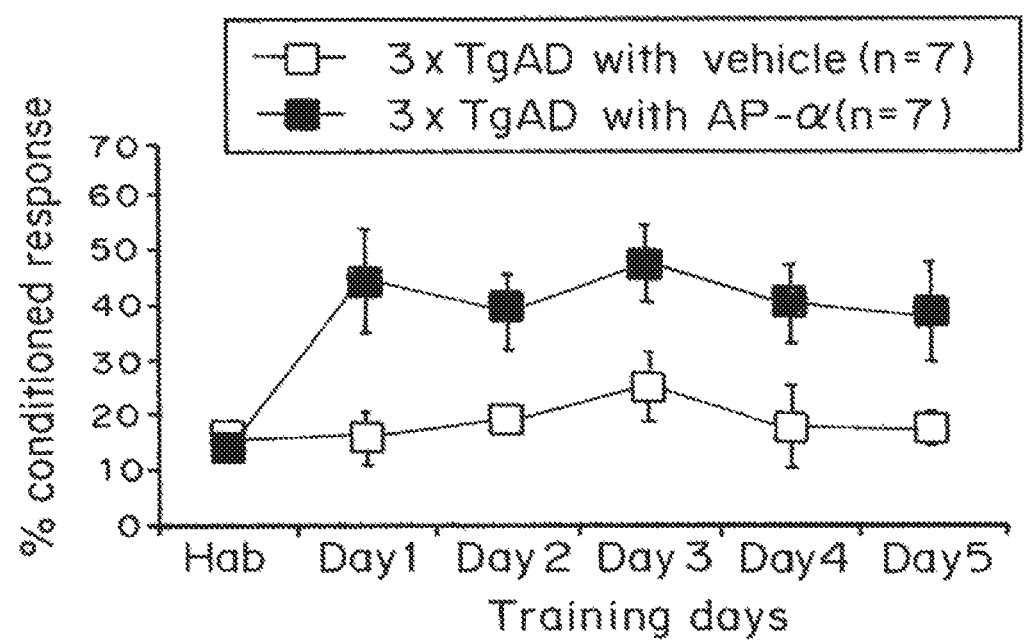
FIG. 14B is a bar graph showing trace eye-blinking conditioning (% conditioned response) as a function of training days for 6 month old 3×TgAD mice treated with vehicle (bottom line) or 10 mg/kg 3α-hydroxy-5α-pregnan-20-one (APα) (top line).
Figure 14C:
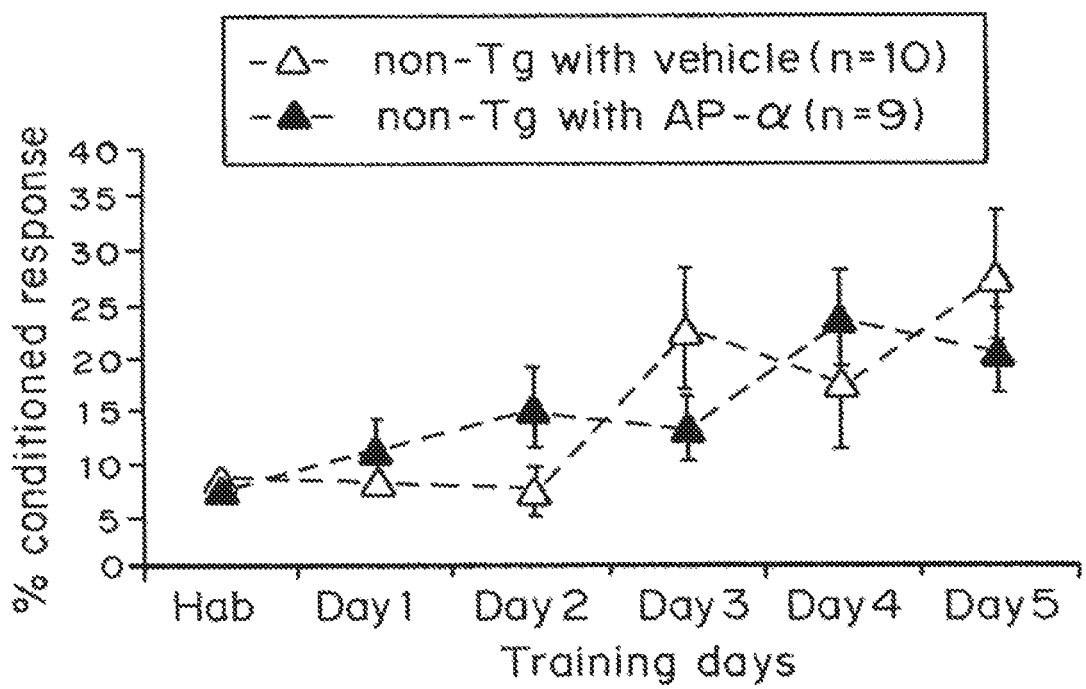
FIG. 14C is a bar graph showing trace eye-blinking conditioning (% conditioned response) as a function of training days for 9 month old non-Tg mice treated with vehicle (solid line) or 10 mg/kg 3α-hydroxy-5α-pregnan-20-one (APα) (dashed line).

FIGS. 14A and 14B show significant effects of THP in 6 month-age mice (P<0.01). The non-Tg group showed a modest level of learning (highest level: 31.3±6.1%) and THP did not augment the learning. The 3×TgAD group showed a reduced basal level of learning when compared to the non-Tg group (but not significant). THP treatment significantly increased both the rate of learning and the highest CR % compared to vehicle-treated 3×TgAD mice, and the final level was comparable to the non-Tg group. THP significantly enhanced the memory retention in 6-month old 3×TgAD mice and showed no effect on the age-matched non-Tg mice. THP-treated non-Tg mice achieved a maximal conditioned response rate of 30.4±7.7% which was not statistically different than vehicle-treated (F(1, 20)=0.010; p>0.05). There was no significant difference observed during the course of training within the vehicle-treated and THP-treated groups (F(1, 108)=0.292; p>0.05). Learning performance was mirrored in their memory performance 9 days post learning phase which was not statistically different than vehicle-treated non-Tg mice (F(1, 16)=0.038; p>0.05).

In contrast, THP significantly increased learning performance of 6-months-old 3×TgAD mice from a basal learning level of 17.4±3.3% to 39.2±9.2% (F(1, 12)=4.943; p<0.05) at the end of training. During the entire course of training, APβ-treated 3×TgAD mice performed significantly better than vehicle-treated mice (F(1, 68)=31.072; p<0.000001) THP-treated 3×TgAD mice performed comparable to the vehicle-treated non-Tg mice at the end of the training (F(1, 15)=0.538; p>0.05). THP also significantly increased the retention of the conditioned response rate in the memory test conducted 9 days after the acquisition phase in 3×TgAD mice (F(1, 10)=5.560; p<0.05).

FIGS. 14 C and D show significant effects in 9 month-age mice (P<0.001). The non-Tg group showed a modest level of learning (highest level: 31.3±6.1%) and THP did not augment the learning. The 3×TgAD group showed a reduced basal level of learning when compared to non-Tg group. THP treatment significantly increased both the rate of learning and the highest CR % compared to vehicle-treated 3×TgAD mice, and the final level was comparable to the non-Tg group. THP significantly enhanced the memory retention in 9-months-old 3×TgAD mice with no effect on the age-matched non-Tg mice.

FIGS. 14 E and F show the effects in 12 month-age mice. 12-month-old non-Tg mice showed low learning rate and maximum level (highest level: 23.8±5.0%) during the training. Treatment with THP did not significantly alter the learning of non-Tg mice although a positive trend was observed in the initial phase of training. 12-month-old 3×TgAD mice showed almost no learning with the highest levels of learning remaining around 15% at the end of the acquisition phase. THP affected neither the learning rate nor the final levels of learning after 5 days of training. 12-months-old 3×TgAD mice exhibited significant lower memory retention than age-matched non-Tg mice (p<0.05). THP did not affect the retention of the learned responses in both 3×TgAD and non-Tg mice.

Data was also obtained from 15-month age mice. The date is shown in FIGS. 14 G and H. 15-months-old non-Tg mice showed low learning rate and maximum level (highest level: 20.3±3.4%) during the training. Treatment with THP did not significantly alter the learning of non-Tg mice although a trend towards an increase at all time points was observed throughout the training phase with a maximum level of 29.6±5.5%. 15-month-old 3×TgAD mice showed almost no learning with the highest levels of learning around 15% at the beginning of the acquisition phase. THP did not affect the learning rate nor the final levels of learning after 5 days of training.

To determine whether cognitive performance was correlated with survival of neuroprogenitor cells, hippocampi from behavioral test animals were analyzed for total number of BrdU positive cells using fluorescence activated cell sorting (FACS). As BrdU was administered one hour post THP injection at the start of the behavioral experiment, FACS analysis detected the total number of surviving BrdU+ cells and thus can be used as a marker of neural progenitor cells that survived and integrated into the hippocampal neuronal network. In 6-months-old vehicle treated non-Tg mice, BrdU+ cell survival was 2003.6±229.5. In THP-treated non-Tg mice, 2772.2±534.9 BrdU+ cells survived which was not significantly different from vehicle-treated (F(1, 13)=1.142; p>0.05). 6-months-old 3×TgAD mice exhibited a significantly lower number of surviving BrdU+(574.1±136.9) compared to non-Tg mice (F(1, 15)=27.937; p<0.001). THP significantly increased BrdU+ in cell survival (1372.5±326.2) (F(1, 19)=4.069; p=0.05) to promote cell survival by greater than 2 fold in 3×TgAD mice.

At 9-months of age, greater intraneuronal Aβ accumulation is apparent in the hippocampus and in very rare instances Aβ plaques have developed. Similar to the effects in 6-months-old animals, THP reversed the learning and neurogenic deficits of 3×TgAD mice with no effect in non-Tg mice. 9-months-old non-Tg mice were impaired in their learning in the initial phase (first 2 days) but improved to 27.8±6.1% with continuous practice over 5-days of training. Treatment with THP had no significant effect on learning (F(1, 17)=0.915; p>0.05) (final level of learning was 20.6±4.1%) although an enhancing trend was observed in the initial phase. Similarly, no significant effect in the performance was observed in the memory test between vehicle- and THP-treated 9-months-old non-Tg mice (F(1, 16)=0.149; P>0.05). Vehicle-treated 3×TgAD mice showed a deficit in the final level of learning as compared to the vehicle-treated non-Tg mice. Vehicle-treated 9-months-old 3×TgAD mice exhibited almost no learning with a response rate of 12.5±2.4%. Compared to the vehicle-treated group the final learning of THP-treated group was significantly increased (F(1, 25)=4.820; p<0.05) to a level of 23.6±4.0%. Similar to effects observed in 6-months-old 3×TgAD mice, THP significantly increased the learning of 9-months-old 3×TgAD mice during the entire course of training (F(1, 129)=24.837; p<0.00001). The enhancement in learning by THP was not a transient effect as it persisted during the whole acquisition course, and was confirmed by the significantly better memory performance after 9 days relative to vehicle-treated 3×TgAD mice F(1, 24)=5.141; p<0.05). Vehicle-treated 3×TgAD mice showed a significant deficit in the memory test as compared to the vehicle-treated non-Tg mice (F(1, 20)=15.237; p=0.001), which was reversed by treatment with THP. THP-treated 3×TgAD mice performed comparable to vehicle-treated non-Tg mice (F(1, 21)=0.282; p>0.05).

THP induced a significant increase in BrdU+ cell survival in 9-months-old 3×TgAD mice similar to what occurred in the 6-months-old 3×tgAD mice. Vehicle-treated 9-months-old non-Tg mice exhibited survival of BrdU+ cells (2288.2±557.9) which was not significantly different from that of 6-months-old non-Tg mice (F(1, 13)=0.214; p>0.05. In the 9-months-old non-Tg mice, THP had no effect on BrdU+ cell survival (2255.3±662.4) as compared to the vehicle-treated group (F(1, 14)=0.001; p>0.05). In 9-months-old vehicle-treated 3×TgAD mice, BrdU+ cell survival (243.7±30.3) was significantly reduced as compared to vehicle-treated non-Tg mice (F(1, 15)=17.294; p=0.001). THP significantly increased the number of surviving BrdU+ cells to 899.3±313.1 (F(1, 19)=7.234; p<0.05) as compared to the vehicle-treated group. However the treatment with THP in 3×TgAD mice was not able to reverse the levels of BrdU+ cells back to that of vehicle-treated non-Tg mice (F(1, 17)=7.288; p<0.05).

Figure 14D:
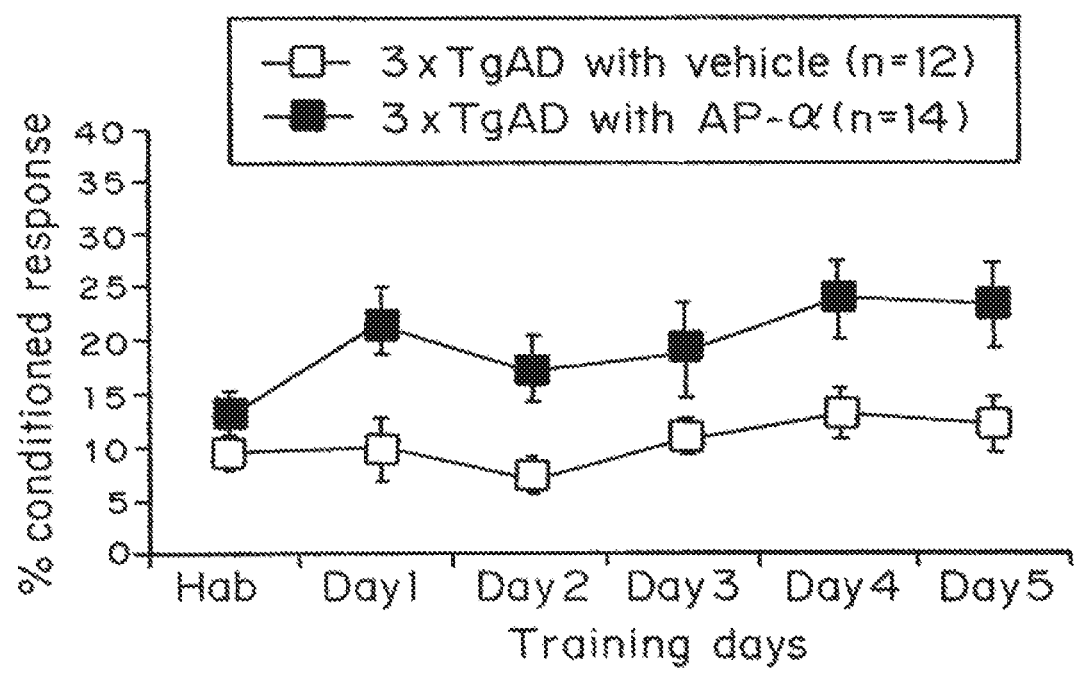
FIG. 14D is a bar graph showing trace eye-blinking conditioning (% conditioned response) as a function of training days for 9 month old 3×TgAD mice treated with vehicle (bottom line) or 10 mg/kg 3α-hydroxy-5α-pregnan-20-one (APα) (top line).
Figure 14E:
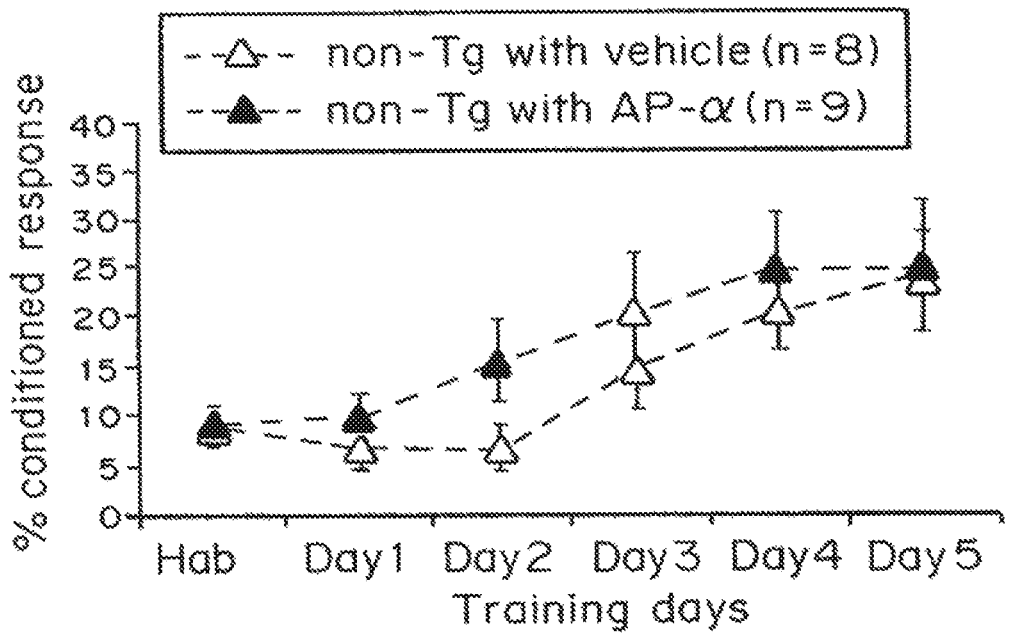
FIG. 14E is a bar graph showing trace eye-blinking conditioning (% conditioned response) as a function of training days for 12 month old non-Tg mice treated with vehicle (solid line) or 10 mg/kg 3α-hydroxy-5α-pregnan-20-one (APα) (dashed line).
Figure 14F:
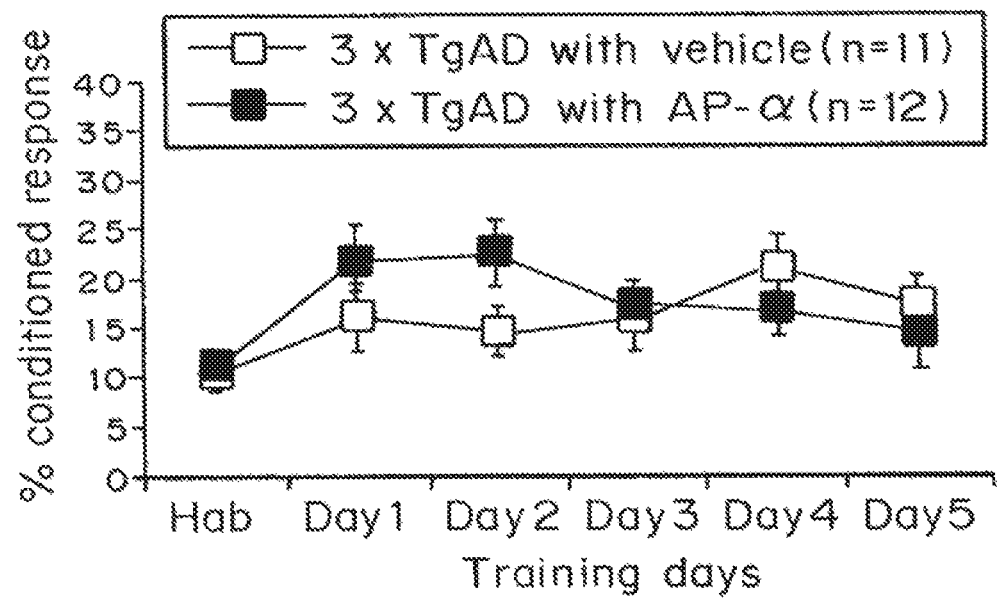
FIG. 14F is a bar graph showing trace eye-blinking conditioning (% conditioned response) as a function of training days for 12 month old 3×TgAD mice treated with vehicle or 10 mg/kg 3α-hydroxy-5α-pregnan-20-one (APα).
Figure 14G:
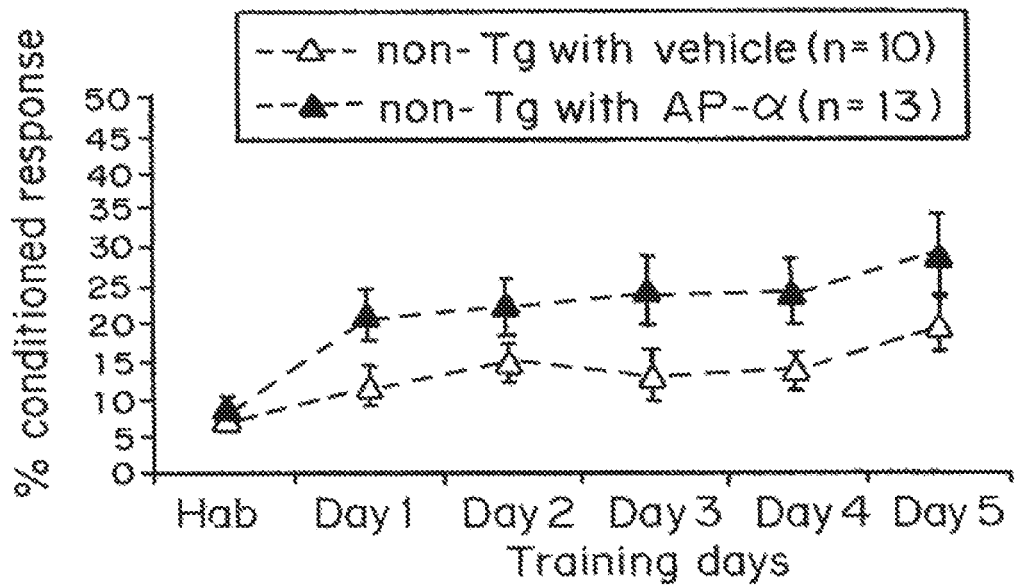
FIG. 14G is a bar graph showing trace eye-blinking conditioning (% conditioned response) as a function of training days for 15 month old non-Tg mice treated with vehicle (solid line) or 10 mg/kg 3α-hydroxy-5α-pregnan-20-one (APα) (dashed line).
Figure 14H:
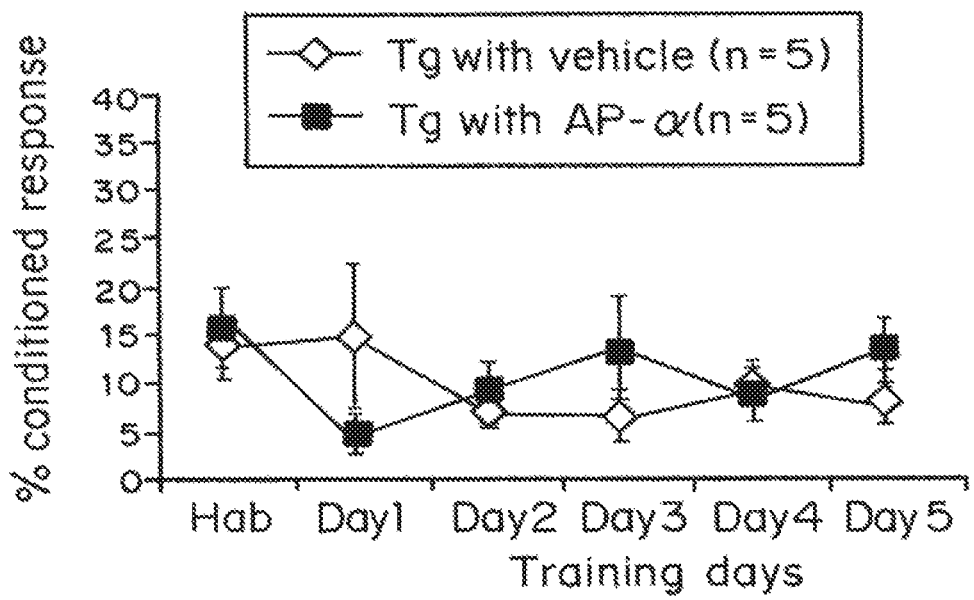
FIG. 14H is a bar graph showing trace eye-blinking conditioning (% conditioned response) as a function of training days for 15 month old 3×TgAD mice treated with vehicle or 10 mg/kg 3α-hydroxy-5α-pregnan-20-one (APα).

At 12-months of age, maximal Aβ intraneuronal accumulation is apparent in the hippocampus and Aβ plaques are widespread. In contrast to the cognitive and neurogenic efficacy of THP in the 6 and 9 months-old 3xTgAD mice, THP treatment in 12-months-old 3xTgAD mice had little effect. In parallel to the loss of efficacy in 3xTgAD mice, emergence of trends towards an THP effect in 12 months-old non-Tg mice was observed. In 12-months-old non-Tg mice a profound decline in associative learning ability was apparent during the initial phase (first 2 days) which subsequently improved to a level of 23.8±5% with 5 days of training. The final level of learning in THP-treated non-Tg mice was 25.4±6%, which was not significantly different from the vehicle-treated group. THP-treated non-Tg mice did not show a significant increase in their learning during the course of training as compared to the vehicle-treated group (F(1, 83)=2.449; p>0.05). THP-treated non-Tg mice showed a positive trend towards increased learning on day 2 as compared to the vehicle-treated group but it was not significant (F(1, 15)=3.750; p>0.05). THP-treated mice showed a modest improved memory performance which was not significantly better than vehicle-treated group (F(1, 15)=1.115; p>0.05). Vehicle-treated 3xTgAD mice showed a deficit in the final level of learning as compared to the vehicle-treated non-Tg mice. Vehicle-treated 12-months-old 3xTgAD mice exhibited almost no learning with a final response rate of 17.5±2.6% (FIG. 14D). Compared to the vehicle-treated group the final learning of THP-treated group was not significantly increased and the final level was 14.9±3.6%. The 12-months-old 3xTgAD mice exhibited no improvement in learning over the 5 days of training (F(1, 113)=0.632; p>0.05) which was also evident in the memory performance (F(1, 21)=0.019; p>0.05). Vehicle-treated 3xTgAD mice showed a significant deficit in the memory test as compared to the vehicle-treated non-Tg mice (F(1, 17)=4.963; p<0.05), which was not reversed by treatment with THP. THP-treated 3xTgAD mice showed an equally significant deficit to vehicle-treated non-Tg mice (F(1, 19)=4.287; p=0.05).

As in the learning and memory analyses, THP induced a modest but not statistically significant trend towards an increase in BrdU+ cell survival. Basal level of BrdU+ cell survival was significantly decreased in 12-months-old 3xTgAD mice (201.1±51.5) as compared to age-matched non-Tg mice (F(1, 16)=135.58; p<0.00000001) (1460.8±99.3). In cell survival experiment, basal level of BrdU+ cells in 12-months old non-Tg mice was not significantly different from that of 6-months old (F(1, 14)=4.209; p>0.05) and 9-months old (F(1, 14)=2.438; p>0.05) non-Tg mice. THP exerted no significant effect on BrdU+ cell survival in 12-months-old non-tg mice (F(1, 15)=0.329; p>0.05) nor 12-months-old 3xTgAD mice (F(1, 19)=2.977; p>0.05).

Western blot analysis was performed to determine proliferating cell nuclear antigen (PCNA) expression levels in the hippocampus from the same animals that underwent behavior experiments. Results indicated that significant difference was only found between the vehicle-treated 6- and 12-month-old animals in the basal PCNA expression level (p<0.01, N=6). Twenty-one (21) day after THP injection, no significant difference was found between vehicle- and THP-treated animals at either 6, 9 or 12-month-old of age (p=0.34, p=0.10, and p=0.69, respectively; N=6), indicating APa had no sustained effect on cell proliferation in 3xTgAD mice at all ages tested. Further, these data provided evidence that aging male 3xTgAD mice retained the capacity to undergo S-phase of the cell cycle, and an age-related decline in such capacity is obvious at 12-month-old of age.

THP Increases Neural Progenitor Cell Proliferation in Hippocampus of 3xTgAD Mice in an Age Dependent Manner Total cell proliferation in hippocampus following one dose of THP (10 mg/kg) and 23 days of learning and memory (trace eye-blink conditioning) in 3, 6, 9, and 12 month aged mice was measured. FACS analysis detected immunopositive BrdU labeled cells by Beckman Coulter Cytomics FC 500 fluorescent flow cytometry. Significant THP-induced proliferation occurred in 3 and 6 month aged 3xTgAD mice and declined with age thereafter. The data for BrdU positive cells are summarized in FIGS. 15A-15H. Non-Tg mice, in contrast, did not show statistical significance between treatment and vehicle groups. The data indicates an age dependent decrease of neural progenitor cell proliferation in mice hippocampus from 3 to 12 month old mice and a genotype dependent decrease of neural progenitor cell proliferation in 3xTgAD mice at any age tested, particularly at 3 months old, indicating an early neurogenic deficit in 3xTgAD mice.

Example 11. 3α-Hydroxy-5α-Pregnan-20-One (THP) Significantly Increased Survival of BrdU Labeled Cells We sought to determine whether cell survival was directly attributable to THP exposure or whether cell survival was dependent on the training experience. Thus, the relationship between survival of BrdU positive cells and cognitive performance on the memory phase of the behavioral testing was analyzed. It was first determined whether the conditioning paradigm contributed to an increase in BrdU positive cells as this has been observed in behavioral paradigms in which the learning trials were 6-7 times greater than our 35/trials/day; eg >200+ trials/day. To determine the effect of training/learning, 3xTgAD mice were trained for 35 trials/day for 5 days and subsequently sacrificed at the end of the learning phase and brains processed for BrdU analysis by unbiased stereological analysis. The data demonstrate that the training/learning paradigm used in our behavioral analyses did not induce an increase in BrdU positive cells. In contrast, THP treated 3xTgAD mice exhibited a near doubling in the number of surviving cells generated 20 days prior to sacrifice. These data indicate that the mechanism of THP action is independent of training condition and is specific to THP.

THP Enhancement of Memory Function is Highly Correlated to the Number of Newly Formed BrdU Positive Cell Numbers We sought to determine the relationship between survival of BrdU positive cells and cognitive performance on the memory phase of the behavioral testing. Correlational analysis indicated a highly significant correlation between the number of surviving BrdU positive cells and memory performance for both the vehicle treated 3xTgAD mice and the THP treated 3xTgAD mice (Table 1).

TABLE 1

Correlation of survived BrdU cells with conditioned response (CR)

| | BrdU cells | % CR | CR/BrdU | R value |
|---|---|---|---|---|
| Vehicle (n = 10) | 652.8 | 28.33 | 0.0434 | 0.58 |
| APα (n = 12) | 1088 | 53.96 | 0.0496 | 0.68 |

Example 12. 3α-Hydroxy-5α-Pregnan-20-One (THP) Reduces Immunocytochemically Detectable β-Amyloid and Ptau Expression in the 6 Month Old 3×TgAD Male Mouse CA1 Region of the Hippocampus Triple transgenic mice were sacrificed at different ages as indicated, brain sections immunostained with anti-Amyloid β42 antibody and observed with peroxidase-DAB. Results of our assessment of pathology development replicate those of the LaFerla group and indicate that results from our laboratory are consistent with previously published characterization. At 3 months, cellular immunoreactivity (IR) was barely visible. At 6, 9 and 12 months, intracellular Aβ IR was apparent and intensity increased with age. Extraneuronal Aβ IR was rarely observed in 9-month-old 3×TgAD hippocampi but was consistently present in the hippocampus of 12-month-old 3×TgAD mice. Preliminary results indicate an age-dependent increase of Aβ levels in the cortex which is also in agreement with published reports.

In a pilot project to determine the impact of longterm exposure to THP, the impact of THP, 10 mg/kg s.c. thrice weekly for 3 months, on the progression of Alzheimer's disease (AD) pathology in 3-6 month old 3×TgAD mice was investigated. Mouse brain hemisphere sections were immunostained with specific antibody (6E10) against Aβ or HT7, which recognizes tau and PHF-tau between residue 159 and 163 and visualized with FITC conjugated second antibody. Observation of immunoreactivity indicated that both Aβ and ptau □IR were primarily localized within neuronal cell bodies. Quantitative analysis using SlideBook supported color mask and automatic color-cell counting system (3i Intelligent Imaging System) indicated that THP reduced the level of AD pathology markers in 3×TgAD mouse hippocampal CA1. Results of this pilot project indicate that THP reduced AD pathology burden in the subicular region of the hippocampus.

Figure 16:
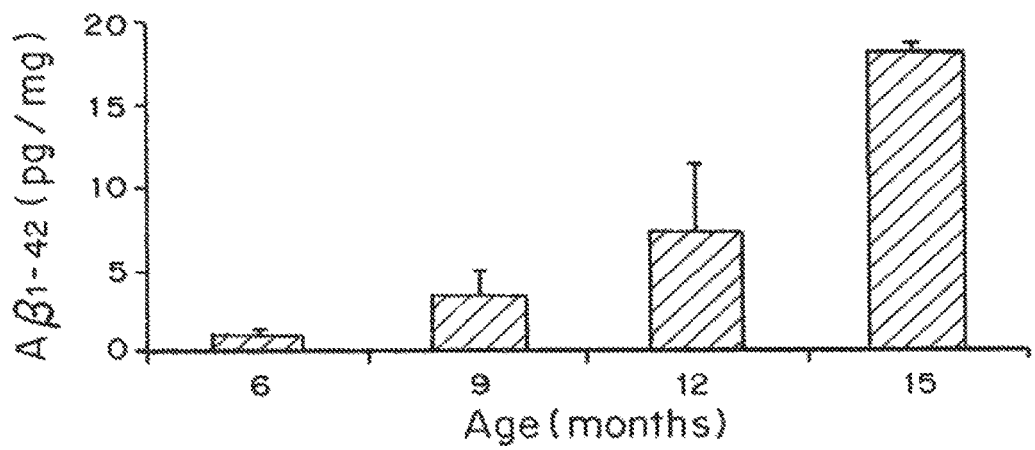
FIG. 16 is a bar graph showing the concentration of $A\beta_{1-42}$ (pg/mg) as a function of age of male mice (6, 9, 12, 15 months) transgenic for Alzheimer's disease (3×Tg-AD).

In another experiment, THP (10 mg/kg/week, administered once a week for 6 months) was administered to 9- and 12-month male mice transgenic for Alzheimer's disease (3×Tg-AD). The 9 month old animals were started on THP at 3 months of age prior to the development of beta amyloid, whereas the 12 month old animals were begun at 6 months of age when beta amyloid had already begun to accumulate within neurons. Typically, the development of intraneuronal beta amyloid is seen in 6 and 9 month old animals and the development of plaques in 12 month old animals. Plaques are rarely seen in 9 month old animals. This is shown in FIG. 16.

Figure 17:
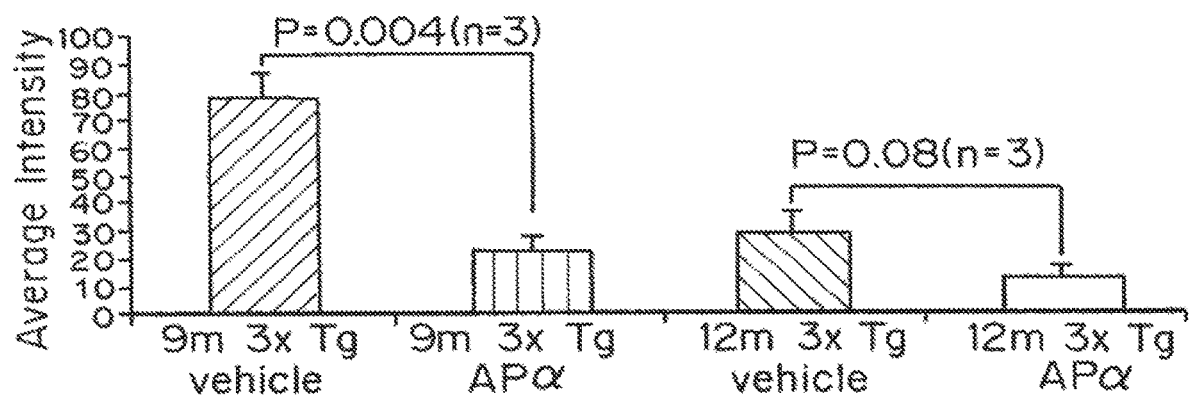
FIG. 17 is a graph showing the effect of 10 mg/kg 3α-hydroxy-5α-pregnan-20-one (APα, THP) administered once a week for 6 months, on the level of Abeta*56 (average intensity) in the cerebral cortex of 9- and 12-month male mice transgenic for Alzheimer's disease. Data is presented as average intensity for 9 month old 3×Tg/vehicle treated, 9 month old 3×Tg/APα treated, 12 month 3×Tg/vehicle treated, 12 month old 3×Tg/APα treated (from left to right across the x-axis) mice.

The results of THP administration are shown in FIG. 17. The graph shows that THP significantly decreased the amount of beta amyloid in the cerebral cortex of male mice transgenic for Alzheimer's disease. Western Blot analysis showed a form of beta amyloid termed Abeta*56, which is the oligomer (multiple amyloid beta peptides joined together) that, in animal studies, leads to memory loss in both transgenic Alzheimer mouse models and in rats injected with Abeta*56 (Lesne et al., Nature, 440, 352-357 (Mar. 16, 2006)). Thus, reducing Abeta*56 has the potential for preventing or reversing memory loss. In the 12 month old animals, the level of Abeta*56 was much lower, likely due to the development of beta amyloid plaques in these animals, which reduces the amount of Abeta*56. Western Blot analysis was also conducted for β-amyloid antibody 6E10 which recognizes the abnormally processed isoforms, as well as precursor forms of beta-amyloid protein. β-Amyloid expression from treated mice brain was shown as the labeled of 56 KD. This band at 56 KD corresponding to amyloid 12-mer oligomer. The results are shown in FIG. 18A. Treatment with THP partially reduced Aβ in both ages. THP decreased Aβ level by 25±4%, p=0.004 versus vehicle treatment in 9-month old 3×Tg-AD mice. In 12-month old 3×Tg-AD mice, APa induced a reduction 15±4%, p=0.05. Allopregnanolone was shown to attenuate Aβ accumulation. Brain sections were stained with beta amyloid antibody 6E10. Imaging showed 6E10 immunoreactivity was lower in THP-treated brain region CA1, Cortex and Amygdala than vehicle treated-brain, but not in the subiculum.

Immunocytochemical detection of beta amyloid showed that administration of THP substantially decreases Abeta*56 in hippocampal neurons. THP also decreases the immunoreactivity of phosphorylated tau, which is the basis for neurofibrillary tangles. Results of a study of 3 and 6 month old mice administered 10 mg/kg THP once a week for six months are shown in FIG. 19. The quantitation of the immunofluorescent signals for Abeta*56 and phosphorylated tau are shown in FIGS. 19A and 19B, respectively.

Figure 20A:
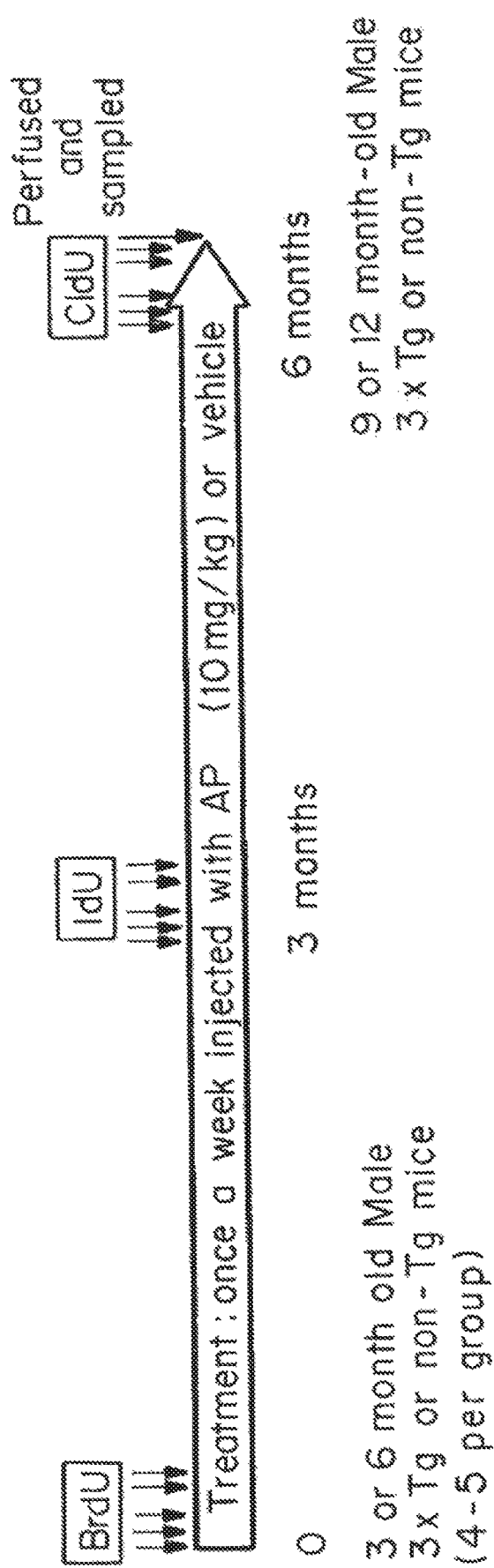
FIG. 20A is a schematic of the treatment protocol for evaluating the effects of long term 3α-hydroxy-5α-pregnan-20-one (APα, THP) administration on neural progenitor cell proliferation in hippocampus of 3×TgAD mice.
Figure 20B:
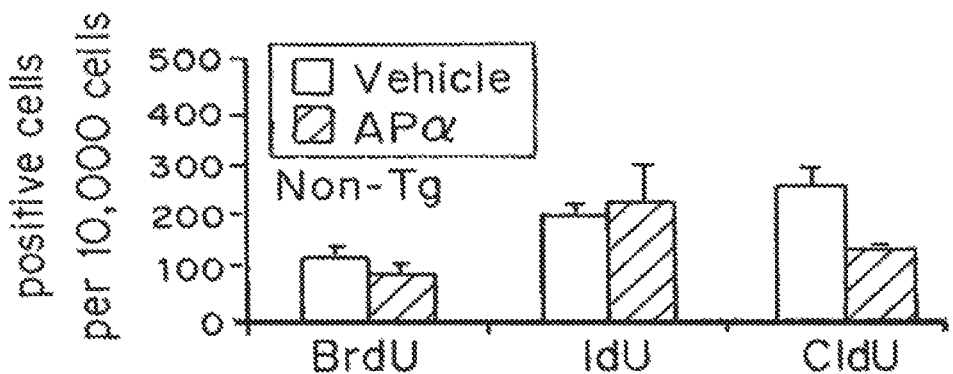
FIGS. 20B, 20C, 20D, and 20E are graphs showing the amount of positive cells per 10,000 cells as a function of the BrdU, IdU, and CldU for 3 month old mice treated for 6 months (FIGS. 20B and 20C) and 6 month old mice treated 6 months (FIGS. 20D and 20E).
Figure 20C:
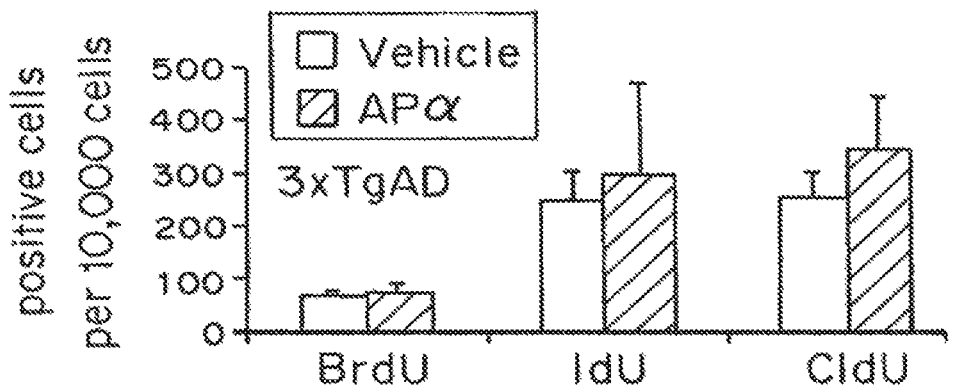
Figure 20D:
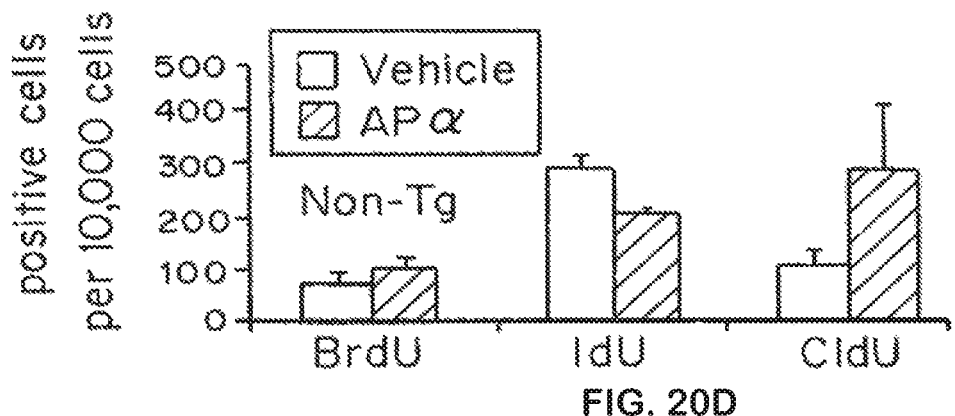
Figure 20E:
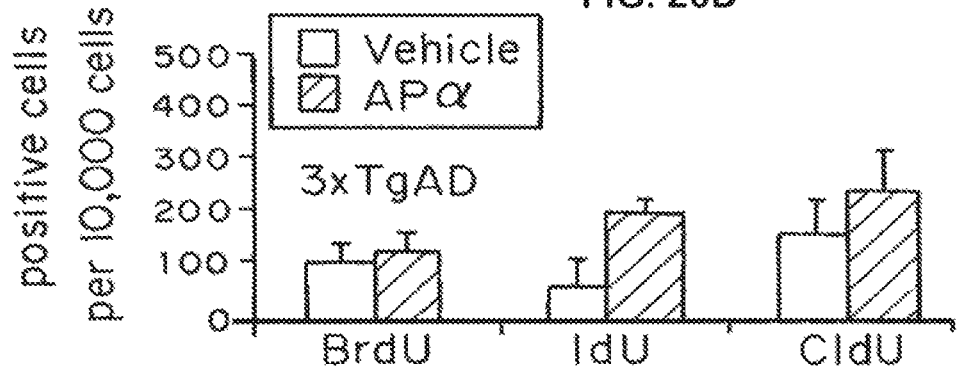

In yet another study, THP (10 mg/kg once a week for 6 months) was administered to mice beginning at 3 months or 6 months of age. The cell proliferation marker, 5-bromodeoxyuridine (BrdU) was injected (100 mg/kg) one hour after initial THP treatment and once per day for the next four days to detect cell proliferation and cell survival over the six month treatment period. After 3 months treatment, the mice were injected 5 times with another nucleotide analog iododeoxyuridine (one per day). After 6 months treatment, the mice were injected with chlorodeoxyuridine (CldU) 5 times (once per day). The treatment protocol is shown in FIG. 20A. Using specific antibodies, BrdU, IdU, and CldU incorporated cells will identify the 6 month survival, 3 month survival, and newly formed cells respectively. The mice were then sampled for biochemical, IHC, and flow cytometry assay. The results from mice with THP treatment initiated at 3 months old are shown in FIGS. 20B and 20C and initiated at 6 months old are shown in FIGS. 20D and 20E. The aim was to determine whether or not desensitization to THP was occurring. The results in FIGS. 20B-20E suggest that the brain is still responsive to THP at 3 and 6 months.

Example 13. Dose-Response and Time Course of 3α-Hydroxy-5α-Pregnan-20-One (THP)-Induced Proliferation in Human Neural Progenitor Cells (hNPC)

To determine the impact of THP on hNPC cell proliferation, a dose response (pM-nM) experiment was performed. Results of these analyses indicate:

a. THP, at doses within an achievable therapeutic range, increased human neural progenitor cell proliferation by 50%. Results of dose response analyses indicate that THP promoted human neural stem cell proliferation in a biphasic dose dependent fashion.

b. THP-induced human neural stem cell proliferation was first evident at 1 nM and maximal at 100 nM. Maximal proliferative efficacy was asymptotic at 100 nM, sustained at 250 and 500 nM and diminished at 1000 nM.

c. THP-induced hNPC proliferation was linear and evident at 3 hours and reached maximum at 6 hours.

d. Efficacy of THP as a neurogenic factor exceeded that of bFGF+heparin in promoting human neural progenitor cell proliferation.

e. Findings derived from hNPCs replicate results of THP-induced proliferation of rodent hippocampal NPCs.

Example 14. 3α-Hydroxy-5α-Pregnan-20-One (THP) Increases hNPC Proliferation while not Changing Neuronal Phenotype To determine the impact of THP on the stability of hNPC phenotype, hNPCs were double labeled with BrdU, Tuj1 and MAP2, or GFAP. Quantitative analysis of phenotype (DAPI-positive blue nuclei as marker of total cell number) indicated that THP significantly increased the number of BrdU positive hNPCs while not changing the proportion of Tuj1, MAP2 or GFAP cells vs. vehicle treated hNPCs.

AP α-Induced hNPC Cell Proliferation is Blocked by GABAAR Antagonist

Previously, we demonstrated that THP-induced rat NPC proliferation is mediated by GABAAR, as the GABAAR antagonist bicuculline abolished the THP-induced intracellular calcium concentration increase, required for THP-induced rNPC cell proliferation. To determine whether the same mechanisms of THP-induced proliferation in rodent derived NPCs could be generalized to humans, we determined the requirement of the GABAAR by antagonizing the GABAAR with bicuculline followed by assessment of THP-induced hNPC cell proliferation. Results of those analyses indicate that 250 nM THP was as efficacious a proliferative factor as the positive control, bFGF. Both vehicles, alcohol and DMSO, had no significant effect on basal hNPC proliferation. Bicuculline completely antagonized, THP-induced hNPC proliferation. These results indicate that as in rNPCs, THP-induced proliferation requires the GABAAR.

Human Neural Progenitor Cells (hNPC) Express a Specific Combination of GABAAR (GBRC) Subunits.

Activation of GABAAR in mature neurons leads to hyperpolarization via an influx of chloride. In contrast, in immature neurons and neural progenitors activation of the GABAAR leads to a depolarization through an efflux of chloride. It is hypothesized that hNPCs responsive to THP will exhibit a GABAAR phenotype that is comparable to extrasynaptic GABAAR. The tonic conductances of the extrasynaptic GABAARs may be more conducive to depolarization required for opening voltage dependent L-type calcium channels and downstream signaling cascades required for cell cycle activation.

To determine GABAAR receptor subunit expression in hNPC cells, reverse transcriptase PCR (RT-PCR) using total RNA extracted from cultured hNPC and human fetal brain was performed, the latter used as a control to verify all the primers used are functional in RT-PCR. cDNA from total human fetal brain total RNA showed positive amplification of GBRC subunits. In contrast, α2 and α5, but not α1 and α4 were expressed in hNPC. In addition, a much higher expression of δ subunit in hNPC was also observed. These results are consistent with recent data in the literature showing that the THP binding pocket required for direct activation of the GBRC requires a pocket formed by the interface between α and δ subunits in which THP spans the interface between the 2 subunits.

Figure 21A:
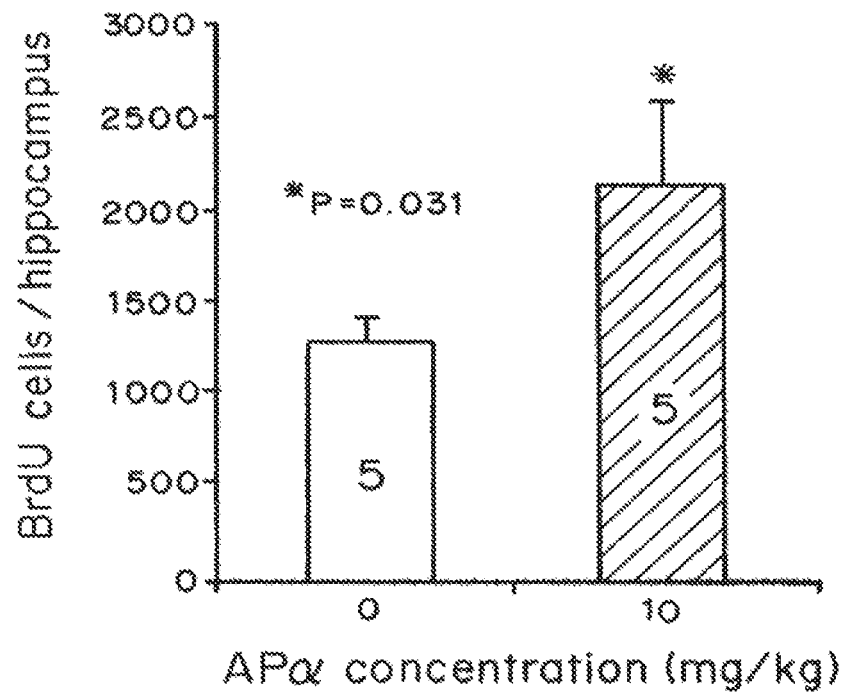
FIGS. 21A-D show the effect of α-hydroxy-5α-pregnan-20-one (APα, THP) dose and method of administration on the promotion of neural progenitor cell proliferation in three month old 3×TgAD mouse hippocampus.
Figure 21B:
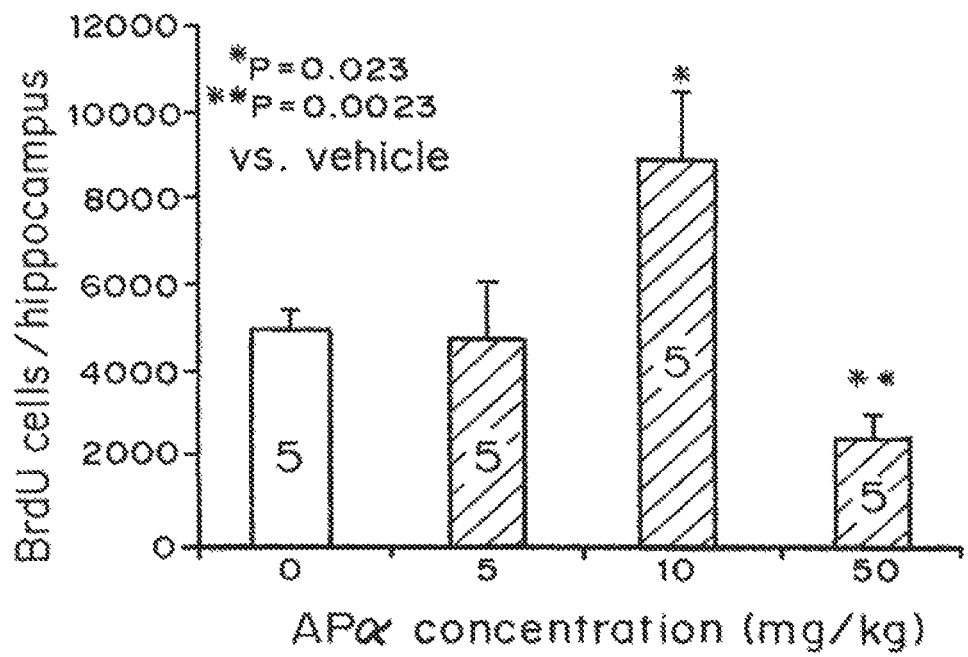
Figure 21C:
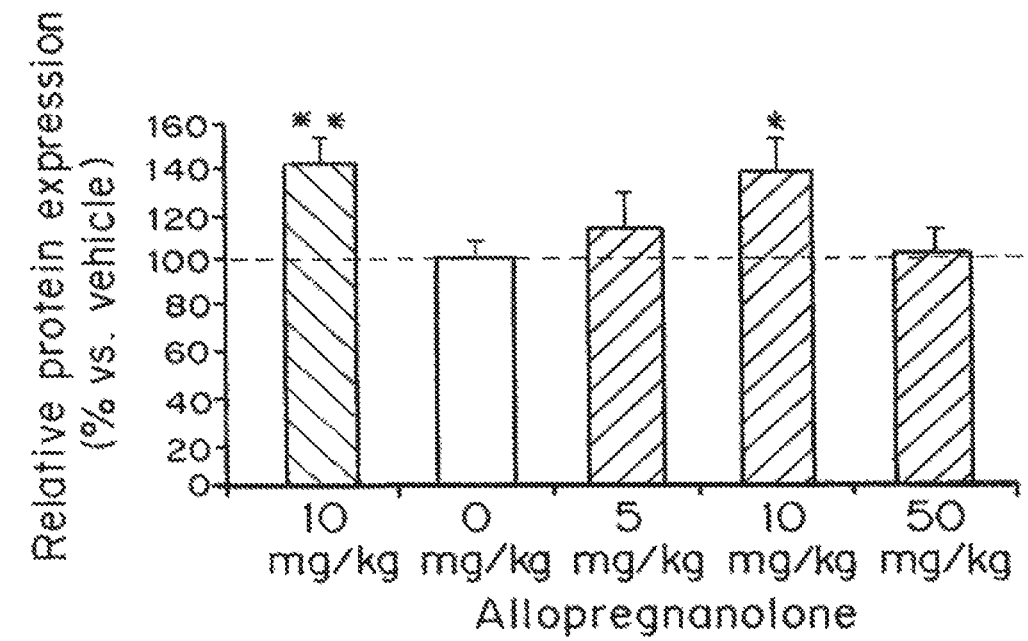
Figure 21D:
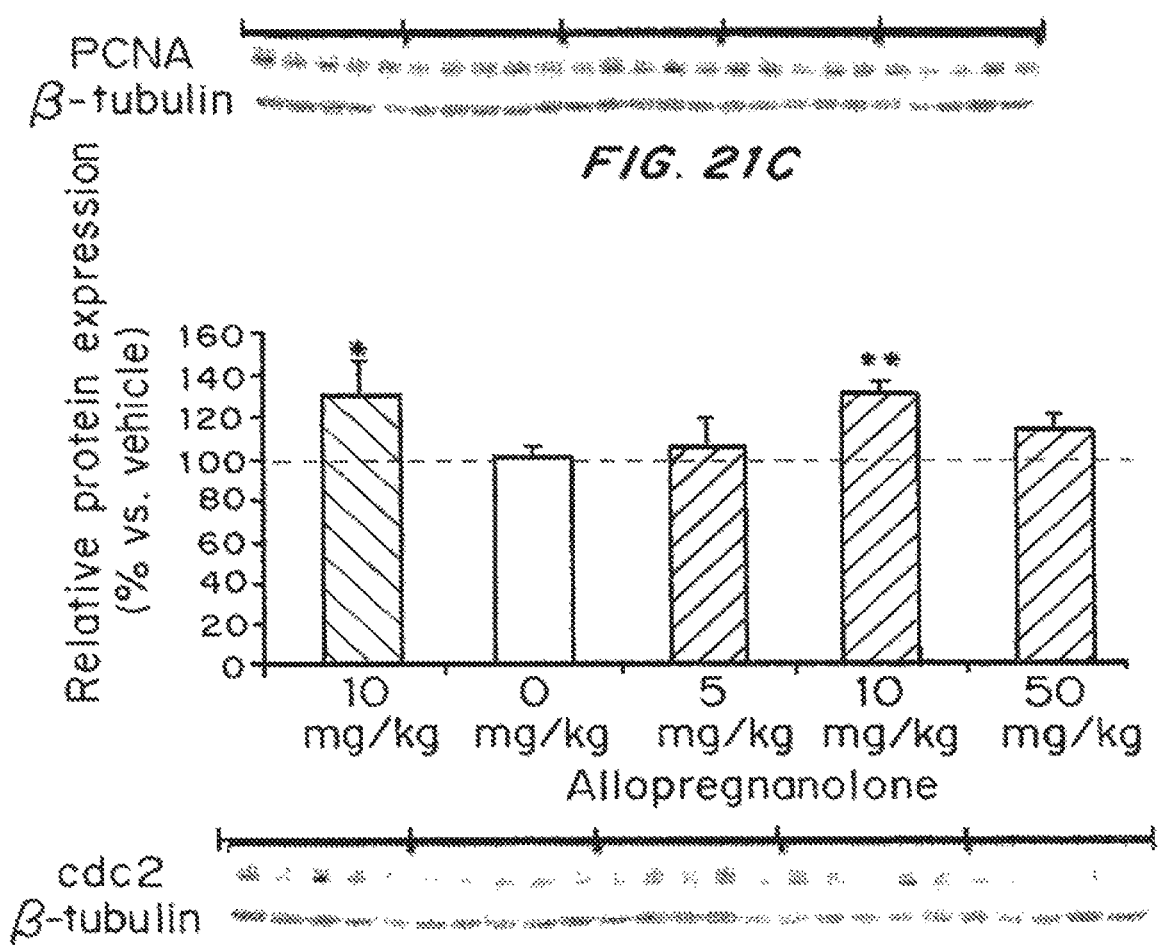

Example 15. Transdermal THP Formulation Promotes Neural Progenitor Cell Proliferation in Three Month Old Male 3×TgAD Mouse Hippocampus Flow cytometry assay detected total BrdU labeled cells 24 hours following THP administration via (A) subcutaneous and (B) transdermal routes. The optimal dose to significantly increase BrdU cell numbers was found to be 10 mg/kg for both routes and confirmed previous results obtained by unbiased stereology. BrdU (100 mg/kg) was administered by intraperitoneal injection one hour after THP administration. Transdermal gel THP dose-response for 5, 10, and 50 mg/kg (FIG. 21B) was compared to 0 mg/kg control vehicle (negative control) and subcutaneous injection of 10 mg/kg (positive control) (FIG. 21A). THP significantly increases BrdU cell numbers in 10 mg/kg dose. Immunoblots of proliferating cell nuclear antigen (PCNA), an S-phase marker and cyclin dependent kinase 1 (CDK1/cdc2), an M-phase marker, are shown in FIGS. 21C and 21D, respectively. Hippocampus protein expression of PCNA and CDK1/cdc2 was normalized to β-tubulin loading control and compared relative to the vehicle control by immunoblot. Both bands were incorporated in the analysis for CDK1/cdc2; the upper band represents the inactive form, while the lowe band represents the active form. The data were analyzed by one way ANOVA followed by a t test (two samples assuming equal variance) vs. vehicle. Data are presented as the mean±SEM, n=5, *=P<0.05, and **=P<0.01.

Figure 22:
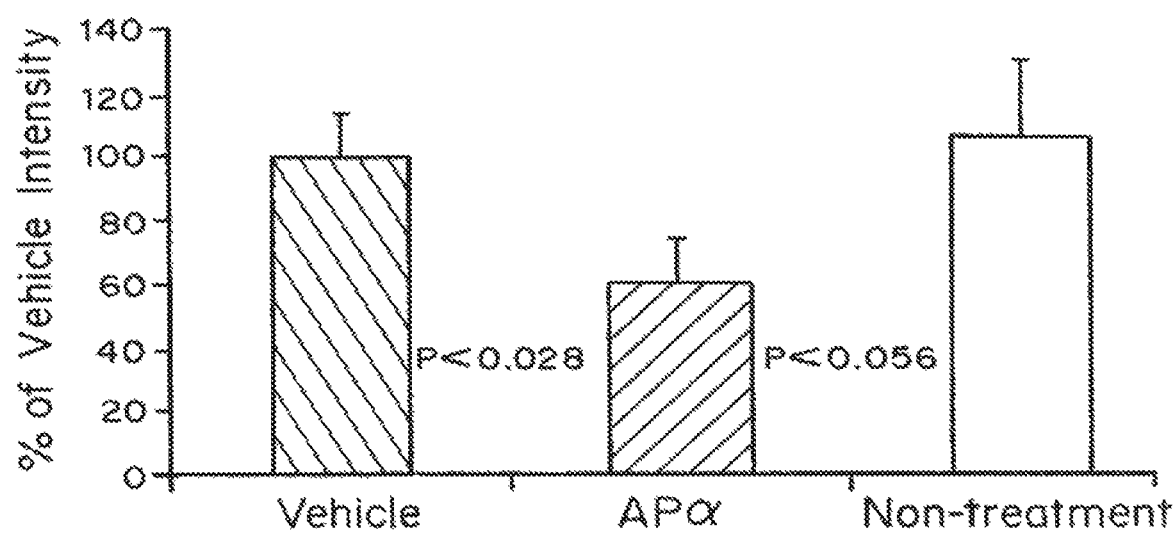
FIG. 22 is a graph showing quantification of 28 kDa β-amyloid oligomer band detected with β-amyloid antibody 6E10 (percent of vehicle intensity) in 3 month old 3×Tg-AD mice following vehicle, or 10 mg/kg α-hydroxy-5α-pregnan-20-one (alloprenanoione, APα, or THP) administered transdermally, THP (10 mg/kg) once a week for 6 months. Non-treatment is also shown.

Example 16. Effect of Transdermal THP on β-Amyloid Expression in 9-Month Male 3×Tg-AD Mice THP (10 mg/kg) or vehicle was transdermal treated once a week to 3-month-old 3×Tg-AD mice for 6 months. Western blot analysis was conducted using brain protein from hippocampus with beta amyloid antibody 6E10, which recognizes the abnormally processed isoforms, as well as precursor forms of beta amyloid protein. Three major immunoreactive bands were detected in nitrocellulose membrane from 9-month 3×Tg-AD mice brain (hippocampus), but the band in age-matched nonTg mice sample was not detectable. Two full-length APP bands around 100 kDa and oligomer band around ~28 kDa were detected with 6E10 antibody. Quantification of 28 kDa β-amyloid oligomer band intensity level (relative to β-actin level) shows that treatment with THP partially reduced β-amyloid expression. THP decreased intensity level by 39±13% versus vehicle treatment in 9-month old 3×Tg-AD mice (n=10, p<0.05, FIG. 22).

Example 17. Chronic Administration of THP Decreases Alzheimer Disease Pathology in Triple Transgenic Mice THP (10 mg/kg) or vehicle was subcutaneously administered once a month, once per week for 6 months, or once every other day for 3 months. Brain sections of treated mice were stained with beta amyloid antibody 6E10 which recognizes the abnormally processed isoforms, as well as precursor forms of beta amyloid protein. The representative image shows that different treatment paradigm reveals different effects. THP significantly decreases 6E10 immunoreactivity when treatment every other day for 3 months or once a week for 6 months, but no effect when treated once a month.

Further studies were conducted using a dosing regime of once a week for six months administered subcutaneously. Three and six months old 3×Tg-AD and age-matched non-Tg mice were chosen for the experiments, since AD pathology (Aβ) starts development at 3-month and abundant accumulation at 6-months. Allopregnanolone was subcutaneously (s.c.) administrated with 10 mg/kg once per week for 6 months. For neurogenesis and neurosurvival study, BrdU, IdU and CIdU were intraperitoneal (i.p.) injected at the first 5 days, mid 5 days and 5 days before sacrifice during 6-month treatment. After 6 months of allopregnanolone treatment, mice, at 9- and 12-month old, were sacrificed.

THP Reduces β-Amyloid 27 and 56 kDa Expression in 9- and 12-Month Male 3×Tg-AD Mice Western blot analysis was conducted using brain protein from frontal-parietal-temporal cortex with beta amyloid antibody 6E10, which recognizes the abnormally processed isoforms, as well as precursor forms of beta amyloid protein. The expression of different forms of beta amyloid in 3×Tg-AD mice was characterized. Three major immunoreactive bands were detected in the samples from 9- and 12-month 3×Tg-AD mice brain (frontal-parietal cortex), but the bands in age-matched non-Tg mice were very faint even though the intensity of the bands increased with aging.

The bands around ~27 kDa and 56 kDa oligomers were detected with 6E10 antibody as hexamers (6-mer) and dodecamers (12-mer). One 27-month 3×Tg brain sample was included as a positive control. The oligomer bands intensity was much stronger for older mice. Quantification of these two oligomer bands intensity level (relative to b-actin level) shows that treatment with APa partially reduced Aβ*56 in both ages. THP decreased intensity level by 25±4% versus vehicle treatment in 9-month old 3×Tg-AD mice (n=5, p<0.01). In 12-month old 3×Tg-AD mice, THP induced a reduction of 15±4% (n=3-4, p=0.05. Aβ 6-mer at 27 kDa band intensity was also reduced by THP-treatment, 35±10%, p<0.05, but no difference in 12-month old 3×Tg mice. Immunohistochemistry analyses showed a widespread reduction of Aβ staining in THP-treated brain sections. These results show that intraneuronal Aβ immunoreactivity is lower in THP-treated 9-month old 3×Tg-AD mice hippocampus, cortex, and amygdala than in vehicle-treated brain, but not in subiculum.

Such inhibition could be highly significant for AD treatment, because oligomeric Aβ species in the brain currently is considered as a major risk factor for the onset and progression of cognitive decline in AD. Although Aβ plaques are the most visible and well characterized amyloid pathology in the AD brain, recent studies indicate that Aβ oligomers, especially Aβ*56, is mainly responsible for AD dementia and memory deficits. Thus, allopregnanolone-induced oligomer attenuation may improve cognitive function.

THP Reduces ABAD Expression in 3×Tg-AD Mice

Beta amyloid binding alcohol dehydrogenase (ABAD) was probed with antibody ERAB (1:500, Abcam). THP-treatment decreased ABAD level by 30±4% (p<0.05) and 20±7% (p=0.07) respectively, in 9-month and 12-month 3×Tg mice relative to the vehicle-treated control. Immunofluorescent staining using goat polyclonal anti-ERAB (Santa Cruz) confirmed the results obtained by Western Blot analysis. The concentration of ABAD immunoactive cells is less in THP-treated brains than in the brains treated with the vehicle.

The interaction of Aβ and ABAD disrupts mitochondrial function. It has been reported that the increase in mitochondrial Aβ correlated with the increase in ABAD level in the 3×Tg-AD mouse brain which resulted in neurotoxicity due to the formation of mitochondrial deposits of Aβ. THP significantly decreased ABAD expression in 3×Tg-AD mice which should reduce the interaction of Aβ and ABAD. Minimizing the interaction of Aβ and ABAD should be beneficial for improving mitochondria function in AD patients.

THP Modulates Phospho-Tau Expression in 3×Tg-AD Mice

Western blot analysis was conducted with monoclonal phospho-tau antibody (AT8, PIERCE) which recognizes phosphorylated tau serine 202. Immunoblotting data did not show a significantly reduction of AT8 immunoreactivity in mouse brains treated with THP. However, immunostaining with AT8 showed lower levels of immunoreactivity in THP-treated hippocampal CA1, cortex and amygdala.

A direct relationship between Aβ and tau pathologies in 3×Tg-AD mice has be reported. Specifically, it has been reported that Aβ causes tau accumulation and subsequent phosphorylation. Removal of intraneuronal Aβ via immunotherapy leads to tau clearance from neurons following the Aβ itself clearance. Therefore, the reduction of phosphor-tau level with APβ□ appears to closely related to the reduction of intracellular Aβ levels.

THP Treatment Inhibited Microglial Reaction

Western blot analysis was conducted with rabbit polyclonal anti-CD11b/c (OX42) which recognizes reactive microglial cells. The band intensities trended towards a decrease in THP treated mouse brains, but there are no significant differences in 9-month 3×Tg p=0.07 and 12-month p=0.10. The immunofluorescent staining with rabbit polyclonal anti-Iba1 (1:1000, Woka) showed lower levels of immunoactivity in THP-treated hippocampal CA1.

Microglial cells become activated in AD brains. Activated microglia cells generate the wide panel neurotoxic agents, inducing neurodegeneration and neuronal loss. Therefore, suppression of microglial activation should be beneficial for treatment of this disease. Our results show that THP treatment inhibited microglia activation, suggesting that THP could be one a potential candidate drugs for AD prevention and therapy.

THP Increased Myelination in Mouse Brain

Western blot analysis using anti-CNPase antibody, an oligodendrocyte marker which generates myelin, shows THP increased CNPase expression in 9-month nonTg mice (p<0.01) and 3×TgAD mice (p<0.05). In 12-month non-Tg mice, there were no significant difference, but CNPase expression trended towards an increase (p=0.045) in 3×TgAD mice. Immunofluorescent staining shown the immunoreactivity increased in CA1, entorhinal cortex, and primary somatosensory cortex.

Overall, the results discussed above indicate that THP treatment reduces Aα oligomer accumulation, paralleled with a reduction in ABAD expression and microglia activation. Collectively, these findings indicate that in a mouse model of AD, THP induces a profile consistent with reduction and or delay in progression of Alzheimer's pathology. These findings have important implications for THP as a therapeutic candidate for the treatment of Alzheimer's disease pathology.

All patent and non-patent references cited in this specification are herein incorporated by reference as if each individual patent or non-patent reference were specifically and individually indicated to be incorporated by reference.

Although the foregoing embodiments of the invention has been described in some detail by way of illustration and example for purposes of clarity and understanding, it will be readily apparent to those of ordinary skill in the art in light of the teachings of this invention that certain changes and modifications may be made thereto without departing from the scope of the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method to improve learning and/or memory in an individual having Alzheimer's disease or dementia,
the method comprising administering to the individual a systemic dose of an effective amount of 3α-hydroxy-5α-pregnan-20-one, or a pharmaceutically acceptable salt thereof, to improve learning and/or memory in the individual,
wherein the dose of the 3α-hydroxy-5α-pregnan-20-one, or a pharmaceutically acceptable salt thereof, is administered as a single dose once a week or less frequently than once a week.

2. The method of claim 1, wherein the 3α-hydroxy-5α-pregnan-20-one, or a pharmaceutically acceptable salt thereof is present in an amount effective to improve learning and/or memory in an individual having Alzheimer's disease.

3. The method of claim 2, wherein the 3α-hydroxy-5α-pregnan-20-one, or a pharmaceutically acceptable salt thereof is present in an amount effective to improve learning and/or memory deficits in the individual.

4. The method of claim 1, wherein the 3α-hydroxy-5α-pregnan-20-one, or a pharmaceutically acceptable salt thereof is formulated as a pharmaceutical composition for systemic administration via a route selected from the group consisting of transdermal administration, subcutaneous injection, intravenous injection and pulmonary administration.

5. The method of claim 4, wherein the formulation includes a dextrin.

6. The method of claim 4, wherein the composition is in the form of a transdermal gel.

7. The method of claim wherein 1 the dosage is administered in a gel.

8. The method of claim 1 wherein the dosage is administered by injection.

9. The method of claim 1 wherein the dosage is immediately released following administration.

10. The method of claim 6, wherein the gel comprises a thickening agent.

11. The method of claim 10, wherein the thickening agent is a cross linked acrylic acid polymer.

12. The method of claim 11, wherein the crosslinked acrylic acid polymer is carbomer 940.

13. The method of claim 6, wherein the gel further comprises a solvent selected from the group consisting of diglycol monoethyl ether, ethylene glycol, propylene glycol, dimethyl isosorbide, isopropyl alcohol, and ethanol.

14. The method of claim 6, wherein the gel further comprises one or more penetration enhancers.

15. The method of claim 1, wherein the composition is administered in less than one day a week for a period of at least one month.

16. The method of claim 1, wherein the composition is administered in less than one day a week for a period of at least three months.

17. The method of claim 1, wherein the composition is administered in less than one day a week for a period of at least six months.

18. The method of claim 17, wherein the composition is administered in less than one day a week for a period of six months.

* * * * *

UNITED STATES PATENT AND TRADEMARK OFFICE
CERTIFICATE OF CORRECTION

PATENT NO. : 11,207,331 B2  
APPLICATION NO. : 15/603267  
DATED : December 28, 2021  
INVENTOR(S) : Roberta Diaz Brinton and Jung Ming Wang Page 1 of 1

It is certified that error appears in the above-identified patent and that said Letters Patent is hereby corrected as shown below:

In the Specifications

On Column 1, Line 21, before "FIELD OF THE INVENTION", please insert the following paragraph:
-- STATEMENT REGARDING FEDERALLY SPONSORED RESEARCH OR DEVELOPMENT
This invention was made with government support under U01 AG047222, U01 AG031115, and AG046148 awarded by the National Institutes of Health. The government has certain rights in the invention. --

Signed and Sealed this
First Day of April, 2025

Coke Morgan Stewart
*Acting Director of the United States Patent and Trademark Office*